(12) United States Patent  
Yu et al.

(10) Patent No.: US 8,252,778 B2
(45) Date of Patent: Aug. 28, 2012

(54) HIGHLY FLUORINATED OILS AND SURFACTANTS AND METHODS OF MAKING AND USING SAME

(75) Inventors: Yihua Yu, Ellicott City, MD (US); Zhong-Xing Jiang, Dundalk, MD (US)

(73) Assignee: University of Utah Research Foundation, Salt Lake City, UT (US)

( * ) Notice: Subject to any disclaimer, the term of this patent is extended or adjusted under 35 U.S.C. 154(b) by 801 days.

(21) Appl. No.: 12/294,424

(22) PCT Filed: Mar. 26, 2007

(86) PCT No.: PCT/US2007/007459
§ 371 (c)(1),
(2), (4) Date: Sep. 24, 2008

(87) PCT Pub. No.: WO2007/112100
PCT Pub. Date: Oct. 4, 2007

(65) Prior Publication Data
US 2009/0264397 A1   Oct. 22, 2009

Related U.S. Application Data

(60) Provisional application No. 60/785,463, filed on Mar. 24, 2006.

(51) Int. Cl.
  *A61K 31/33*   (2006.01)
  *A61K 49/04*   (2006.01)
(52) U.S. Cl. ...................................... 514/183; 424/9.44
(58) Field of Classification Search ........................ None
    See application file for complete search history.

(56) References Cited

PUBLICATIONS

Dale et al., Acta. Chemica. Scan., 1992, 46(3), pp. 271-277.*

* cited by examiner

*Primary Examiner* — Brian Gulledge
(74) *Attorney, Agent, or Firm* — Ballard Spahr LLP

(57) ABSTRACT

Disclosed are compounds comprising the structure:

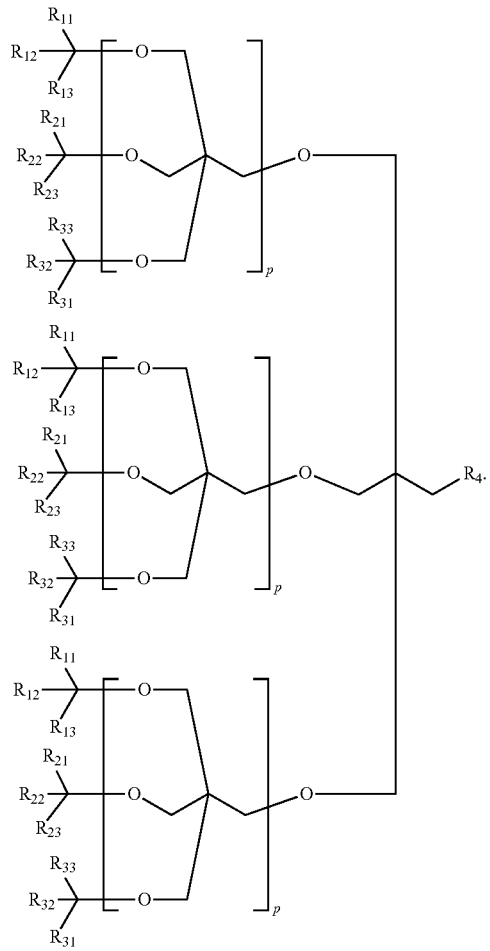

In one aspect, the compounds exhibit maximum symmetric branching. Also disclosed are bilayers, micelles, coatings, and nanoparticles comprising the disclosed compounds. Also disclosed are processes for the preparation of the disclosed compounds and methods of using the disclosed compounds. Also disclosed are highly fluorinated dendrons and methods for making same. Also disclosed are methods for Fluorous Mixture Synthesis and tagging. This abstract is intended as a scanning tool for purposes of searching in the particular art and is not intended to be limiting of the present invention.

12 Claims, 6 Drawing Sheets

| 0 mg | 80 mg | 120 mg | 160 mg | 200 mg |

HIGHLY FLUORINATED OILS AND
SURFACTANTS AND METHODS OF MAKING
AND USING SAME

CROSS REFERENCE TO RELATED APPLICATIONS

This application claims the benefit of U.S. Application No. 60/785,463, filed Mar. 24, 2006, which is hereby incorporated herein by reference in its entirety.

ACKNOWLEDGEMENT

This invention was made with government support under Grants Nos. EB 004416 and EB 002880 awarded by the National Institutes of Health. The United States government has certain rights in the invention.

BACKGROUND

A. Highly Fluorinated Compounds

It is well known to employ fluorine groups in organic molecules to enhance the hydrophobicity of the compounds. Also, fluorinated surfactants generally have higher surface activities in comparison with their non-fluorinated counterparts. However, common fluorinated compounds, for example polytetrafluoroethylene, typically use only unbranched or asymmetrical fluorinated moieties. The consequence of less-than-maximum branching is that the surface area of the fluorocarbon moiety is not maximized. For surfactants, this is a distinct advantage. The consequence of asymmetrical branching is that the terminal groups of the fluorocarbon moiety have different chemical environment. This can also reduce the effectiveness of surface protection. Also, for $^{19}F$ MRI applications, variation in chemical environments of fluorine atoms leads to split $^{19}F$ signals, thereby reducing the sensitivity for MRI detection.

B. Targeted Radiotherapy

Targeted radiotherapy is a promising cancer treatment modality. Larson, S. M. & Krenning, E. P. A pragmatic perspective on molecular radionuclide therapy. [J. Nucl. Med. 46 (Suppl. 1) 1S-3S, 2005]. In targeted radiotherapy, ionizing radionuclides (e.g., $^{90}Y$, $^{131}I$) are delivered to the tumor site via a targeting moiety to which they are attached. The targeting moiety can be monoclonal antibodies (mAb), peptides or any other molecules which recognize receptor molecules that are over-expressed by tumor cells. Compared with external beam radiation, targeted radiotherapy has two significant advantages: it can reduce radiation damage to normal tissues and it can reach multiple small metastases. [de Jong, M., Kwekkeboom, D., Valkema, R. & Krenning, E. P. Radiolabelled peptides for tumour therapy: current status and future directions. Eur. J. Nucl. Med. & Mol. Imag. 463-469, 2003; Kaltsas, G. A., Papadogias, D., Makras, P. & Grossman, A. B. Treatment of advanced neuroendocrine tumours with radiolabelled somatostatin analogues. Endocrine-Related Cancer, 12, 683-699, 2005].

The emergence of targeted radiotherapy as an effective cancer treatment modality is demonstrated by the regulatory approvals of two radioimmunotherapy drugs (Zevalin® and Bexxar®) for treating non-Hodgkin's lymphoma [Drug Label Information for Zevalin® and Bexxar®. Available at Drugs@FDA.]. In addition, OctreoTher®, which uses an octapeptide for tumor targeting, is under clinical trials for treating neuroendocrine tumors [Kaltsas, G. A., Papadogias, D., Makras, P. & Grossman, A. B., Treatment of advanced neuroendocrine tumours with radiolabelled somatostatin analogues. Endocrine-Related Cancer, 12, 683-699, 2005; Smith, M. C., Liu, J., Chen, T., Schran, H., Yeh, C.-M., Jamar, F., Valkema, R., Bakker, W., Kvols, L., Krenning, E. & Pauwels, S. OctreoTher™: ongoing early clinical development of a somatostatin-receptor-targeted radionuclide antineoplastic therapy; Bushnell, et al., Evaluating the clinical effectiveness of 90Y-SMT 487 in patients with neuroendocrine tumors. J. Nucl. Med. 44, 1556-1560, 2003].

The first step in developing targeted radiotherapeutic drugs is, of course, drug discovery, which includes the identification of the target (i.e., which receptor) and the drug (which ligand and which radio-nuclide). However, once a radiotherapeutic drug has been discovered, it still faces enormous challenges in its delivery, as evidenced by the complex dosing schedules of Zevalin® and Bexxar®, which take about two weeks [Drug Label Information for Zevalin® and Bexxar®. Available at Drugs@FDA.]. The origin of this delivery challenge lies in the large variations among patients in terms of drug pharmacokinetics and tumor microenvironment. Pharmacokinetics refers to the distribution, retention and excretion profiles of the radiotherapeutic drug. Large pharmacokinetic variations among patients have been observed for both mAb- and peptide-based radiopharmaceuticals [Kaltsas, G. A., Papadogias, D., Makras, P. & Grossman, A. B. Treatment of advanced neuroendocrine tumours with radiolabelled somatostatin analogues. Endocrine-Related Cancer, 12, 683-699, 2005; Forsell-Aronsson, E., Bernhardt, P., Nilsson, O., Tissel, L.-E., Wangberg, B. & Ahlman, H. Biodistribtuin data from 100 patients i.v. injected with 111In-DTPA-D-Phe-octreotide. Acta Oncologica 43, 436-442, 2004; Barone, et al., Patient-specific dosimetry in predicting renal toxicity with 90Y-DOTATOC: relevance of kidney volume and dose rate in finding a dose-effect relationship. J. Nucl. Med. 99S-106S, 2005; Wahl, R. L. Tositumomab and 131I therapy in non-Hodgkin's lymphoma. J. Nucl. Med. 46 (Suppl. 1), 128S-140S, 2005]. Tumor microenvironment refers to the physiological and metabolic conditions of tumors which also vary significantly from individual to individual [Gillies, R. J., Raghunand, N., Karczmar, G. S. & Bhujwalla, Z. M. MRI of the tumor microenvironment. J. Mag. Reson. Imag. 16, 430-450, 2002]. In the context of radiotherapy, the most relevant tumor microenvironmental parameter is oxygen tension ($pO_2$). This is because hypoxic tumor cells are more radioresistant [Vaupel, P. Tumor microenvironmental physiology and its implications for radiation oncology. Seminars in Radiation Oncology, 14, 198-206, 2004] and $pO_2$ has been found to correlate with treatment outcomes of beam radiation and targeted radiotherapy [Nordsmark, M., Overgaard, M. & Overgaard, J. Pretreatment oxygenation predicts radiation response in advanced squamous cell carcinoma of the head and neck. Radiother. Oncology, 41, 31-39, 1996; Nordsmark, M. & Overgaard, J. A confirmatory prognostic study on oxygenation status and loco-regional control in advanced head and neck squamous cell carcinoma treated by radiation therapy. Radiother. Oncol. 57, 39-43, 2000; Fyles, et al., Oxygenation predicts radiation response and survival in patients with cervix cancer. Radiother. Oncology, 48, 149-156, 1998; Brizel, D. M., Dodge, R. K., Clough, R. W. & Dewhirst, M. W. Oxygenation of head and neck cancer:

changes during radiotherapy and impact on treatment outcome. Radiother. Oncology, 53, 113-117, 1999; O'Hara, J. A., Goda, F., Demidenko, E. & Swartz, H. M. Effect on regrowth delay in a murine tumor of scheduling spit dose radiation based on direct pO2 measurements by EPR oximetry. Radia. Res. 150, 549-556, 1998; O'Hara, et al., Response to radioimmunotherapy correlates with tumor pO2 measured by EPR oximetry in human tumor xenografts. Radia. Res. 155, 466-473, 2001].

However, conventional targeted radiotherapy methods typically fail to effective use a high degree of fluorine content and/or a high degree of symmetry to provide a mechanism for high sensitivity $^{19}$F NM analysis.

Despite conventional fluorinated compounds and conventional targeted radiotherapy, there remains a need for methods and compositions that overcome these deficiencies.

SUMMARY

Disclosed are compounds comprising the structure:

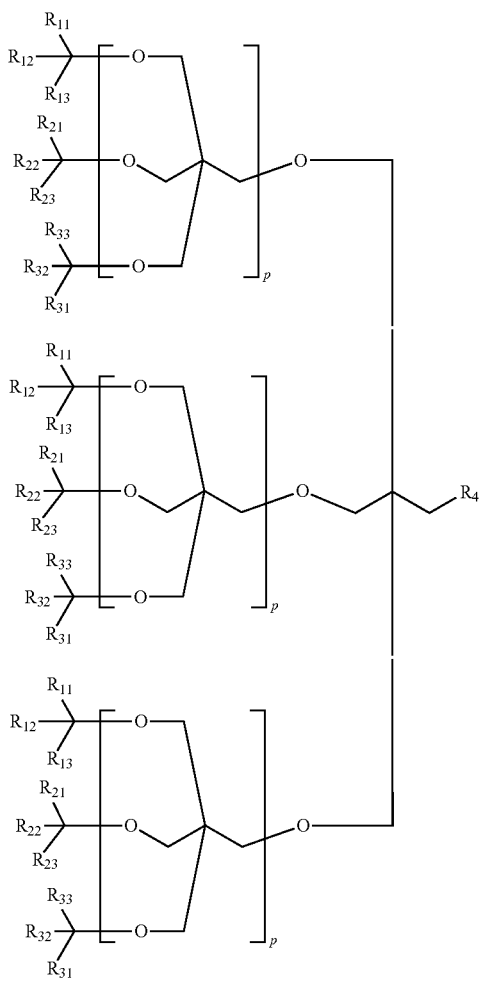

wherein p is a non-negative integer; wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$ or alkyl; and wherein $R_4$ is H, OH, OBn, $OC(CF_3)_3$, alkyl, or alkoxy.

Also disclosed are compounds comprising the structure:

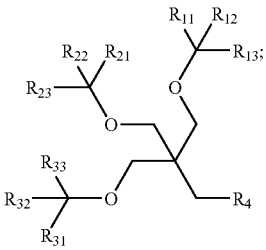

wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$ or alkyl; and wherein $R_4$ is H, OH, OBn, $OC(CF_3)_3$, alkyl, or alkoxy.

Also disclosed are compounds comprising a hydrophilic moiety and a hydrophobic moiety, wherein the hydrophobic moiety exhibits maximum symmetric branching.

Also disclosed are bilayers, micelles, and coatings comprising the disclosed compounds.

Also disclosed are processes for the preparation of a compound comprising the structure:

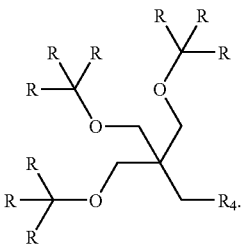

wherein R is H, $CH_3$, $CF_3$ or alkyl and wherein $R_4$ is H, OH, OBn, alkyl, or alkoxy; the process comprising the steps of: providing a triol, reacting the triol with tert-butanol or non-afluoro-tert-butanol to provide a tri-tert-butyl ether or a triperfluoro-tert-butyl ether.

Also disclosed are the products produced by the disclosed processes.

Also disclosed are nanoparticles comprising the disclosed compounds.

Also disclosed are multifunctional delivery vehicles comprising at least one of the disclosed compounds, wherein $R_4$ comprises a moiety having the structure:

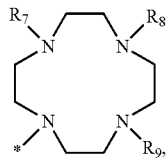

wherein $R_7$, $R_8$, and $R_9$ are, independently, H, $CH_2CO_2H$, or alkyl; and at least one of the disclosed compounds, wherein $R_4$ comprises a moiety having the structure:

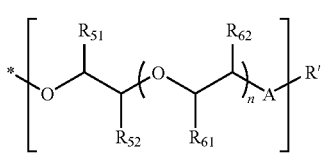

wherein n is 0 or a positive integer; wherein $R_{51}$, $R_{52}$, $R_{61}$, and $R_{62}$ are, independently, H or alkyl; wherein A is O, S, or amino; and wherein R' comprises a peptide.

Also disclosed are pharmaceutical compositions comprising one or more of the disclosed compounds or pharmaceutically acceptable salts or prodrugs thereof, and one or more pharmaceutically acceptable carriers.

Also disclosed are methods for the treatment of a disease of uncontrolled cellular proliferation comprising administering to a mammal diagnosed as having a disease of uncontrolled cellular proliferation one or more of the disclosed compounds, one or more of the disclosed nanoparticles, one or more of the disclosed a multifunctional delivery vehicles, one or more of the disclosed pharmaceutical compositions, or pharmaceutically acceptable salts or prodrugs thereof, in an amount effective to treat the disease of uncontrolled cellular proliferation.

Also disclosed are compounds comprising the structure:

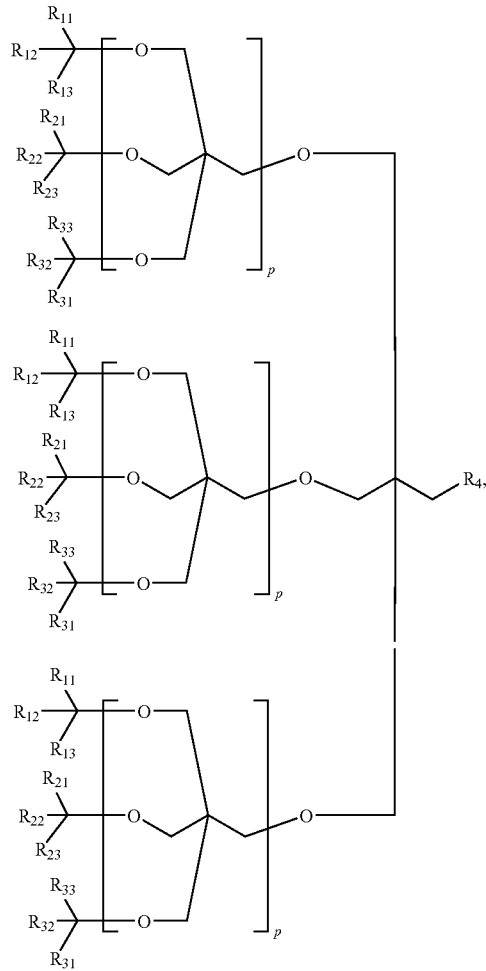

wherein p is a non-negative integer; wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$ or alkyl; and wherein $R_4$ comprises the structure:

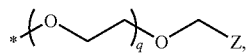

wherein q is a non-negative integer, and wherein Z comprises $CH_2OH$, $CH_2NH_2$, $CH_2SH$, $CO_2H$, $CH_2O(CH_2CH_2O)_4H$, or a substituted or unsubstituted amide.

Also disclosed are compounds wherein the substituted or unsubstituted amide comprises the structure:

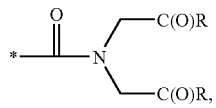

wherein R is OH, $NH_2$, NH-alkyl, alkyl, polyalkylene oxide, a moiety having the structure:

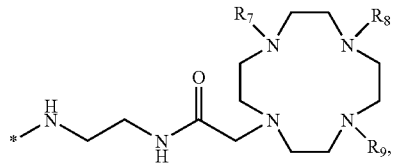

or a moiety having the structure:

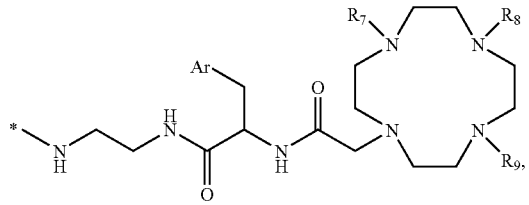

wherein $R_7$, $R_9$, and $R_9$ are, independently, H, $CH_2CO_2H$, or alkyl, and wherein Ar is an aryl group.

Also disclosed are compounds wherein the substituted or unsubstituted amide comprises the structure:

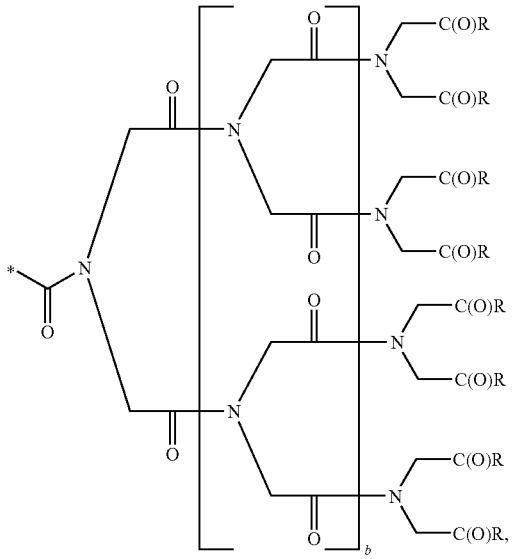

wherein b is a non-negative integer, and wherein R is OH, NH$_2$, NH-alkyl, alkyl, polyalkylene oxide, a moiety having the structure:

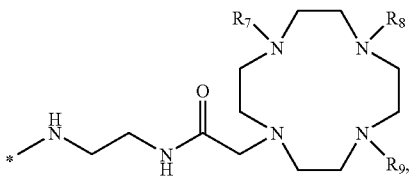

or a moiety having the structure:

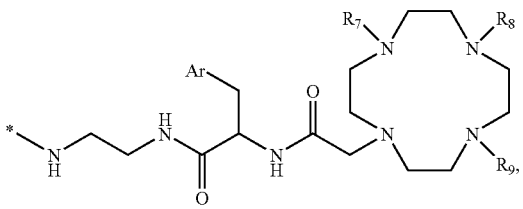

wherein R$_7$, R$_8$, and R$_9$ are, independently, H, CH$_2$CO$_2$H, or alkyl, and wherein Ar is an aryl group.

Also disclosed are bilayers, micelles, (micro)emulsions, and nanoparticles comprising the disclosed compounds.

Also disclosed are multifunctional delivery vehicles comprising at least one the disclosed compounds comprising a moiety having the structure:

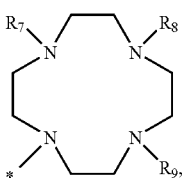

wherein R$_7$, R$_8$, and R$_9$ are, independently, H, CH$_2$CO$_2$H, or alkyl.

Also disclosed are methods of delivering radionuclides for radiotherapy comprising the steps of complexing a radionuclide with a disclosed compound comprising a moiety having the structure:

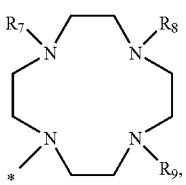

wherein R$_7$, R$_8$, and R$_9$ are, independently, H, CH$_2$CO$_2$H, or alkyl; and administering the complex to a mammal in an amount effective for radiotherapy.

Also disclosed are methods of delivering a metallic ion for $^1$H imaging comprising the steps of complexing a metal ion with a disclosed compound comprising a moiety having the structure:

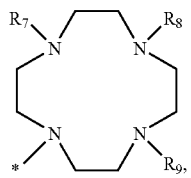

wherein R$_7$, R$_8$, and R$_9$ are, independently, H, CH$_2$CO$_2$H, or alkyl; and administering the complex to a subject in an amount effective for detection by $^1$H MRI.

Also disclosed are compounds comprising the structure: R$_\phi$–R$_\psi$; wherein R$_\phi$ comprises a branched hydrophobic moiety comprising hydrocarbon, perfluorocarbon, partial fluorocarbon, or a hybrid analogue with O, S, N, B, Si, or P, wherein each multivalent atom in R$_\phi$ has a valency, v, and is unbranched or substituted with v-1 identical substituents, wherein R$_\phi$ has at least one branching point other than a t-butyl or perfluoro-t-butyl group, wherein the branching point is a multivalent atom having a valency, v, of greater than or equal to 3, and wherein the branching point is substituted with v-1 identical substituents, and wherein the branching point identical substituents each comprise at least one multivalent atom; and wherein R$_\psi$ comprises an unbranched hydrophilic moiety having the structure: (CH$_2$)$_i$[Y(CH$_2$)$_j$]$_k$Z, wherein i, j, and k are, independently, non-negative integers, wherein Y is O, S, or NH, and wherein Z is OH, SH, CO$_2$H, SO$_3$H, OP(O)(OH)$_2$, silyl, a primary amine, a secondary amine, a tertiary amine, a quaternary ammonium salt, an amino acid, a peptide, a sugar, an (oligo)nucleotide, or a chelator.

Also disclosed are compounds comprising the structure: R$_\phi$–R$_\psi$; wherein R$_\phi$ comprises a branched hydrophobic moiety comprising hydrocarbon, perfluorocarbon, partial fluorocarbon, or a hybrid analogue with O, S, N, B, Si, or P, wherein each multivalent atom in R$_\phi$ has a valency, v, and is unbranched or substituted with v-1 identical substituents, wherein R$_\phi$ has at least one branching point other than a t-butyl or perfluoro-t-butyl group, wherein the branching point is a multivalent atom having a valency, v, of greater than or equal to 3, and wherein the branching point is substituted with v-1 identical substituents, and wherein the branching point identical substituents each comprise at least one multivalent atom; and wherein R$_\psi$ comprises a branched or unbranched hydrophilic moiety comprising OH, a primary amine, a secondary amine, a tertiary amine, a quaternary ammonium salt, substituted or unsubstituted alkyl, or substituted or unsubstituted alkoxy.

Also disclosed are methods of delivering radionuclides for radiotherapy comprising the steps of complexing a radionuclide with at least one of the disclosed compound; and administering the complex to a mammal in an amount effective for radiotherapy.

Also disclosed are methods of delivering a metallic ion for $^1$H imaging comprising the steps of complexing a metal ion with at least one of the disclosed compounds; and administering the complex to a subject in an amount effective for detection by $^1$H MRI.

Also disclosed are methods of delivering a fluorocarbon for $^{19}$F imaging comprising the steps of administering at least one of the disclosed compounds to a subject in an amount effective for detection by $^{19}$F MRI; and performing a $^{19}$F MRI experiment of the subject.

Also disclosed are methods of delivering oxygen comprising the steps of complexing oxygen with at least one of the disclosed compounds; and administering the complex to a subject.

Also disclosed are multi-modular treatment methods comprising the step of simultaneously performing at least two of the disclosed methods.

Additional advantages can be set forth in part in the description which follows, and in part can be obvious from the description, or may be learned by practice. Other advantages can be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several embodiments and together with the description serve to explain the principles of the invention.

FIG. 4 shows the $^{19}$F NMR spectra of fluorocarbon nanoparticles for one representative spectrum. a. Emulsion formulated by us on a 200 ppm scale. b. The same $^{19}$F spectrum on a 1 ppm scale. The F-oil and the F-surfactant peaks are very close (0.25 ppm apart); c. $^{19}$F spectrum of fluorocarbon nanoparticles in one published study $^{19}$F, also on a 200 ppm scale. The F-oil used is an analog of compound 4 with —OBn replaced by -Me, while the F-surfactant is compound 10.

Figure 1:
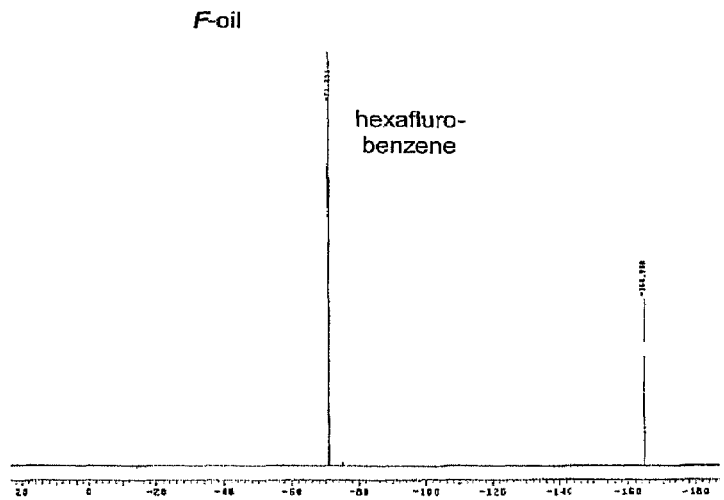
FIG. 1 shows the $^{19}$F NMR spectrum of an F-oil (compound 5). The signal around 71 ppm is from the F-oil and the signal around 164 ppm is from the standard, hexafluorobenzene.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

A. DEFINITIONS

As used in the specification and the appended claims, the singular forms "a," "an" and "the" include plural referents unless the context clearly dictates otherwise. Thus, for example, reference to "a compound," "a polymer," or "a particle" includes mixtures of two or more such compounds, polymers, or particles, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it can be understood that the particular value forms another embodiment. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. Unless explicitly disclosed, this disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "alkyl" refers to a hydrocarbon group that can be conceptually formed from an alkane, alkene, or alkyne by removing hydrogen from the structure of a cyclic or non-cyclic hydrocarbon compound having straight or branched carbon chains, and replacing the hydrogen atom with another atom or organic or inorganic substituent group. In some aspects of the invention, the alkyl groups are "$C_1$ to $C_6$ alkyl" such as methyl, ethyl, propyl, isopropyl, n-butyl, iso-butyl, sec-butyl, tert-butyl, amyl, tert-amyl, and hexyl groups, their alkenyl analogues, their alkynyl analogues, and the like. Many embodiments of the invention comprise "$C_1$ to $C_4$ alkyl" groups (alternatively termed "lower alkyl" groups) that include methyl, ethyl, propyl, iso-propyl n-butyl, iso-butyl, sec-butyl, and t-butyl groups, their alkenyl analogues, their alkynyl analogues, or the like. Some of the preferred alkyl groups of the invention have three or more carbon atoms preferably 3 to 16 carbon atoms, 4 to 14 carbon atoms, or 6 to 12 carbon atoms. The alkyl group can be unsubstituted or substituted. A hydrocarbon residue, for example an alkyl group, when described as "substituted," contains or is substituted with one or more independently selected heteroatoms such as O, S, N, P, or the halogens (fluorine, chlorine, bromine, and iodine), or one or more substituent groups containing heteroatoms (OH, $NH_2$, $NO_2$, $SO_3H$, and the like) over and above the carbon and hydrogen atoms of the substituent residue. Substituted hydrocarbon residues may also contain carbonyl groups, amino groups, hydroxyl groups and the like, or contain heteroatoms inserted into the "backbone" of the hydrocarbon residue. In one aspect, an "alkyl" group can be fluorine substituted. In a further aspect, an "alkyl" group can be perfluorinated.

In certain aspects, the term "alkyl" as used herein is a branched or unbranched saturated hydrocarbon group of 1 to 24 carbon atoms, for example 1 to 12 carbon atoms or 1 to 6 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a", is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^1A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —$OC(O)A^1$ or —$C(O)OA^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C$-$A^2$-$C(O)O)_a$— or -$(A^1O(O)C$-$A^2$-$OC(O))_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula $-A^1O-A^2O)_a-$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine. It is also understood that, in certain aspects, pseudohalides (e.g., tosyl or mesyl groups) can be substituted for halo groups.

The term "hydroxyl" as used herein is represented by the formula —OH.

The term "ketone" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula $—N_3$.

The term "nitro" as used herein is represented by the formula $—NO_2$.

The term "nitrile" as used herein is represented by the formula —CN.

The term "silyl" as used herein is represented by the formula $—SiA^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A'$, or $—OS(O)_2OA^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $—S(O)_2A'$, where $A^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Disclosed are the components to be used to prepare the compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. SYMBOLS AND ABBREVIATIONS

Bn: benzyl; Boc: t-butoxycarbonyl; Bz: benzoyl; CEST: chemical exchange saturation transfer; Cys: cysteine; DCC: 1,3-dicylclohexylcarbodiimide; DCM: dichloromethane; DEAD: diethylazodicarboxylate; DMAP: 4-dimethylaminopyridine; DOTA: 1,4,7,10-tetraazacyclododecane-1,4,7,10-tetraacetate; EYP: egg yolk phospholipids; Fmoc: fluorenylmethoxycarbonyl; F-oil: fluorinated oils; F-surfactant: fluorinated surfactants; HPLC: high-performance liquid chromatography; ICP-OES: Inductively coupled plasma optical emission spectrometry; LC: liquid chromatography; Lys (K): lysine; MRI: magnetic resonance imaging; MRS: magnetic resonance spectroscopy; MS: mass spectrometry; Ms: methanesulfonyl; NMR: nuclear magnetic resonance; o/w: oil-in-water; PBS: physiological buffer systems; Phe: phenylalanine; $pO_2$: oxygen partial pressure (also called oxygen tension); SAXS: small-angle X-ray scattering; TBAF: tetra-butylammonium fluoride; TBS: t-butyldimethylsilyl; tBu: t-butyl; TFA: trifluoroacetic acid; THF: tetrahydrofuran; Thr: threonine: Trp: tryptophan; and Tyr: tyrosine.

C. TABLE OF COMPOUNDS
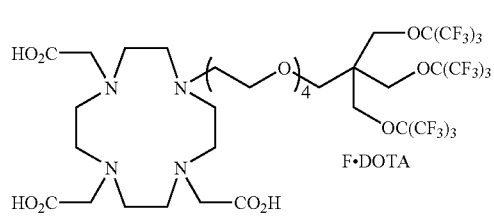
1 F·DOTA
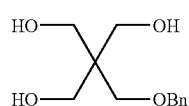
2
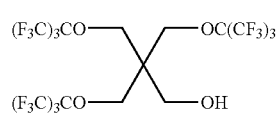
3
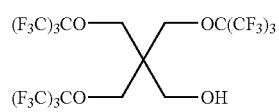
4
5
HO(CH₂CH₂O)₄H    6
TBDMSO(CH₂CH₂O)₄H    7
TBDMSO(CH₂CH₂O)₃CH₂CH₂OMs    8
BnO(CH₂CH₂O)₄H    7'
BnO(CH₂CH₂O)₄Ms    8'
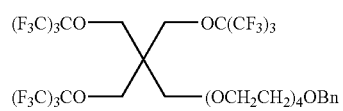
9
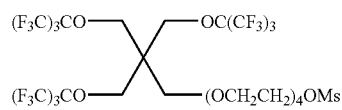
10
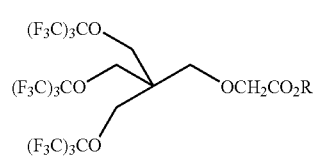
11
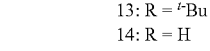
12
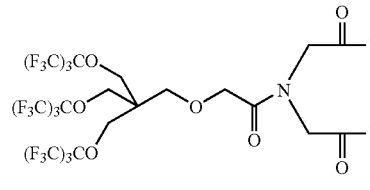
13: R = $^t$Bu
14: R = H
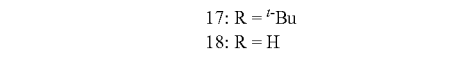
15: R = $^t$Bu
16: R = H
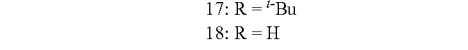
17: R = $^t$Bu
18: R = H
19: R = $^t$Bu
20: R = H -continued
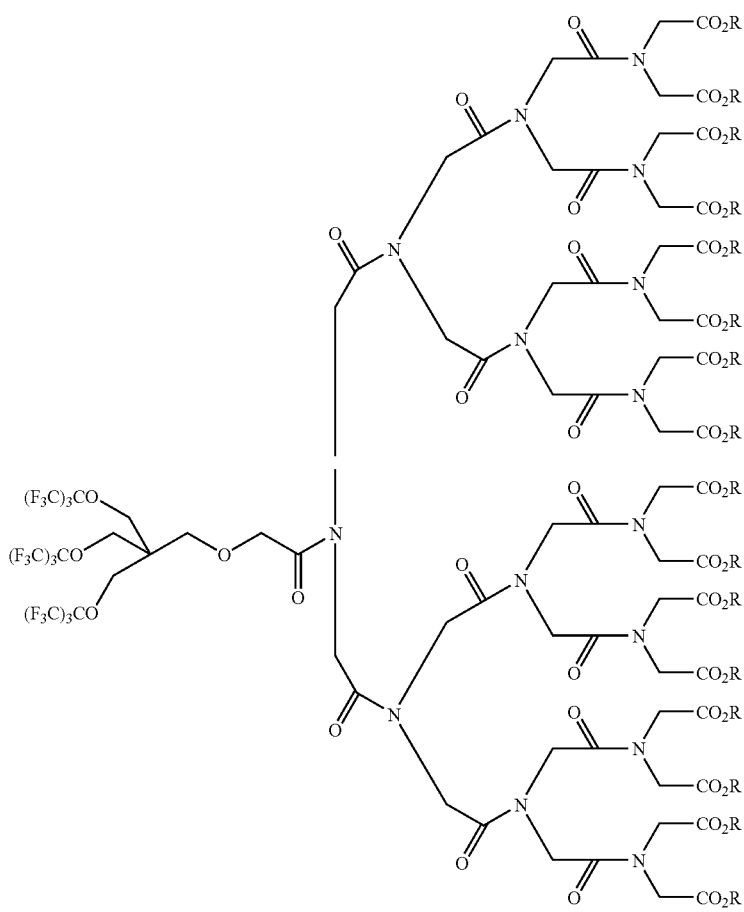
21: R = <sup>t</sup>Bu
22: R = H
 23
 24
 25
 26 (G0)
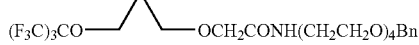 27
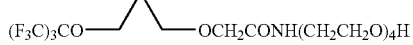 28 (G1)
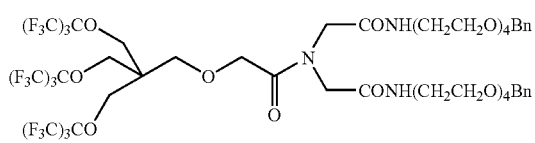
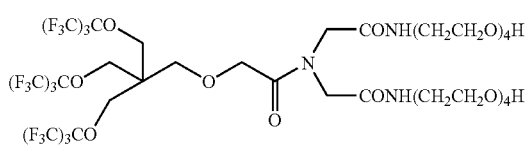
29
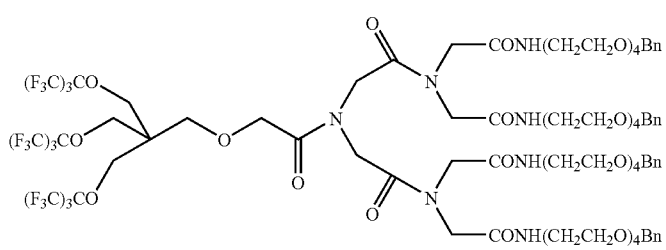

30 (G2)
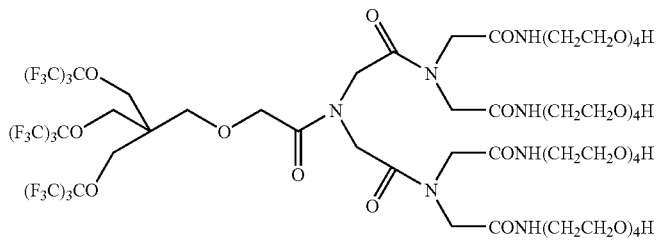
31
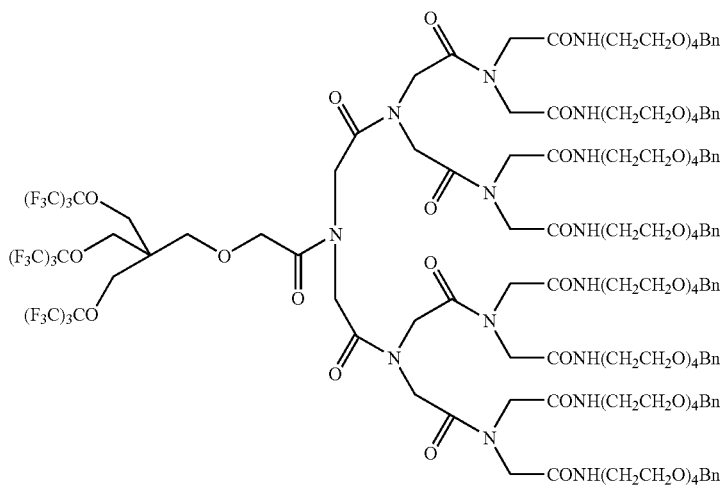
32 (G3)
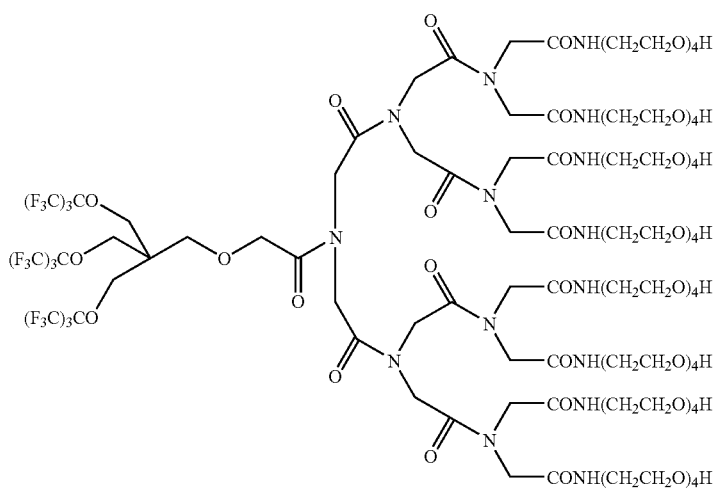

-continued
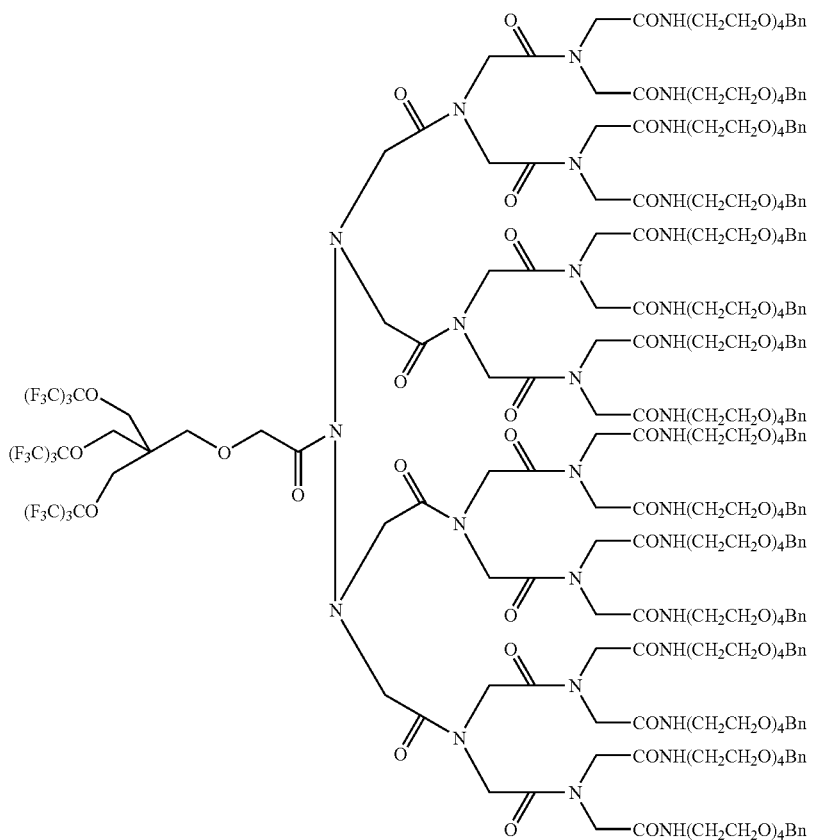
33
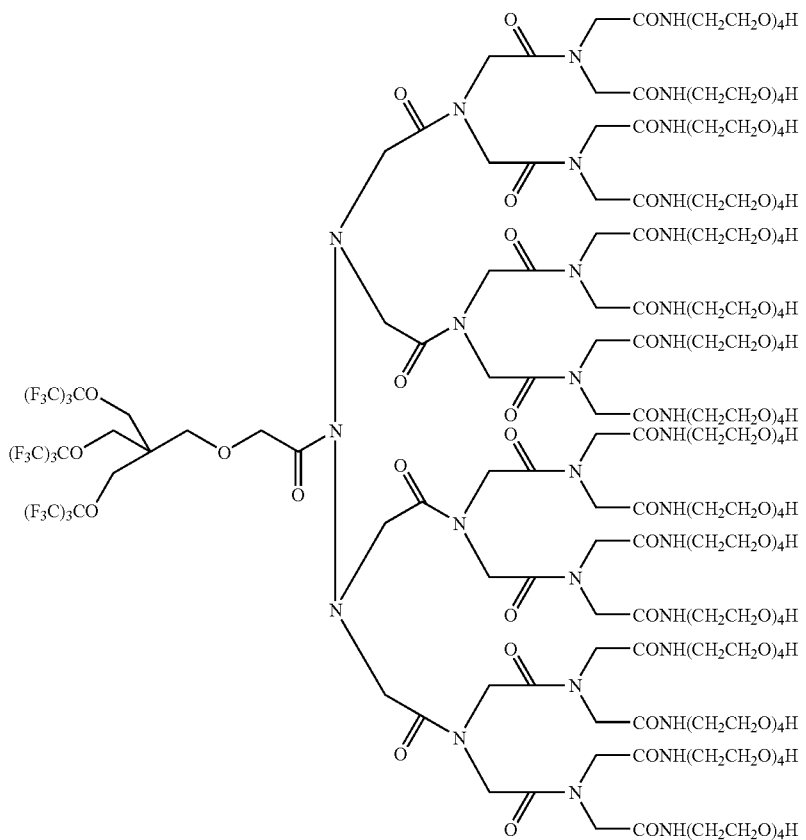
34 (G4)

| 25 | 26 |
|---|---|
| | -continued |
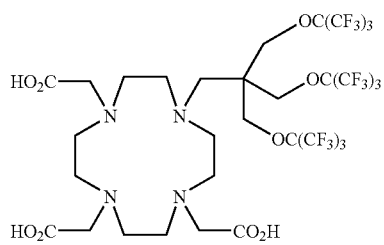  25
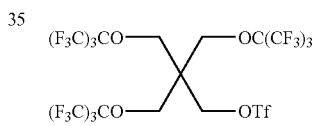  36
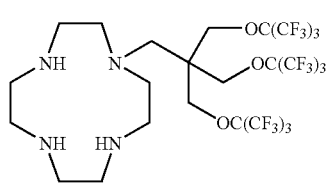  37
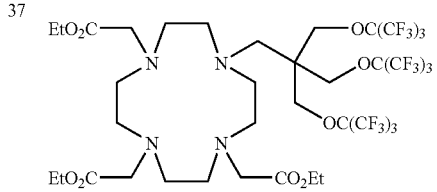  38
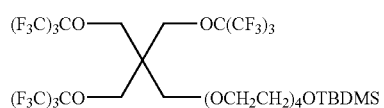  39
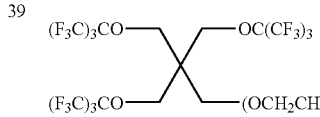  40
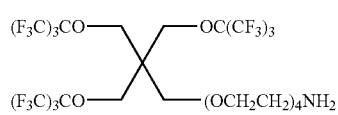  41
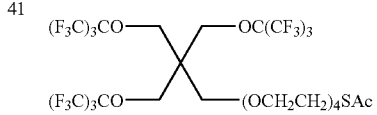  42
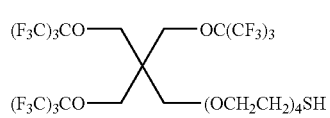  43
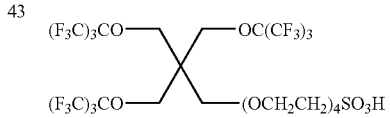  44
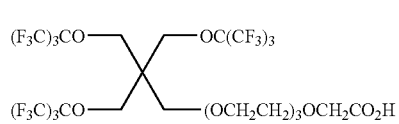  45
HN(CH$_2$CH$_2$OH)$_2$    46
Bn(OCH$_2$CH$_2$)$_4$N(CH$_2$CH$_2$OH)$_2$   47
Bn(OCH$_2$CH$_2$)$_4$N(CH$_2$CH$_2$OC(CF$_3$)$_3$)$_2$   48
((CF$_3$)$_3$COCH$_2$CH$_2$)$_2$N(CH$_2$CH$_2$O)$_4$H    49
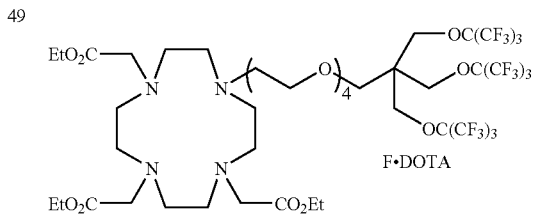  50

D. HIGHLY FLUORINATED COMPOUNDS

In one aspect, the compounds are highly fluorinated compounds. In a further aspect, the compounds are partially fluorinated compounds. In an even further aspect, the compounds are non-fluorinated, yet hydrophobic, compounds.

1. Structure

In one aspect, a compound comprises the structure:

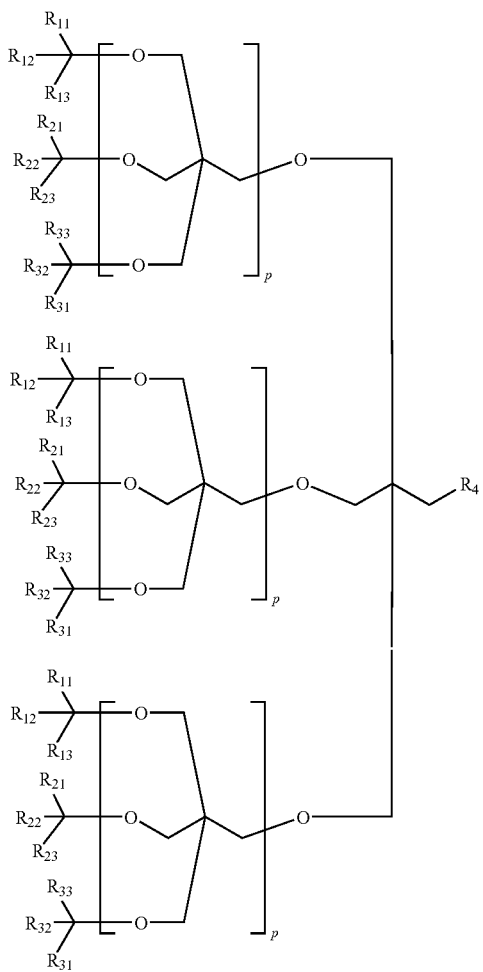

wherein p is a non-negative integer; wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$, or alkyl; and wherein $R_4$ is H, OH, OBn, $OC(CF_3)_3$, alkyl, or alkoxy. In a further aspect, p is 2, 3, 4, or 5. In one aspect, at least one of $R_{11}$, $R_{12}$, $R_{13}$, $R_{21}$, $R_{22}$, $R_{23}$, $R_{31}$, $R_{32}$, or $R_{33}$ is $CF_3$. In a further aspect, $R_{11}$, $R_{12}$, $R_{13}$, $R_{21}$, $R_{22}$, $R_{23}$, $R_{31}$, $R_{32}$, and $R_{33}$ are $CF_3$.

In a yet further aspect, a compound comprises the structure:

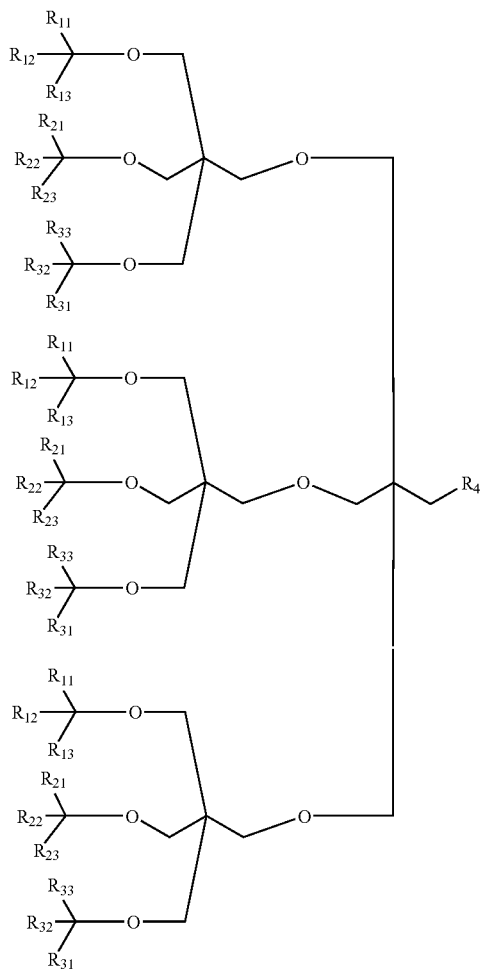

wherein p is a non-negative integer; wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$, or alkyl; and wherein $R_4$ is H, OH, OBn, $OC(CF_3)_3$, alkyl, or alkoxy. In one aspect, at least one of $R_{11}$, $R_{12}$, $R_{13}$, $R_{21}$, $R_{22}$, $R_{23}$, $R_{31}$, $R_{32}$, or $R_{33}$ is $CF_3$. In a further aspect, $R_{11}$, $R_{12}$, $R_{13}$, $R_{21}$, $R_{22}$, $R_{23}$, $R_{31}$, $R_{32}$, and $R_{33}$ are $CF_3$.

In a further aspect, a compound comprises the structure:

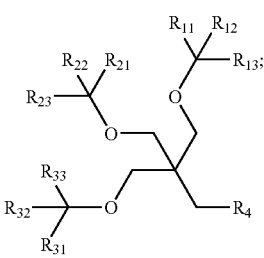

wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$, or alkyl; and wherein $R_4$ is H, OH, OBn, $OC(CF_3)_3$, alkyl, or alkoxy. In a further aspect, $R_{11}$, $R_{12}$, and $R_{13}$ are $CF_3$. In a further aspect, $R_{21}$, $R_{22}$, and $R_{23}$ are $CF_3$. In a further aspect, $R_{31}$, $R_{32}$, and $R_{33}$ are $CF_3$. In one aspect, at least one of $R_{11}$, $R_{12}$, $R_{13}$, $R_{21}$, $R_{22}$, $R_{23}$, $R_{31}$, $R_{32}$, or $R_{33}$ is $CF_3$. In a further aspect, $R_{11}$, $R_{12}$, $R_{13}$, $R_{21}$, $R_{22}$, $R_{23}$, $R_{31}$, $R_{32}$, and $R_{33}$ are $CF_3$.

In one aspect, the compound is a surfactant. In a further aspect, the compound comprises a structure:

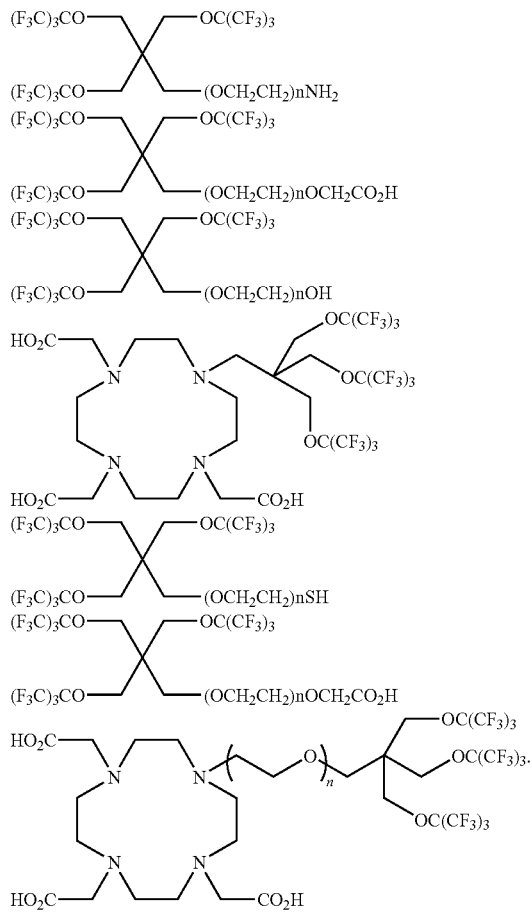

In a further aspect, the compound exhibits maximum symmetric branching.

In one aspect, the compound is an oil. In a further aspect, the compound comprises a structure:

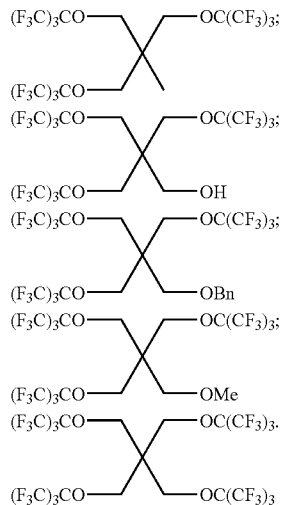

In a further aspect, the compound exhibits maximum symmetric branching.

In one aspect, $R_4$ comprises the structure:

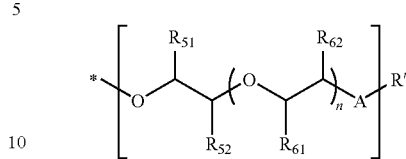

wherein n is 0 or a positive integer; wherein $R_{51}$, $R_{52}$, $R_{61}$, and $R_{62}$ are, independently, H or alkyl; wherein A is O, S, or amino; and wherein R' comprises H, $CH_2CO_2H$, silyl, alkyl, or a peptide.

In a further aspect, $R_4$ comprises the structure:

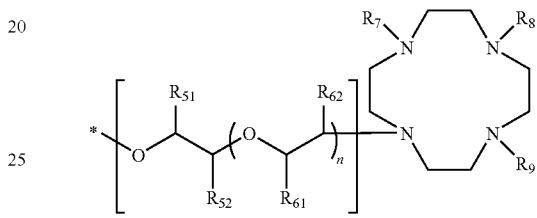

wherein n is 0 or a positive integer; wherein $R_{51}$, $R_{52}$, $R_{61}$, and $R_{62}$ are, independently, H or alkyl; and wherein $R_7$, $R_8$, and $R_9$ are, independently, H, $CH_2CO_2H$, or alkyl.

In one aspect, a compound comprises a hydrophilic moiety and a hydrophobic moiety, wherein the hydrophobic moiety exhibits maximum symmetric branching.

In one aspect, a compound comprises the structure:

$$R_\phi-R_\psi;$$

wherein $R_\phi$ comprises a branched hydrophobic moiety comprising hydrocarbon, perfluorocarbon, partial fluorocarbon, or a hybrid analogue with O, S, N, B, Si, or P, wherein each multivalent atom in $R_\phi$ has a valency, v, and is branched or unbranched, wherein $R_\phi$ has at least one branching point other than a t-butyl or perfluoro-t-butyl group, wherein the branching point is a multivalent atom having a valency, v, of greater than or equal to 3, and wherein the branching point is substituted with v-1 or v-2 identical substituents if v=4 or substituted with v-1 identical substituents if v=3, and wherein the branching point identical substituents each comprise at least one multivalent atom; and wherein $R_\psi$ comprises an unbranched hydrophilic moiety having the structure:

$$(CH_2)_i[Y(CH_2)_j]_kZ,$$

wherein i, j, and k are, independently, non-negative integers, wherein Y is O, S, or NH, and wherein Z is OH, SH, $CO_2H$, $SO_3H$, $OP(O)(OH)_2$, silyl, a primary amine, a secondary amine, a tertiary amine, a quaternary ammonium salt, an amino acid, a peptide, a sugar, an (oligo)nucleotide, or a chelator. The compound can be a surfactant.

In a further aspect, a compound comprises the structure:

$$R_\phi-R_\psi;$$

wherein $R_\phi$ comprises a branched hydrophobic moiety comprising hydrocarbon, perfluorocarbon, partial fluorocarbon, or a hybrid analogue with O, S, N, B, Si, or P, wherein each multivalent atom in $R_\phi$ has a valency, v, and is branched or unbranched, wherein $R_\phi$ has at least one branching point other than a t-butyl or perfluoro-t-butyl group, wherein the branching point is a multivalent atom having a valency, v, of greater than or equal to 3, and wherein the branching point is substituted with v-1 identical substituents, and wherein the branching point identical substituents each comprise at least one multivalent atom; and wherein $R_\phi$ comprises a branched or unbranched hydrophilic moiety comprising OH, a primary amine, a secondary amine, a tertiary amine, a quaternary ammonium salt, substituted or unsubstituted alkyl, or substituted or unsubstituted alkoxy. The compound can be an oil.

In one aspect, a compound comprises the structure:

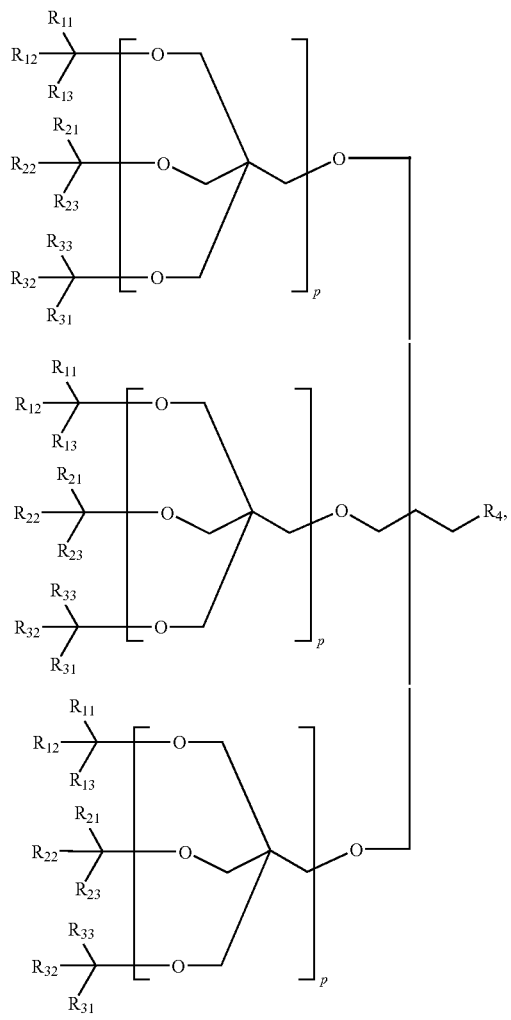

wherein p is a non-negative integer; wherein $R_{11}$, $R_{12}$, $R_{13}$, $R_{21}$, $R_{22}$, $R_{23}$, $R_{31}$, $R_{32}$, and $R_{33}$ are, independently, H, $CH_3$, $CF_3$ or alkyl; and wherein $R_4$ comprises the structure:

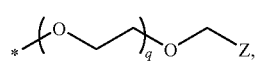

wherein q is a non-negative integer, and wherein Z comprises $CH_2OH$, $CH_2NH_2$, $CH_2SH$, $CO_2H$, $CH_2$—O—$(CH_2CH_2O)_j$H, or a substituted or unsubstituted amide, wherein j is a positive integer. In a further aspect, p and q are, independently, 2, 3, 4, or 5. In a further aspect, $R_{11}$, $R_{12}$, $R_{13}$, $R_{21}$, $R_{22}$, $R_{23}$, $R_{31}$, $R_{32}$, and $R_{33}$ are $CF_3$. In a further aspect, p is 0 and the compound comprises the structure:

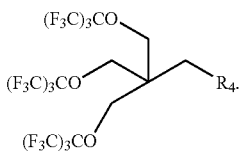

In a further aspect, $R_4$ comprises the structure:

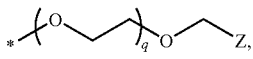

wherein q is a non-negative integer, and wherein Z comprises $CH_2OH$, $CH_2NH_2$, $CH_2SH$, $CO_2H$, or $CH_2$—O—$(CH_2CH_2O)_4H$. In a yet further aspect, Z comprises $CH_2OH$, $CH_2NH_2$, $CH_2SH$, $CO_2H$, or $CH_2$—O—$(CH_2CH_2O)_4H$. In a further aspect, q is 3.

In a further aspect, $R_4$ comprises the structure:

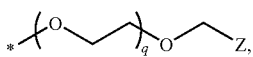

wherein q is a non-negative integer, and wherein Z comprises a substituted or unsubstituted amide.

In one aspect, the substituted or unsubstituted amide comprises the structure:

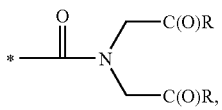

wherein R is OH, $NH_2$, NH-alkyl, alkyl, polyalkylene oxide, a moiety having the structure:

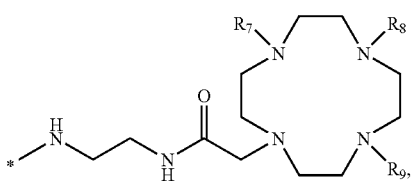

or a moiety having the structure:

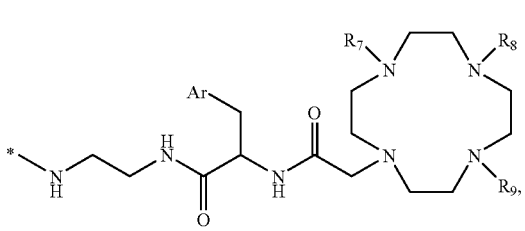

wherein $R_7$, $R_8$, and $R_9$ are, independently, H, $CH_2CO_2H$, or alkyl, and wherein Ar is an aryl group.

In a further aspect, R comprises the structure:

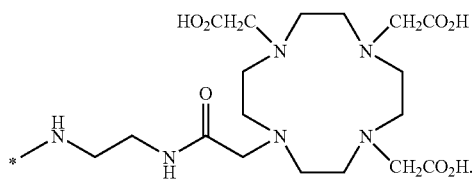

In a further aspect, R comprises the structure:

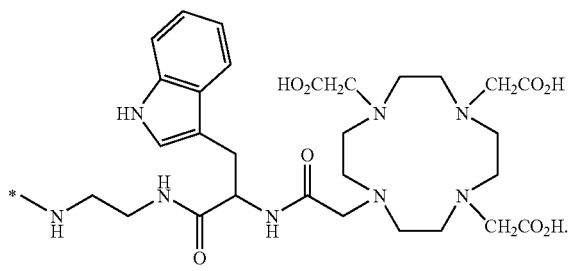

In one aspect, the substituted or unsubstituted amide comprises the structure:

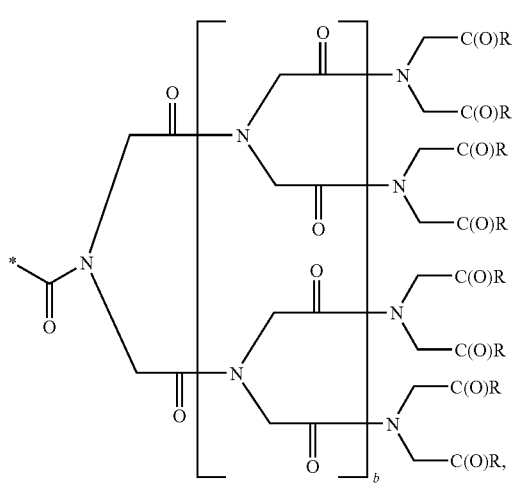

wherein b is a non-negative integer, and wherein R is OH, $NH_2$, NH-alkyl, alkyl, polyalkylene oxide, a moiety having the structure:

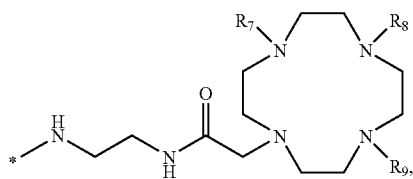

or a moiety having the structure:

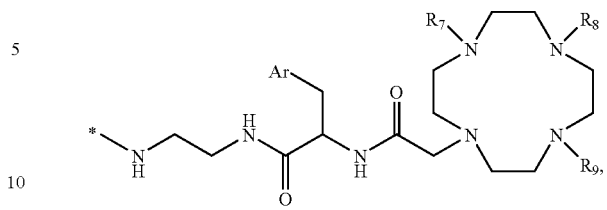

wherein $R_7$, $R_8$, and $R_9$ are, independently, H, $CH_2CO_2H$, or alkyl, and wherein Ar is an aryl group. In a further aspect, b is 0, 1, 2, or 3.

In one aspect, R comprises the structure:

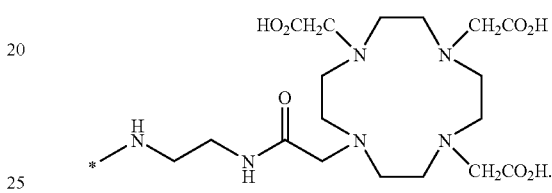

In a further aspect, R comprises the structure:

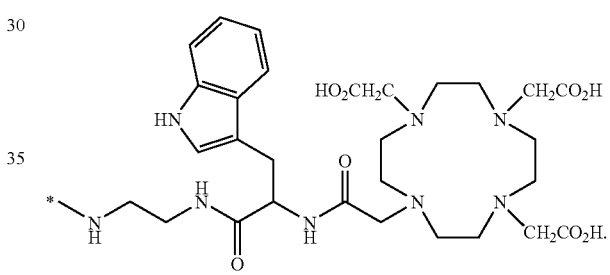

a. Chelator

The macrocyclic chelator DOTA (1,4,7,10-tetraazacyclododecane-1,4,7,10-tetraacetate), for example, can be used as the metallic ion carrier in the present compounds because ion-DOTA complexes have thermodynamic and kinetic stability [Bianchi, et al., Thermodynamic and structural properties of Gd(III) complexes with polyamino-polycarboxylic ligands: basic compounds for the development of MRI contrast agents. Coord. Chem. Rev. 204, 309-393, 2000]. DOTA is the chelator used in the radio-therapeutic drug OctreoTher® for $^{90}Y^{3+}$ complexation and the MRI contrast agent Dotarem® for $Gd^{3+}$ complexation. Analogs of DOTA or other chelators (e.g., DTPA) can also be used.

b. Targeting Peptide

Octreotide can be used, for example, as the targeting for the present compounds. Octreotide is an octapeptide analog of the natural hormone somatostatin and has been approved for treating acromegaly (Sandostatin®). It is also the targeting peptide used in the radiodiagnostic agent OctreoScan® (FDA-approved) and radiotherapeutic agent OctreoTher® (under clinical trials). Hence it has a proven record for clinical use. It targets neuroendocrine tumors that over-express type 2 stamotostatin receptors ($sstr_2$) [Kaltsas, G. A., Papadogias, D., Makras, P. & Grossman, A. B. Treatment of advanced neuroendocrine tumours with radiolabelled somatostatin analogues. Endocrine-Related Cancer, 12, 683-699, 2005].

Other analogs of octreotide (such as, but not restricted to, lanreotide, vapreotide, etc.) can be used for this purpose as well. Other peptides (such as, but not restricted to, bombesin, vasoactive intestinal peptide, cholecystokinin, substance P, etc.) can also be used for this purpose (L. Bodei, G. Paganelli & G. Mariani, Receptor radionuclide therapy of tumors: a road from basic research to clinical applications. J. Nucl. Med. 47, 375-377, 2006).

2. Maximum Symmetric Branching

In one aspect, each compound can have a hydrophilic moiety and a hydrophobic moiety. The hydrophilic moiety can be an unbranched chain of variable length and with different terminal groups. The chemical nature of the hydrophilic chain can be variable (e.g., oxyethylene units, oxypropylene units, etc.). In one aspect, the hydrophobic moiety is branched and satisfies the principle of "maximum symmetric branching." In a one aspect, at any point in the hydrophobic moiety, there is either no branching (i.e., —$CH_2$—, —$CF_2$—, —NH—, —BH—, —O—, —S—) or has maximum number of branches with all branches identical (e.g., a carbon or a silicon should have three identical branches and a nitrogen or a boron should have two identical branches). The hydrophobic moiety can contain at least one branching point. A terminal perfluoro-tert-butyl group is typically not counted as a branching point.

In one aspect, every branch point can be symmetric and at least one branching point is maximally symmetric, with the stipulation that terminal tert-butyl or perfluoro-tert-butyl cannot be the sole maximally symmetric branching point in a molecule.

In a sense, this describes a chain growth mechanism for the surfactant or oil molecule. The resultant surfactant or oil molecules can be "umbrella-shaped" with the hydrophilic and the hydrophobic moieties being the "pole" and the canopy of the "umbrella," respectively. As a result of symmetric branching, terminal groups in the hydrophobic moiety have, in one aspect, perfect spherical symmetry, leading to a single $^{19}F$ signal for magnetic resonance detection. As a result of maximum branching, the surfactant has, in one aspect, maximum terminal surface area for a given number of main-chain atoms. This gives the best surface protection if these surfactants are used as, for example, coating materials.

3. Surfactants

In one aspect, the compounds are surfactants having a hydrophobic moiety and a hydrophilic moiety. Exemplary surfactants include the following structures.

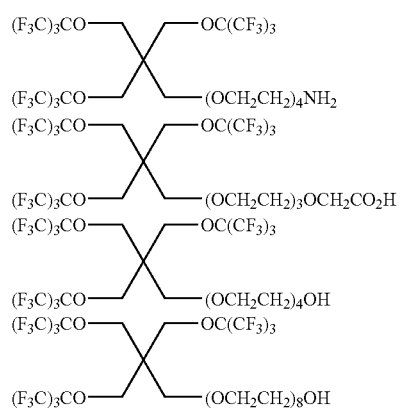

-continued

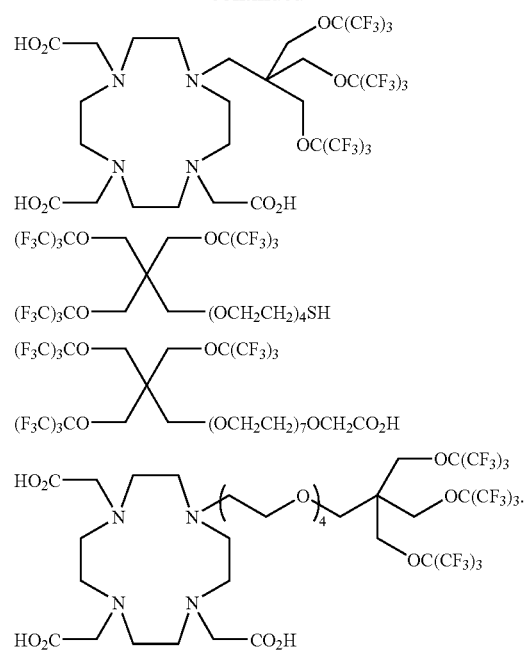

4. Oils

In one aspect, the compounds are oils having at least one hydrophobic moiety. Exemplary oils include the following structures.

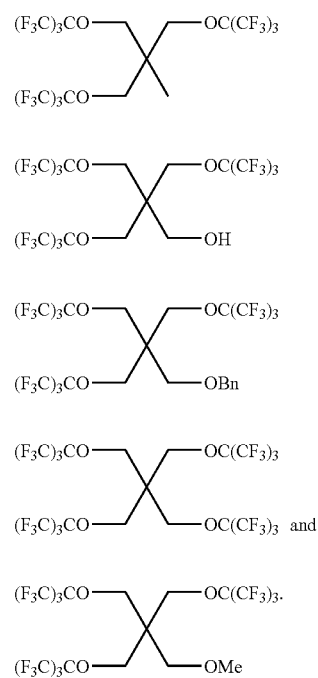

E. METHODS OF PREPARATION

In one aspect, the methods relate to a process for the preparation of a compound comprising the structure:

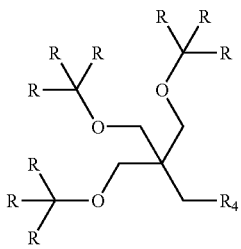

wherein R is H, CH$_3$, CF$_3$, or alkyl and wherein R$_4$ is H, OH, OBn, alkyl, or alkoxy; the process comprising the steps of: providing a triol, reacting the triol with tert-butanol or nonafluoro-tert-butanol to provide a tri-tert-butyl ether or a triperfluoro-tert-butyl ether. In a further aspect, the reacting step is performed with nonafluoro-tert-butanol. In a further aspect, the triol is pentaerythritol, mono-silylated pentaerythritol, or 2,2-bis-hydroxymethyl-propan-1-ol. In one aspect, R$_4$ comprises methyl, ethyl, n-propyl, isopropyl, or butyl. In one aspect, R is CF$_3$.

In one aspect, the providing step is performed by the steps of: mono-protecting pentaerythritol before the reacting step, and deprotecting the product of the reacting step. In a further aspect, the reacting step occurs before the deprotecting step. In a further aspect, the process can further comprise the step of coupling the product the deprotecting step with a hydrophilic compound.

In one aspect, the hydrophilic compound comprises a moiety having the structure:

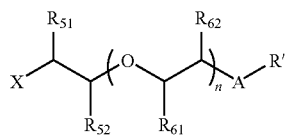

wherein n is 0 or a positive integer; wherein R$_{51}$, R$_{52}$, R$_{61}$, and R$_{62}$ are, independently, H or alkyl; wherein R' comprises H, CH$_2$CO$_2$H, silyl, or alkyl; wherein A is O, S, or amino; and wherein X is a leaving group. In one aspect, n is an integer from 4 to 12. In a further aspect, the process further comprises the step of cleaving the silyl group. In a further aspect, the process further comprises the step of conjugating with cyclen or a compound comprising a cyclen residue.

In a further aspect, the compound comprises the structure:

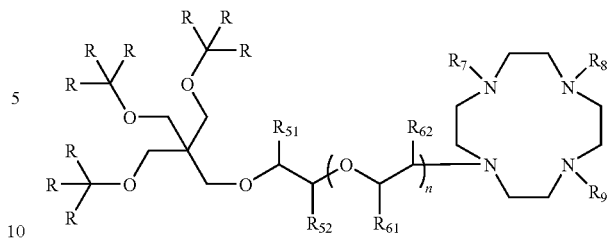

wherein n is 0 or a positive integer; wherein R$_{51}$, R$_{52}$, R$_{61}$, and R$_{62}$ are, independently, H or alkyl; and wherein R$_7$, R$_8$, and R$_9$ are, independently, H, CH$_2$CO$_2$H, or alkyl. In a further aspect, R is CF$_3$. In a further aspect, n is an integer from 4 to 12.

In one aspect, the compounds and compositions relate to the product(s) produced by the process(es) of the methods.

One example highly fluorinated compound, 1 F-DOTA, was prepared by the methods disclosed herein:

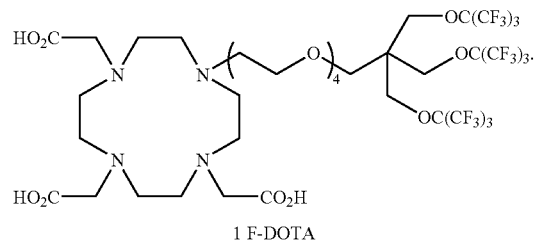

1 F-DOTA

The synthesis of 1 F-DOTA started with the modification of pentaerythritol. Protection pentaerythritol 2 as the orthoacetate, followed by protection of the fourth hydroxyl group with benzyl bromide and hydrolysis of the orthoacetate, furnished the corresponding triol 3 [Dunn, T. J.; Neumann, W. L.; Rogic, M. M.; Woulfe, S. R. *J. Org. Chem.* 1990, 55, 6368-6373.]. Then, triol 3 was reacted with nonafluoro-tert-butanol in the presence of diethylazodicarboxylate, triphenylphosphine and powdered 4 Å molecular sieve to provide the perfluoro-tert-butyl ether 4 in one step with good yield. Tri-perfluoro-tert-butyl ether 4 was isolated from the reaction mixture by simple F362 extraction, and no mono- or di-perfluoro-tert-butyl ether was detected from the extract. Lewis acid (aluminum chloride) mediated removal of the benzyl ether completed construction of the desired highly fluorinated alcohol 5 in substantially quantitative yield on 50 gram scale.

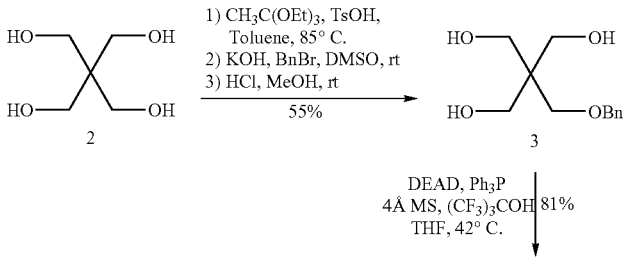

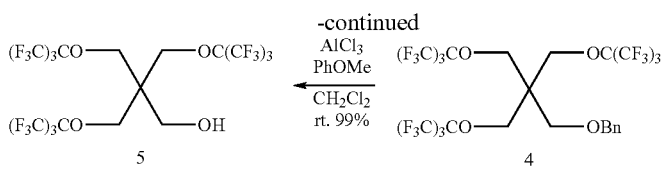

To prepare the linker 8, one of the hydroxyl groups in the tetraethylene glycol 6 was selectively protected as tert-butyldimethylsilyl ether 7, which was then treated with methanesulfonyl chloride and triethylamine to give the linker 8.

Alternately, linker 8' can be prepared. One of the hydroxyl groups in the tetraethylene glycol 6 can be selectively protected as benzyl ether 7', which can then be treated with methanesulfonyl chloride and triethylamine to give the linker 8'.

The conjugation of DOTA with fluorinated alcohol 5 was then performed. The highly fluorinated alcohol 5 was first attached to the hydrophilic chain to provide compound 9 in good yield by treating the alcohol 5 with potassium hydride in tetrahydrofuran at room temperature for 30 minutes and then slowly adding methanesulfonylate 8 (or, alternatively, 8') at the same temperature. Due to the three bulky perfluoro-tert-butyl group in compound 5, sodium hydride failed to deprotonate the hydroxyl group in alcohol 5 and resulted in recovery of the alcohol 5 and methanesulfonylate 8 after a long reaction time. After removal of the tert-butyldimethylsilyl group in compound 9 by tetrabutylammonium fluoride, the newly formed hydroxyl group in compound 10 was treated with ethanesulfonyl chloride and triethylamine to give the methanesulfonylate 11 in good yield. Because of their surfactant properties, compounds 9, 10 and 11 typically cannot be extracted from the reaction mixtures by F362 (perfluorohexanes), but those compounds can be easily purified by flash chromatography. Attaching the cyclen ring to the fluorinated methanesulfonylate 11 was achieved by treating compound 11 with 2 equivalents of cyclen at 60° C. Fluorinated silica gel was used to purify the cyclen derivative 12. The other three "arms" were incorporated into compound 12 by treating 12 with ethylbromoacetate in the presence of potassium carbonate. The resulting ester 13 was then hydrolyzed to give the final product 1.

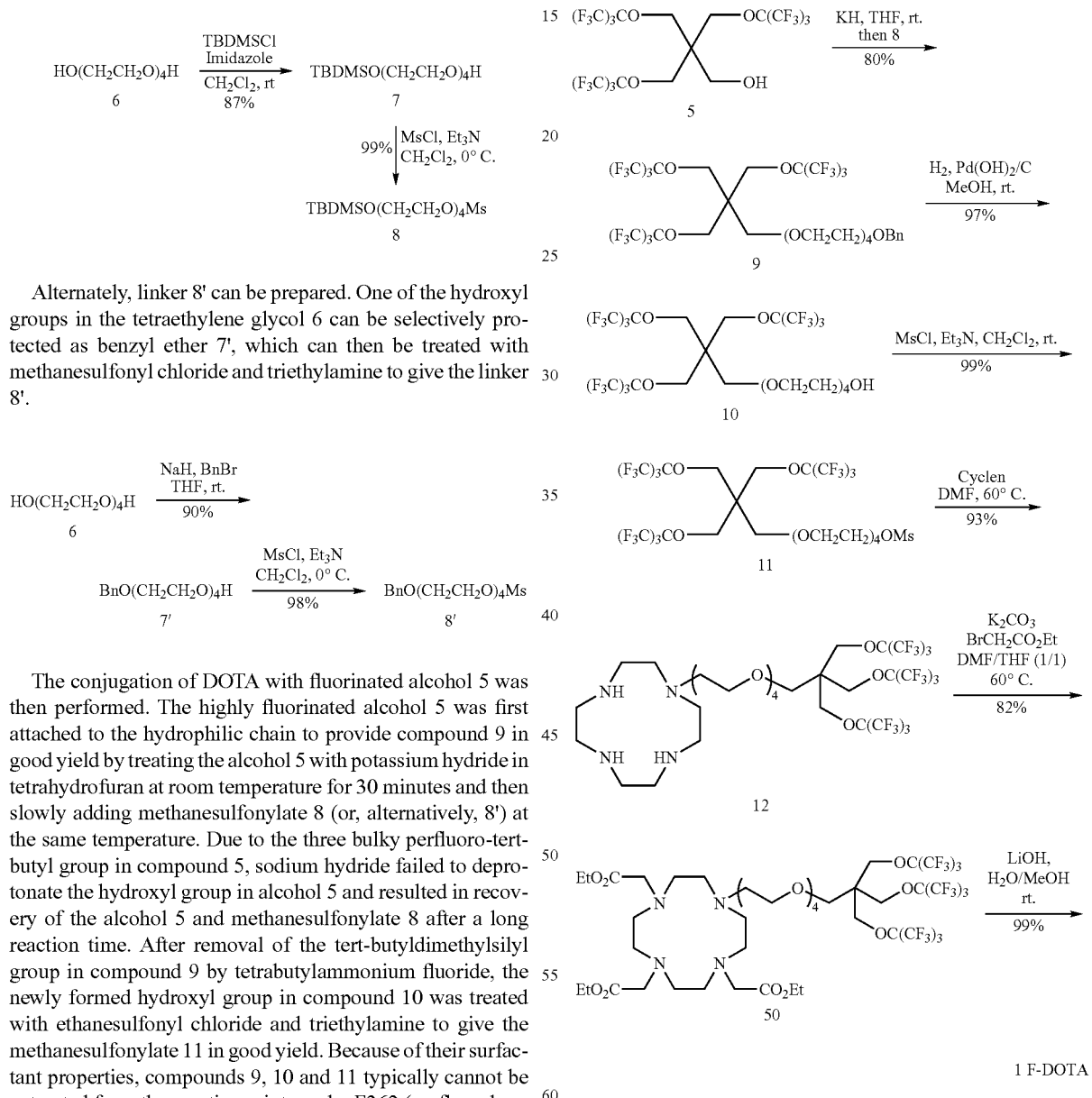

The synthesis of F-surfactant-octreotide, or any other peptide, an F-surfactant with a carboxylic end group (—COOH) can be used. Such a surfactant can be conjugated to the N-terminus of a peptide as the last step of solid-phase synthesis, as illustrated below:

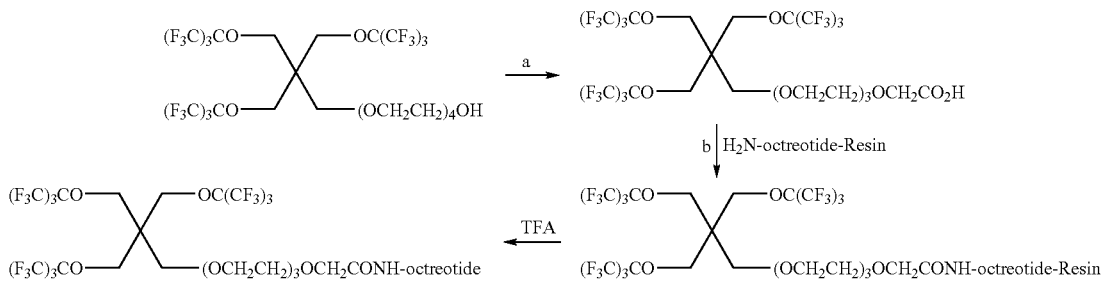

Synthesis route of F-surfactant-octreotide (applicable to other peptides or any molecule which contains an unprotected amine group on a solid-phase support). a. Jones reagent, Acetone, rt.; b. HOBt, DIC, DMF, rt. Octreotide sequence: DPhe1-c[Cys2-Phe3-DTrp-4-Lys5-Thr6-Cys7]-Thr8-NH$_2$. Standard solid-phase synthesis using Fmoc chemistry can be employed. The cyclic S—S bond between Cys2 and Cys7 can be formed via air oxidation during post-cleavage workups.

F. METHODS OF USING

1. Conjugating F-Surfactants to Proteins and Monoclonal Antibodies

If the protein or monoclonal antibodies (mAb) contains thiol group(s), then the F-surfactant with a thiol (—SH) end group can be used to form a disulfide bond, using established S—S bond formation conditions (e.g., I. Annis, B. Hargittai & G. Barany. Disulfide bond formation in Peptides. Methods in Enzymology, 289, 198-221, 1997; Tam, J. P., Wu, C.-R., Liu, W. & Zhang, J-W. Disulfide bond formation in peptides by dimethyl sulfoxide. Scope and applications. J. Am. Chem. Soc. 113, 6657-6662, 1991):

F-surfactant-SH+HS-Protein=F-surfactant-S—S-Protein

If the protein or mAb contains thiol group(s), then one alternative method is to conjugate it to the F-surfactant with an amine (—NH$_2$) end group, using the commercially available heterobifunctional crosslinking agent succinimidyl 4-(N-maleimido-methyl)cyclohexane-1-carboxylate (SMCC) (Bieniarz, C., Husain, M., Barnes, G., King, C. A. & Welch, C. J. Extended length heterofunctional coupling agents for protein conjugations. Bioconjugate Chem. 8, 88-95, 1996; Weiden, P. L. et al., Pretargeted radioimmunotherapy for treatment of non-Hodgkin's lymphoma (NHL): initial phase I/II study result. Cancer Biother. & Radiopharm. 15, 15-29, 2000; Subbiah, K. et al., Comparison of immunoscintigraphy, efficacy, and toxicity of conventional and pretargeted radioimmunotherapy in CD20-expressing human lymphoma xenografts. J. Nucl. Med. 44, 437-445, 2003). Specifically, one side of SMCC will be conjugated to F-surfactant-NH$_2$ and the other side will be conjugated to the thiol group(s) on the protein or antibody, as illustrated in the following scheme:

F-surfactant-NH$_2$

SMCC

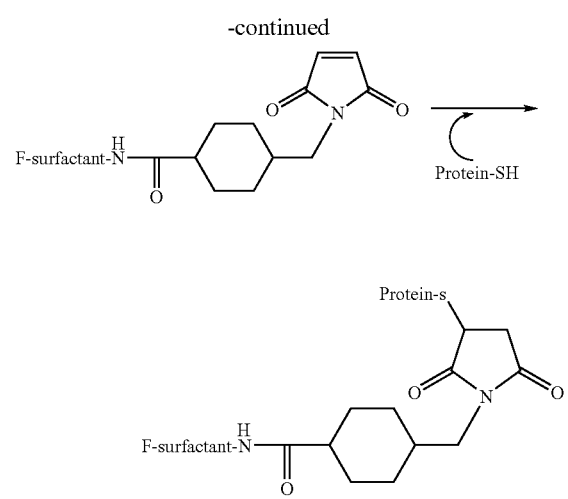

If the protein or mAb contains amine group(s), then it can be conjugated to the F-surfactant with a thiol (—SH) end group, using the commercially available heterobifunctional crosslinking agent succinimidyl 4-(N-maleimido-methyl)cyclohexane-1-carboxylate (SMCC) (Bieniarz, C., Husain, M., Barnes, G., King, C. A. & Welch, C. J. Extended length heterofunctional coupling agents for protein conjugations. Bioconjugate Chem. 8, 88-95, 1996; Weiden, P. L. et al., Pretargeted radioimmunotherapy for treatment of non-Hodgkin's lymphoma (NHL): initial phase I/II study result. Cancer Biother. & Radiopharm. 15, 15-29, 2000; Subbiah, K. et al., Comparison of immunoscintigraphy, efficacy, and toxicity of conventional and pretargeted radioimmuno-therapy in CD20-expressing human lymphoma xenografts. J. Nucl. Med. 44, 437-445, 2003). Specifically, one side of SMCC can be conjugated to F-surfactant-SH and the other side can be conjugated to amine group(s) on the protein or antibody, as illustrated in the following scheme:

Protein-NH$_2$

SMCC

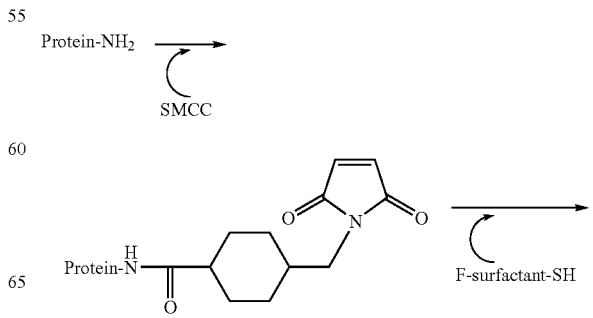

-continued

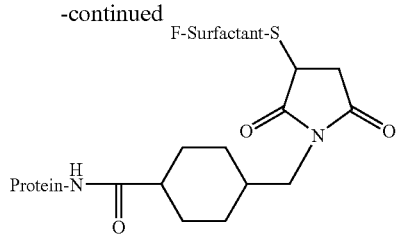

2. Methods of Treatment

In one aspect, the methods relate to the treatment of a disease of uncontrolled cellular proliferation comprising administering to a mammal diagnosed as having a disease of uncontrolled cellular proliferation one or more of the disclosed compounds, one or more of the disclosed nanoparticles, one or more of the disclosed multifunctional delivery vehicles, one or more of the disclosed pharmaceutical compositions, or pharmaceutically acceptable salts or prodrugs thereof, in an amount effective to treat the disease of uncontrolled cellular proliferation. In a further aspect, the disease of uncontrolled proliferation is a carcinoma, lymphoma, leukemia, or sarcoma or other cancers and tumors. In a further aspect, the mammal is a human.

3. Textile-Finishing Agent

Fluorinated textile-finishing agents have been commercialized. Textiles treated with such agent shows excellent both water and oil repellency. There are also some reports indicating that fluorinated surfactants show durable antimicrobial activity. [Shao, H.; Meng, W.-D.; Qing, F.-L. Synthesis and surface antimicrobial activity of a novel perfluorooctylated quaternary ammonium silane coupling agent. J. Fluorine Chem. 125, 2004, 721-724]. However, reported fluorinated textile-finishing agents employed a non-branched perfluorocarbon chain, which means more such agent should be used on textiles to achieve adequate surface properties. Fluorinated surfactants synthesized herein can have an umbrella shape, making these surfactants are more effective than conventional ones.

The surfactant can be cross-linked to the fiber of textile with the ending group (such as carboxylic group, or silane group) by following standard procedures. [AATCC Technical Manual, American Association of Textile Chemists and colorists, Research Triangle Park, N.C., 1989.] The antimicrobial activity and water and oil repellency property can also be determined by the standard procedures.

4. Surface Modification Coating

The fluorinated surfactants used as surface coatings can have advantages over conventional coatings: 1. The fluorinated surfactant can exhibit special surface properties, such as, water and oil repellency, antimicrobial, and/or anti-erosion; 2. The fluorinated surfactant can have an umbrella shape, so the surfactant can exhibit far higher efficiency than common coatings; 3. The surfactant can be conjugated to the surface by chemical bonds through reaction between the surfactant and the material to be coated, so the coating can be more stable even under very extreme conditions than non-bond coatings; 4. By manipulation the length of the hydrophilic chain, one can easily coat the surface in a three dimensional fashion. [Ulman, A. Formation and Structure of Self-Assembled Monolayers Chem. Rev. 1996, 96, 1533-1554]

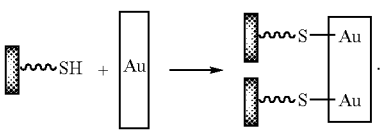

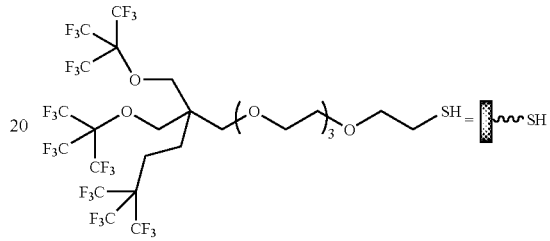

5. Gene Delivery

One feature in the disclosed designs is a fluorocarbon moiety with all fluorine atoms in spherically symmetric positions, as a result of symmetric branching. The consequence of this is that all the fluorine atoms give one $^{19}F$ signal (FIG. 1). This can greatly elevate the sensitivity for magnetic resonance detection of the $^{19}F$ signal. Such a moiety can be attached to an arbitrary chemical construct (proteins, nucleic acids, polymers, surfactants, oils, etc.) as a $^{19}F$ probe. The much broader chemical shift range of $^{19}F$ (>200 ppm) in comparison with that of $^1H$ (ca. 20 ppm) makes it very sensitive toward local chemical environment changes. This has broad implications in analytical, bioanalytical, clinical, and pharmaceutical chemistry. Further, for in vivo applications, because there is no MRI-detectable endogenous $^{19}F$ signal, such a fluorocarbon moiety serves as an excellent probe for in vivo biochemical processes associated with normal physiological and pathophysiological states. One specific example is to attach such a moiety to existing nucleic acid condensing agents for gene delivery. The utility of such a probe is that the chemical shift change of $^{19}F$ can signal the release of encapsulated DNA or RNA, allowing researchers and in the future, clinicians, to determine exactly when the gene is released, hence gathering valuable pharmacokinetic data in a non-invasive manner in real time. Such a real-time gathering of pharmacokinetic data is currently not available. The following diagram illustrating the attachment of an exemplary fluorocarbon moiety to a Gemini surfactant currently explored as gene delivery agent [Kirby, A.; Camilleri, P.; Engberts, J. B. F. N.; Feiters, M. C.; Nolte, R. S. M.; Soderman, N, O.; Bergsma, M.; Bell, P. C.; Fielden, M. L.; Rodriguez, C. L. G.; Guedat, P.; Kremer, A.; McGregor, C.; Perrin, C.; Ronsin, G.; van Eijk, M. C. P. Angew. Chem. Int. Ed. 2003, 42, 1448-1457].

Current Gemini surfactant structure (no $^{19}$F labeling)

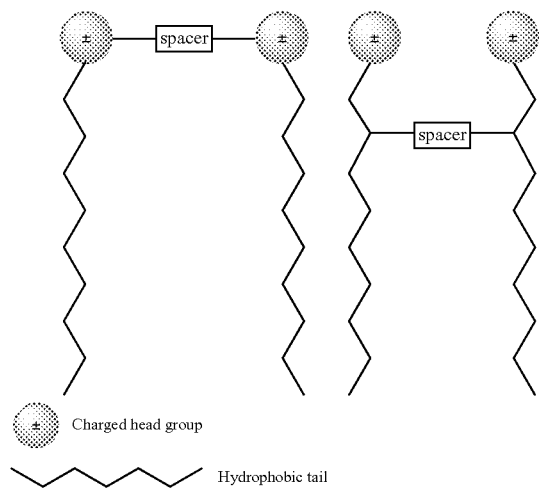

$^{19}$F-labeled Gemini surfactant structure

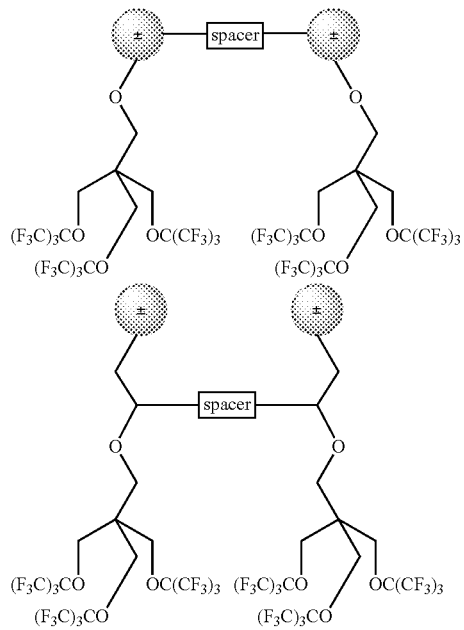

6. Multi-Modular Methods

Figure 7:
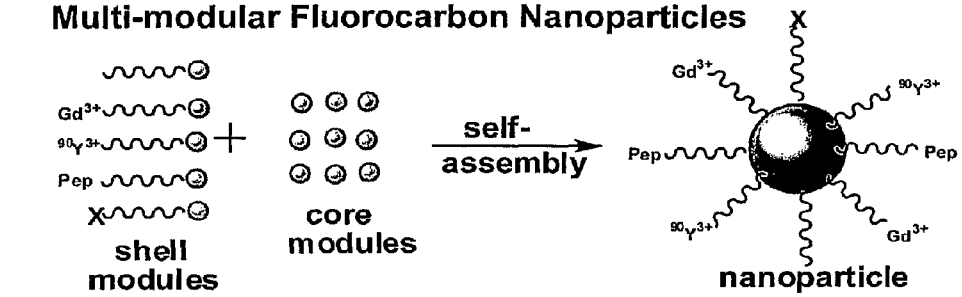
FIG. 7 shows a schematic representation of the multimodular fluorocarbon nanoparticles.

The present multifunctional delivery vehicles can have multiple delivery capacities, including the delivery of radionuclides for radiotherapy (e.g., $^{90}Y^{3+}$) and/or nuclear imaging ($^{111}In^{3+}$ or $^{86}Y^{3+}$), the delivery stable metallic ions for $^{1}H$ MR imaging (e.g., $Gd^{3+}$ or $Tb^{3+}$), the delivery of fluorocarbons for $^{19}F$ MR imaging, $^{19}F$ oximetry and even temperature measurement, the delivery of $O_2$, the delivery of chemodrugs, the delivery of chemo- and radio-therapy adjuvants, the delivery of nucleic acids (DNA, RNA) for gene therapy, etc. However, in one aspect, the delivery vehicle does not have to delivery everything simultaneously. It can delivery one, two, three, four five, or more of these agents. Due to the modular design of the nanoparticles, multiple functions can be embedded into one delivery vehicle through the incorporation of multiple modules. For examples of the multi-modular methods using the present compounds, see FIG. 7.

In one aspect, the methods relate to delivering radionuclides for radiotherapy comprising the steps of complexing a radionuclide with at least one of the present compounds; and administering the complex to a mammal in an amount effective for radiotherapy. In a further aspect, the radionuclide is at least one of $^{111}In^{3+}$ or $^{86}Y^{3+}$.

In one aspect, the methods relate to A method of delivering a metallic ion for $^{1}H$ imaging comprising the steps of complexing a metal ion with at least one of the present compounds; and administering the complex to a subject in an amount effective for detection by $^{1}H$ MRI. In a further aspect, the ion is at least one of $Gd^{3+}$ or $Tb^{3+}$.

In one aspect, the methods relate to delivering a fluorocarbon for $^{19}F$ imaging comprising the steps of administering at least one of the present compounds to a subject in an amount effective for detection by $^{19}F$ MRI; and performing a $^{19}F$ MRI experiment of the subject. In a further aspect, the subject is a mammal, for example, a human.

In one aspect, the methods relate to delivering oxygen comprising the steps of complexing oxygen with at least one of the present compounds; and administering the complex to a subject.

In one aspect, the methods relate to a multi-modular treatment method comprising the step of simultaneously performing at least two of the present methods. In a further aspect, at least three of the present methods are simultaneously performed.

G. COMPOSITIONS

In one aspect, the compositions relate to a bilayer comprising at least two molecules of the disclosed compounds. In a further aspect, the compositions relate to a micelle comprising a plurality of molecules of the disclosed compounds. In a further aspect, the compositions relate to a coating comprising at least one molecule of the disclosed compounds. In a further aspect, the compositions relate to a pharmaceutical composition comprising one or more of the disclosed compounds or pharmaceutically acceptable salts or prodrugs thereof, and one or more pharmaceutically acceptable carriers.

H. KITS

Disclosed herein are kits that are drawn to compounds and/or reagents that can be used in practicing the methods disclosed herein. The kits can include any reagent or combination of reagents discussed herein or that would be understood to be required or beneficial in the practice of the disclosed methods. For example, the kits could include reagents to perform complexation reactions discussed in certain embodiments of the methods, as well as buffers and solvents required to use the reagents as intended.

I. COMPOSITIONS WITH SIMILAR FUNCTIONS

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

J. $^{1}H$-$^{19}F$ DUAL NUCLEI IMAGING

The combination of high sensitivity and lack of background interference makes $^{19}F$ an idea candidate for providing an additional MR modality complementary to $^1$H MRI. Here, a novel multi-modality MRI regent which has a DOTA part for $^1$H MRI and a highly branched fluorinated part for $^{19}$F MRI was designed and successfully synthesized. All the fluorine atoms in the molecule show only one sharp $^{19}$F NMR signal, thereby indicating that such molecules are ideal for $^{19}$F MRI.

The combination of high sensitivity and lack of background interference makes $^{19}$F an idea candidate for providing an additional MR modality complementary to $^1$H MRI. Conventional MRI is achieved through the $^1$H$_2$O signal. Although using $^1$H$_2$O signal for detection affords high resolution MRI, because of high water concentration in the tissue provides sufficient signals, it lacks of specificity. In contrast to the abundant presence of $^1$H$_2$O, there is no MRI-detectable endogenous $^{19}$F compound in human tissues. Therefore, background or interfering endogenous $^{19}$F signal is typically negligible. The nuclear magnetic resonance sensitivity of $^{19}$F is only secondary to $^1$H (83% as sensitive).

Quantification of in vivo concentration based on $^1$H$_2$O relaxation parameters is typically not reliable due to the heterogeneity of in vivo proton signals [Morawski, A. M.; Winter, P. M.; Crowder, K. C.; Caruthers, S. D.; Fuhrhop, R. W.; Scott, M. J.; Robertson, J. D.; Abendschein, D. R.; Lanza, G. M.; Wickline, S. A. *Magn. Reson. Med.* 2004, 51, 480-486. Morawski, A. M.; Winter, P. M.; Yu, X.; Fuhrhop, R. W.; Scott, M. J.; Hockett, F.; Robertson, J. D.; Gaffney, P. J.; Lanza, G. M.; Wickline, S. A. *Magn. Reson. Med.* 2004, 52, 1255-1262.]. The lack of background interference makes $^{19}$F MRI an ideal imaging modality for this application if the drug contains fluorine. [Lanza, G. M.; Yu, X.; Winter, P. M.; Abendschein, D. R.; Karukstis, K. K.; Scott, M. J.; Chinen, L. K.; Fuhrhop, R. W.; Scherrer Morawski, A. M.; Hockett, F.; Robertson, J. D.; Gaffney, P. J.; Wickline, S. A. *Magn. Reson. Med.* 2004, 52, 1255-1262.]. A $^1$H-$^{19}$F dual nuclei imaging agent allows one to quickly identify areas of interest based on Gd(M)-enhanced $^1$H$_2$O signal and then make more accurate quantification based on the $^{19}$F signal. When conjugated to a drug, such a dual nuclei imaging agent allows one to determine local drug concentration. This enables one to determine the actual amount of drug delivered to pathological sites and hence helps a physician to develop an image-based dosing for each patient (individualized dosimetry) [Wickline, S. A.; Lanza, G. M. J. *Cell. Biochem.* (*suppl.*) 2002, 39, 90-97.].

Multinuclear magnetic resonance imaging (MRI) is playing an increasingly important role in cancer research and holds great potential for cancer diagnosis and intervention [Gimi, B.; Pathak, A. P.; Ackerstaff, E.; Glunde, K.; Artemov, D.; Bhujwalla, Z. M. *Proc. IEEE*, 2005, 93, 784-799.]. Compared with dual modality imaging methods, such as MRI-optical. MRI-PET or MRI-ultrasound, $^1$H-$^{19}$F dual nuclei imaging requires only one imaging modality and is fully compatible with existing MR scanners (magnet, console, etc.) available in almost every hospital in developed countries; the $^{19}$F signal obtained from $^{19}$F MR spectroscopy or imaging can be overlaid with $^1$H MR images (acquired in the same imaging session) without additional co-registration. Therefore, $^1$H-$^{19}$F dual nuclei imaging imposes hardly any extra burden on either the patients or the health care system.

However, $^{19}$F MRI is usually hampered by the fact that most perfluorocarbons exhibit multipeak-spectra resulting in $^{19}$F MRI with chemical shift artifacts. On the other hand, for quantitative $^{19}$F MRI, only one resonance peak may be used. In most $^{19}$F MRI research, only very few fluorine atoms (10-20% of the total fluorine atoms) have been used during the $^{19}$F MRI process. The disclosed highly fluorinated compounds are suitable for methods employing $^{19}$F MRI because (1) the cyclic chelators, DOTA and its analogs (e.g, DO3A), have the highest stability toward Gd(M) among the chelators currently in clinical use, (2) perfluoro-tert-butyl ether has a very high $^{19}$F signal intensity (27 chemical identical fluorine atoms; see FIG. 1) and high stability (stable to base and acid), and (3) tetraethylene glycol has good biocompatibility and aqueous solubility.

Fluorinated DOTA and its analogs (collectively referred as F-DOTA) can be used as imaging agents for the liver and spleen due to preferential accumulation of fluorocarbons in these organs.

K. TARGETED FLUOROCARBON NANOPARTICLES

The multifunctional delivery vehicles can be based on fluorocarbon nanoparticles, formulated as microemulsions (also called nanoemulsions). Chelators, peptides and other targeting molecules (e.g., antibodies) can be attached to the surface of the nanoparticles for radionuclide carrying and tumor targeting, respectively. The nanoparticles can be assembled in a modular fashion from highly fluorinated molecules in three steps.

1. Fluorocarbon Nanoparticles

This step can involve the syntheses of highly fluorinated oils (F-oil) and surfactants (F-surfactant) and the formulation of F-oils and F-surfactants into microemulsions of fluorocarbon nanoparticles. The nanoparticles can have two modules: F-oils and F-surfactants.

2. Chelator-Decorated Fluorocarbon Nanoparticles

A macrocyclic chelator, 1,4,7,10-tetraazacyclododecane-1,4,7,10-tetraacetate (DOTA), and/or its analogs, can be linked to the end of an F-surfactant, forming a new surfactant: F-surfactant-DOTA. F-surfactant-DOTA can be added as another ingredient in microemulsion formulation, forming chelator-coated fluorocarbon nanoparticles. These nanoparticles can have three modules: F-oil, F-surfactant and F-surfactant-DOTA.

Typically, DOTA forms very stable complexes with trivalent metallic ions and is the chelator used in the radio-pharmaceutical OctreoTher® (for $^{90}$Y$^{3+}$ chelation) and in the MRI contrast agent Dotarem® (for Gd$^{3+}$ chelation). DOTA can be used to chelate Gd$^{3+}$ for $^1$H MR imaging. One purpose of $^1$H-$^{19}$F dual imaging is to use these two imaging modes to corroborate each other. In actual targeted radiotherapy, DOTA can be used to chelate metallic radionuclide ions, such as $^{90}$Y(III), for cancer treatment.

3. Development of Peptide- and Chelator-Decorated Fluorocarbon Nanoparticles

A tumor targeting peptide, octreotide, can be conjugated to an F-surfactant, forming a new surfactant: F-surfactant-peptide. F-surfactant-peptide can be added as yet another ingredient in microemulsion formulation, forming peptide- and chelator-decorated fluorous nanoparticles. In one aspect, these nanoparticles can have four modules: F-oil, F-surfactant, F-surfactant-DOTA and F-surfactant-peptide.

Octreotide is an octapeptide analog of the natural tetradecapeptide hormone somatostatin and targets neuroendocrine tumors (e.g., pancreatic cancer, small cell lung cancer, etc.). Octreotide is the targeting moiety in two radiopharmaceuticals: OctreoScan® (FDA-approved), which carries $^{111}$In$^{3+}$ for cancer radio-diagnosis, and OctreoTher® (under clinical trial), which carries $^{90}$Y$^{3+}$ for cancer radiotherapy.

4. Biodistribution

The biodistribution of targeted fluorocarbon nanoparticles can be conducted in rats with subcutaneous pancreatic tumor implants. The amount of nanoparticles accumulated in the tumor and in liver and spleen can be determined to calculate the tumor-to-organ ratio. The tumor-to-organ ratios of targeted versus non-targeted nanoparticles can be compared to evaluate the effectiveness of targeting.

5. Multifunctional Delivery Vehicles for Image-Guided Targeted Radiotherapy

A multifunctional delivery vehicle can improve the efficacy of targeted radiotherapy in two ways. First, it can tailor the dosing schedule to meet the pharmacokinetic and $pO_2$ profiles of each patient (i.e., individualized treatment plans). Second, it can improve the pharmacokinetic and $pO_2$ profiles of each patient. The prerequisite for achieving these two goals is to obtain patient-specific pharmacokinetic and $pO_2$ information. Magnetic resonance imaging (MR) is an excellent tool for obtaining patient-specific information for drug delivery applications [Swartz, H. Seeing is believing-visualizing drug delivery in vitro and in vivo. Adv. Drug Del. Rev. 57, 1085-1086, 2005; Kelloff, et al., The progress and promise of molecular imaging probes in oncologic drug development. Clin. Cancer Res. 11, 7967-7985, 2005]. The disclosed compounds, methods, and compositions integrate imaging technologies and delivery technologies into one multifunctional delivery vehicle. Such a delivery vehicle can obtain patient-specific pharmacokinetics and $pO_2$ profiles via MRI and improve the pharmacokinetic and $pO_2$ profiles of a patient for radiotherapy (e.g., it can deliver $O_2$ to the tumor). MRI can then guide the delivery of radiotherapeutic drugs (image-guided targeted radiotherapy).

The present compositions integrate five roles, radionuclide carrier, tumor targeting, imaging agent, $pO_2$ probe and $O_2$ carrier, into one multifunctional delivery vehicle. The radionuclide carrier function can ensure that there are no freely floating radionuclides as they can cause severe radiation damage to normal tissues. The tumor targeting function ensures that the radionuclides will accumulate preferentially in the tumor. The imaging agent function can allow a physician to trace the drug and visualize the tumor via MRI. Through drug tracing and tumor visualization that that one can obtain patient-specific pharmacokinetic data and confirm drug targeting. The $pO_2$ probe function can allow a physician to determine the oxygen tension at a particular tumor site. $pO_2$ can serve as a prognostic factor for radiotherapy [Nordsmark, M. & Overgaard, J. A confirmatory prognostic study on oxygenation status and loco-regional control in advanced head and neck squamous cell carcinoma treated by radiation therapy. Radiother. Oncol. 57, 39-43, 2000; Fyles, et al., Oxygenation predicts radiation response and survival in patients with cervix cancer. Radiother. Oncology, 48, 149-156, 1998]. $O_2$ delivery to tumor sites can sensitize hypoxic tumor cells toward radiation with $O_2$ acts essentially as an adjuvant for radiotherapy [Rockwell, S., Use of a perfluorochemical emulsion to improve oxygenation in a solid tumor. Int. J. Radiation Oncology Biol. Phys. 11, 97-103, 1985; Teicher, B. A. & Rose, C. M. Oxygen-carrying perfluorochemical emulsion as an adjuvant to radiation therapy in mice. Cancer Res. 44, 4285-4288, 1984].

Chemically, such a multifunctional delivery vehicle can be made of fluorocarbon nanoparticles with chelators and peptides attached to their surfaces. The nanoparticles can be assembled in a modular fashion from the various components and can be formulated as oil-in-water (o/w) microemulsions. The chelators act as carriers for metallic radionuclides (e.g., $^{90}Y^{3+}$). The chelators can also carry other metallic ions, such as $Gd^{3+}$ for contrast-enhanced $^1H$ MRI. The peptides are for tumor targeting. The fluorocarbon nanoparticles themselves play three roles simultaneously: $^{19}F$ imaging agent, which derives from the high $^{19}F$ payload of the nano-particles; $pO_2$ probe, which derives from the dependence of the relaxation behavior of $^{19}F$ on $pO_2$ ($^{19}F$ MR relaxometry) [Parhaml, P. & Fung, B. M. Fluorine-19 relaxation study of perfluoro chemicals as oxygen carriers. J. Phys. Chem. 87, 1928-1931, 1983]; $O_2$ carrier, which derives from the high solubility of $O_2$ in fluorocarbon microemulsions [Riess, J. G. Understanding the fundamentals of perfluorocarbons and perfluorocarbon emulsions relevant to in vivo oxygen delivery. Art. Cells, Blood Subs., and Biotechnology, 33, 47-63, 2005].

Note that since each nanoparticle carries both $Gd^{3+}$ ions and fluorocarbons, it is a $^1H$-$^{19}F$ dual nuclei MR imaging agent. While $^1H$ imaging is good at proving exquisite anatomical details due to the high intensity of the $^1H_2O$ signal, $^{19}F$ imaging is ideal for drug concentration determination as there is no detectable background $^{19}F$ signal in the human body [Lanza, et al., Targeted antiproliferative drug delivery to vascular smooth muscle cells with a magnetic resonance imaging nanoparticle contrast agent. Circulation, 106, 2842-2847, 2002; Morawski, et al., Quantitative "magnetic resonance immunohistochemistry" with ligand-targeted 19F nanoparticles. Magn. Reson. Med. 52, 1255-1262, 2004]. Note that $^{19}F$ is the second most sensitive nucleus for MR imaging with a sensitivity of 83% of that of $^1H$. Hence a $^1H$-$^{19}F$ dual nuclei MR imaging agent can simultaneously visualize tumor via the $^1H$ mode and trace the drug and quantify local drug concentration via the $^{19}F$ mode. Such local drug concentration determination will help with calculating the radiation dose delivered to the tumor site, a very important parameter in radiotherapy (microdosimetry) [Bacher, K. & Thierens, H. M. Accurate dosimetry: an essential step towards good clinical practice in nuclear medicine. Nucl. Med. Commun. 26, 581-586, 2005; Bardiès, M. & Pihet, P. Dosimetry and microdosimetry of targeted radiotherapy. Current Pharmaceutical Design, 6, 1469-1502, 2000]. Local radiation dosimetry typically requires experimental calibration between radiation dose and $^{19}F$ signal intensity.

$^{19}F$ MR relaxometry is a well-established non-invasive method for $pO_2$ determination and is generally the only NMR technique which can determine the absolute value of $pO_2$ [Swartz, H. M. & Dunn, J. F. Measurements of oxygen in tissues: overview and perspectives on methods. Adv. Experi. Med. Biol. 530, 1-12, 2003; Grucker, D. Oxymetry by magnetic resonance: applications to animal biology and medicine. Prog. Nucl. Magn. Reson. Spect. 36, 241-270, 2000; Zhao, D., Jiang, L. & Mason, R. P. Measuring changes in tumor oxygenation. Methods in Enzymology, 386, 378-418, 2004; Robinson, S. P. & Griffiths, J. R. Current issues in the utility of 19F nuclear magnetic resonance methodologies for the assessment of tumor hypoxia. Phil. Trans. R. Soc. Lond. B 359, 987-996, 2004]. The basic principle behind $^{19}F$ MR oximetry is that the spin-lattice relaxation rate constant ($R_1$) of fluorocarbon emulsions has a linear dependence on $pO_2$ [Parhaml, P. & Fung, B. M. Fluorine-19 relaxation study of perfluoro chemicals as oxygen carriers. J. Phys. Chem. 87, 1928-1931, 1983]. The significance of oximetry in radiotherapy lies in the fact that $pO_2$ correlates with the outcome of radiotherapy and hence can help with patient selection and dose optimization [Nordsmark, M., Overgaard, M. & Overgaard, J. Pretreatment oxygenation predicts radiation response in advanced squamous cell carcinoma of the head and neck. Radiother. Oncology, 41, 31-39, 1996; Nordsmark, M. & Overgaard, J. A confirmatory prognostic study on oxygenation status and loco-regional control in advanced head and neck squamous cell carcinoma treated by radiation therapy. Radiother. Oncol. 57, 39-43, 2000; Fyles, et al., Oxygenation predicts radiation response and survival in patients with cervix cancer. Radiother. Oncolgy, 48, 149-156, 1998; Brizel, D. M., Dodge, R. K., Clough, R. W. & Dewhirst, M. W. Oxygenation of head and neck cancer: changes during radiotherapy and impact on treatment outcome. Radiother. Oncology, 53, 113-117, 1999; O'Hara, J. A., Goda, F., Demidenko, E. & Swartz, H. M. Effect on regrowth delay in a murine tumor of scheduling spit dose radiation based on direct pO2 measurements by EPR oximetry. Radia. Res. 150, 549-556, 1998; O'Hara, et al., Response to radioimmunotherapy correlates with tumor pO2 measured by EPR oximetry in human tumor xenografts. Radia. Res. 155, 466-473, 2001; Bussink, J., Kaanders, J. H. A. & van der Kogel, A. J. Clinical outcome and tumor microenvironmental effects of accelerated radiotherapy with carbogen and nicotinamide. Acta Oncologica, 38, 875-882, 1999; Kaanders, J. H. A. Bussink, J. & van der Kogel, A. J. Clinical studies of hypoxia modification in radiotherapy. Seminars in Radiat. Oncol. 14, 233-240, 2004; Al-Hallaq, et al., MRI measurements correctly predict the relative effects of tumor oxygenation agents on hypoxic fraction in rodent BA1112 tumors. Int. J. Radiat. Oncology Biol. Phys. 47, 481-488, 2000].

It has been demonstrated in both preclinical and clinical studies that oxygen breathing (in the form of carbogen, 95% $O_2$ and 5% $CO_2$) in conjunction with fluorocarbon microemulsions can alleviate tumor hypoxia and sensitize tumors toward radiation [Rockwell, S., Use of a perfluorochemical emulsion to improve oxygenation in a solid tumor. Int. J. Radiation Oncology Biol. Phys. 11, 97-103, 1985; Teicher, B. A. & Rose, C. M. Oxygen-carrying perfluorochemical emulsion as an adjuvant to radiation therapy in mice. Cancer Res. 44, 4285-4288, 1984; Al-Hallaq, et al., MRI measurements correctly predict the relative effects of tumor oxygenation agents on hypoxic fraction in rodent BA1112 tumors. Int. J. Radiat. Oncology Biol. Phys. 47, 481-488, 2000; Teicher, B. A. & Rose, C. M. Perfluorochemical emulsions can increase tumor radiosensitivity. Science, 223, 934-936, 1984; Rose, C., Lustig, R., McIntosh, N. & Teicher, B. A clinical trial of Fluosol DA 20% in advanced cell carcinoma of the head and neck. Int. J. Radiat. Oncology Biol. Phys. 12, 1325-1327, 1986; Koch, et al., Radiosensitization of hypoxic tumor cells by dodecafluoropentane: A gas-phase perfluorocarbon emulsion. Cancer Res. 62, 3626-3629, 2002]. Radiosensitization of tumor cells by $O_2$ is particularly effective for high-energy β-emitters [Kassis, A. I. & Adelstein, S. J. Radiobiologic principles in radionuclide therapy. J. Nucl. Med. 46 (Suppl. 1) 4S-12S, 2005], such as $^{90}Y^{3+}$, the radionuclide used in Zevalin® and OctreoTher®.

A multifunctional delivery vehicle with octreotide as the targeting peptide can be provided. Octreotide is the targeting peptide used in OctreoTher® [Smith, M. C., Liu, J., Chen, T., Schran, H., Yeh, C.-M., Jamar, F., Valkema, R., Bakker, W., Kvols, L., Krenning, E. & Pauwels, S. OctreoTher™: ongoing early clinical development of a somatostatin-receptor-targeted radionuclide antineoplastic therapy.]. This delivery vehicle can have application in targeted radiotherapy of neuroendocrine tumors.

6. Fluorocarbon Nanoparticles in Biomedicine

Fluorocarbon nanoparticles, in the form of microemulsions, have a long history in biomedicine. Non-targeted fluorocarbon nanoparticles have been explored as blood substitutes [Riess, J. G. Understanding the fundamentals of perfluorocarbons and perfluorocarbon emulsions relevant to in vivo oxygen delivery. Art. Cells, Blood Subs., and Biotechnology, 33, 47-63, 2005] and ultrasound contrast agents [Klibanov, A. L. Ligand-carrying gas-filled microbubbles: Ultrasound contrast agents for targeted molecular imaging. Bioconjugate Chem. 16, 9-17, 2005]. In the field of oncology, fluorocarbon nanoparticles have been used for tumor visualization via $^{19}F$ MR imaging [Longmaid, et al., In vivo 19F NMR imaging of liver, tumor, and abscess in rats. Invest. Radiol. 20, 141-145, 1985; Ratner, et al., Detection of tumors with 19F magnetic resonance imaging. Invest. Radiol. 23, 361-364, 1988; Mason, R. P., Antich, P. P., Babcock, E. E., Gerberich, J. L. & Nunnally, R. L. Perfluorocarbon imaging in vivo: A $^{19}F$ MRI study in tumor-bearing mice. Magn. Reson. Imag. 7, 475-485, 1989; Huang, M. Q., Basse, P. H., Yang, Q., Horner, J. A., Hichens, T. K. & Ho, C. MRI detection of tumor in mouse lung using partial liquid ventilation with a perfluorocarbon-in-water emulsion. Magn. Reson. Imag. 22, 645-652, 2004], tumor oximetry via $^{19}F$ MR relaxometry [Zhao, D., Jiang, L. & Mason, R. P. Measuring changes in tumor oxygenation. Methods in Enzymology, 386, 378-418, 2004; Robinson, S. P. & Griffiths, J. R. Current issues in the utility of 19F nuclear magnetic resonance methodologies for the assessment of tumor hypoxia. Phil. Trans. R. Soc. Lond. B 359, 987-996, 2004; Mason, R. P., et al., Regional tumor oxygen tension: Fluorine echo planar imaging of hexafluorobenzene reveals heterogeneity of dynamics. Int. J. Radiat. Oncology Biol. Phys. 42, 747-750, 1998; van der Sanden, et al., Characterization and validation of non-invasive oxygen tension measurements in human glioma xenografts by $^{19}F$-MR relaxometry. Int. J. Radiat. Oncology Biol. Phys. 44, 649-658, 1999] and tumor radiosensitization via $O_2$ delivery [Rockwell, S. Use of a perfluorochemical emulsion to improve oxygenation in a solid tumor. Int. J. Radiation Oncology Biol. Phys. 11, 97-103, 1985; Teicher, B. A. & Rose, C. M. Oxygen-carrying perfluorochemical emulsion as an adjuvant to radiation therapy in mice. Cancer Res. 44, 4285-4288, 1984; Al-Hallaq, H. A., Zamora, M., Fish, B. L., Farrell, A., Moulder, J. E. & Karczmar, G. S. MRI measurements correctly predict the relative effects of tumor oxygenation agents on hypoxic fraction in rodent BA1112 tumors. Int. J. Radiat. Oncology Biol. Phys. 47, 481-488, 2000; Teicher, B. A. & Rose, C. M. Perfluorochemical emulsions can increase tumor radiosensitivity. Science, 223, 934-936, 1984; Rose, C., Lustig, R., McIntosh, N. & Teicher, B. A clinical trial of Fluosol DA 20% in advanced cell carcinoma of the head and neck. Int. J. Radiat. Oncology Biol. Phys. 12, 1325-1327, 1986; Koch, C. J., Oprysko, P. R., Shuman, A. L., Jenkins, W. T., Brandt, G. & Evans, S. M. Radiosensitization of hypoxic tumor cells by dodecafluoropentane: A gas-phase perfluorocarbon emulsion. Cancer Res. 62, 3626-3629, 2002].

However, without targeting, the biodistribution of fluorocarbon nanoparticles is far from ideal. For example, in one study on $^{19}F$ MR imaging of tumor in mice, it was found that the accumulation of fluorocarbons in the spleen and liver is one to two orders of magnitude higher than that in the tumor [Mason, R. P., Antich, P. P., Babcock, E. E., Gerberich, J. L. & Nunnally, R. L. Perfluorocarbon imaging in vivo: A 19F MRI study in tumor-bearing mice. Magn. Reson. Imag. 7, 475-485, 1989]. Such a biodistribution profile is typically not acceptable for therapeutic applications in humans.

The development of targeted fluorocarbon nanoparticles started in late 1980's, using polyclonal antibodies [Shimizu, et al., Tumor imaging with anti-CEA antibody labeled 19F emulsion. Magn. Reson. Med. 5, 290-295, 1987; Mishima, et al., In vivo F-19 shift imaging with FTPA and antibody-coupled FMIQ. J. Magn. Reson. Imag. 1, 705-709, 1991]. More recently, targeted nanoparticles based on monoclonal antibody or peptide mimetics have been developed for the detection of cardiovascular pathologies. Initially, these nanoparticles were developed as contrast agents for ultrasound imaging [Lanza, et al., A novel site-targeted ultrasonic contrast agent with broad biomedical application. Circulation, 94, 3334-3340, 1996; Lanza, et al., Molecular imaging of stretch-induced tissue factor expression in carotid arteries with intravascular ultrasound. Invest. Radiol. 35, 227-234, 2000; Lanza, G. M. & Wickline, S. A. Targeted ultrasonic contrast agents for molecular imaging and therapy. Progress Cardiovas. Disease, 44, 13-31, 2001]. Later, their applications were extended into $^1$H MR imaging [Anderson, et al., Magnetic resonance contrast enhancement of neovasculature with $\alpha_v\beta_3$-targeted nanoparticles. Magn. Reson. Med. 44, 433-439, 2000; Flacke, et al., Novel M contrast agent for molecular imaging of fibrin. Circulation, 104, 1280-1285, 2001; Morawski, et al., Targeted nanoparticles for quantitative imaging of spare molecular epitopes with MRI. Magn. Reson. Med. 51, 480-486, 2004; Schmieder, et al., Molecular MR imaging of melanoma angiogenesis with $\alpha_v\beta_3$-targeted paramagnetic nanoparticles. Magn. Reson. Med. 53, 621-627, 2005]. Most recently, the potential of these targeted fluorocarbon nanoparticles as $^{19}$F MR contrast agents was demonstrated through the ex vivo imaging of a human carotid endarterectomy sample [Morawski, et al., Quantitative "magnetic resonance immunohistochemistry" with ligand-targeted $^{19}$F nanoparticles. Magn. Reson. Med. 52, 1255-1262, 2004]. This pioneering work on targeted fluorocarbon nanoparticles demonstrated two points. First, targeting can effectively improve the biodistribution. For example, in a preclinical study conducted in dogs for blood clot detection, the contrast-to-noise ratio between the targeted clot and blood was ≈118±21 and the contrast-to-noise ratio between targeted clot and control clot was 131±37 [Flacke, et al., Novel MRI contrast agent for molecular imaging of fibrin. Circulation, 104, 1280-1285, 2001] (but no liver and spleen accumulation data were presented). Second, targeted fluorocarbon nanoparticles can quantify the amount of drug delivered to a pathological site via the $^{19}$F signal [Lanza, et al., Targeted antiproliferative drug delivery to vascular smooth muscle cells with a magnetic resonance imaging nanoparticle contrast agent. Circulation, 106, 2842-2847, 2002; Morawski, et al., Quantitative "magnetic resonance immunohistochemistry" with ligand-targeted $^{19}$F nanoparticles. Magn. Reson. Med. 52, 1255-1262, 2004].

Current targeted fluorocarbon nanoparticles typically use egg yolk phospholipids (EYP) as emulsifying surfactants. This can lead to several shortcomings. The first issue is stability. EYP are typically not very stable as they are susceptible to chemical modifications (e.g., oxidation) [Riess, J. G. Oxygen carriers ("blood substitutes")-raison d'etre, chemistry and some physiology. Chem. Rev. 101, 2797-2919, 2001; Tarara, T. E., Malinoff, S. H. & Pelura, T. J. Oxidative assessment of phospholipid-stabilized perfluorocarbon-based blood substitutes. Art. Cells, Blood Subs., and Immob. Biotech. 22, 1287-1293, 1994]. This makes their production, handling and storage problematic. Also, due to limited interaction between hydrocarbon and fluorocarbon compounds, the physical stability of EYP-based fluorocarbon microemulsions is also not high. The nanoparticles are prone to aggregation (Ostwald ripening) [Postel, M., Riess, J. G. & Weers, J. G. Fluorocarbon emulsions—the stability issue. Art. Cells, Blood Subs., and Immob. Biotech. 22, 991-1005, 1994).

The second issue is derivatizability. The conjugation of phospholipids with targeting molecules is not straightforward. It can require special linkers which themselves can present a problem. For instance, the biotin-(strept)avidin linker system used in some targeted fluorocarbon nanoparticle [Lanza, et al., Targeted antiproliferative drug delivery to vascular smooth muscle cells with a magnetic resonance imaging nanoparticle contrast agent. Circulation, 106, 2842-2847, 2002; Morawski, et al., Quantitative "magnetic resonance immunohistochemistry" with ligand-targeted $^{19}$F nanoparticles. Magn. Reson. Med. 52, 1255-1262, 2004; Lanza, et al., A novel site-targeted ultraosonic contrast agent with broad biomedical application. Circulation, 94, 3334-3340, 1996; Flacke, et al., Novel MRI contrast agent for molecular imaging of fibrin. Circulation, 104, 1280-1285, 2001; Morawski, et al., Targeted nanoparticles for quantitative imaging of spare molecular epitopes with MRI. Magn. Reson. Med. 51, 480-486, 2004] can suffer from interference from endogenous biotin and immunogenicity of (strept)avidin, as demonstrated by studies on pretargeted radioimmunotherapy [Goldenberg, D. M. Targeted therapy of cancer with radiolabeled antibodies. J. Nucl. Med. 43, 693-713, 2002; Boerman, O. C., van Schaijk, F. G., Oyen, W. J. G. & Corstens, F. H. M. Pretargeted radioimmunotherapy of cancer: progress step by step. J. Nucl. Med. 44, 400-411, 2003; Knox, et al., Phase II trial of yttrium-90-DOTA pretargeted by NR-LU-10 antibody/streptavidin in patients with metastatic colon cancer. Clin. Cancer Res. 6,406-414, 2000; Hamblett, K. J., Kegley, B. B., Hamlin, D. K., Chyan, M. K., Hyre, D. E., Press, O. W., Wilbur, D. S. & Stayton, P. S. A streptavidin-biotin system that minimizes blocking by endogenous biotin. Bioconjugate Chem. 13, 588-598, 2002]. Also, conjugation products can be heterogeneous if the derivatization reaction involves amine (—NH$_2$) or thiol (—SH) groups because the targeting peptide or mAb might have several such groups [Lanza, et al., Molecular imaging of stretch-induced tissue factor expression in carotid arteries with intravascular ultrasound. Invest. Radiol. 35, 227-234, 2000]. Most critically, however, is that derivatization has very limited options, caused primarily by intrinsic limitations of phospholipid chemistry. For example, peptide-targeted fluorocarbon nanoparticles have not been demonstrated previously. Peptide mimetic-conjugated nanoparticles, however, have been developed [Schmieder, et al., Molecular MR imaging of melanoma angiogenesis with $\alpha_v\beta_3$-targeted paramagnetic nanoparticles. Magn. Reson. Med. 53, 621-627, 2005; Winter, et al., Molecular imaging of angiogenesis in nascent Vx-2 rabbit tumor using a novel $\alpha_v\beta_3$-targeted nanoparticle and 1.5 tesla magnetic resonance imaging. Cancer Res. 63, 5838-5843, 2003]. The conjugation involves a thiolate group which is not present in regular peptides.

The third issue is heterogeneity. There are several factors contributing to heterogeneity. The first factor is molecular diffusion and aggregation which lead to heterogeneity in nanoparticle size [Postel, M., Riess, J. G. & Weers, J. G. Fluorocarbon emulsions—the stability issue. Art. Cells, Blood Subs., and Immob. Biotech. 22, 991-1005, 1994]. This issue is intrinsic to emulsion formulation. However, it is further confounded by the use of EYP as the emulsifier. This is because EYP is not a pure compound. Rather, it is a class of phospholipids, including minor components such as phosphatedylinositol, phosphatidic acids, lysophosphatidylethanolamine, and fatty acids [Riess, J. G. Oxygen carriers ("blood substitutes")-raison d'etre, chemistry and some physiology. Chem. Rev. 101, 2797-2919, 2001]. Such minor components can undergo chemical modification (e.g., oxidation) during production. They can also participate in the conjugation reaction with targeting molecules. Both processes can contribute to nanoparticle heterogeneity. This issue can be worsened if the composition of these minor components varies from batch to batch. As a result, the size distribution of current targeted fluorocarbon nanoparticles can be very broad [Lanza, et al., Molecular imaging of stretch-induced tissue factor expression in carotid arteries with intravascular ultrasound. Invest. Radiol. 35, 227-234, 2000; Winter, et al., Molecular imaging of angiogenesis in nascent Vx-2 rabbit tumor using a novel $\alpha_v\beta_3$-targeted nanoparticle and 1.5 tesla magnetic resonance imaging. Cancer Res. 63, 5838-5843, 2003; Winter, et al., Improved molecular imaging contrast agent for detection of human thrombus. Magn. Reson. Med. 50, 411-416, 2003]. For example, in one case of biotinylated fluorocarbon nanoparticles, the size of the nanoparticles ranges from 50 nm to 1000 m with the average around 250 nm [Winter, et al., Improved molecular imaging contrast agent for detection of human thrombus. Magn. Reson. Med. 50, 411-416, 2003]. A consequence of such broad size distribution is that the $^{19}$F signal is also broad [Morawski, et al., Quantitative "magnetic resonance immunohistochemistry" with ligand-targeted $^{19}$F nanoparticles. Magn. Reson. Med. 52, 1255-1262, 2004]. Broad size distribution can make the biodistribution of the nanoparticles difficult to control and may lower therapeutic efficacy while broad $^{19}$F signal lowers the sensitivity of $^{19}$F MRI.

7. Engineering of Targeted Fluorocarbon Nanoparticles

At the molecular level, EYP can be replaced by synthetic fluorinated surfactants (F-surfactants). This avoids numerous problems associated with EYP. Chemically, F-surfactants are very inert molecules, leading to greater chemical stability. Also, due to preferential fluorocarbon-fluorocarbon interactions [Curran, D. & Lee, Z. Fluorous techniques for the synthesis and separation of organic molecules. Green Chem. G3-G7, 2001], interactions between the outer shell (made of F-surfactants) and inner core (made of F-oils) of the nanoparticles can be much enhanced, leading to greater physical stability. Further, as synthetic molecules, minor components and batch-to-batch variations are negligible. All these features should increase the stability while decrease the heterogeneity of fluorocarbon nanoparticles. Indeed, previous studies have shown that when EYP is replaced by F-surfactants, the stability of fluorocarbon microemulsions significantly increases [Riess, J. G. Oxygen carriers ("blood substitutes")-raison d'etre, chemistry and some physiology. Chem. Rev. 101, 2797-2919, 2001; Postel, M., Riess, J. G. & Weers, J. G. Fluorocarbon emulsions—the stability issue. Art. Cells, Blood Subs., and Immob. Biotech. 22, 991-1005, 1994]. However, new F-surfactants and F-oils, in particular the disclosed compounds, can be used instead of commercially available fluorochemicals.

Based on the molecular theories of the liquid state [Chandler, D. Structures of molecular liquids. Annu. Rev. Phys. Chem. 29, 441-471, 1978], without wishing to be bound by theory, it is believed that, if the shape of the F-surfactant matches the shape of the F-oil, the stability and the heterogeneity of the nanoparticles are enhanced and reduced, respectively. The reason is that the "cavity" vacated by an F-oil molecule can be filled in snuggly by an F-surfactant molecule and vice versa.

To solve the issue of peptide conjugation, F-surfactants which can be directly conjugated to the N-terminus of peptides during solid-phase synthesis can be synthesized. This simplifies the derivatization process and results in only one conjugation product, hence reducing heterogeneity. This method has general applicability toward the solid-phase synthesis of any targeting molecules.

At the formulation level, a modular approach toward nanoparticle assembly is used. Specifically, an array of F-surfactants and F-oils can be synthesized. The length and the charge of the hydrophilic moiety of the F-surfactants can be varied systematically. Further, some F-surfactants can be conjugated to a chelator (for carrying metallic radio-nuclides and/or stable metallic ions) while some can be conjugated to a peptide (for tumor targeting). The F-oils can have various hydrocarbon tails to modulate its lipophilicity, which is an important consideration in fluorocarbon nanoparticle formulation [Riess, J. G. Oxygen carriers ("blood substitutes")-raison d'etre, chemistry and some physiology. Chem. Rev. 101, 2797-2919, 2001]. Purified modules can be mixed together for nanoparticle constitution.

Modular nanoparticle assembly is central to achieving multifunctionality as it allows one to integrate several functions into one delivery vehicle through the incorporation of different modules. Another important consequence of modular assembly is that it allows us to modulate the physicochemical properties of the nanoparticles (size, surface charge, chelator and peptide density, etc.) by mixing different modules at different molar ratios. Without wishing to be bound by theory, it is believed that, by modulating physicochemical properties of the nanoparticles, their in vivo pharmacokinetics are modulated.

8. Targeted Radiotherapy

Figure 2:
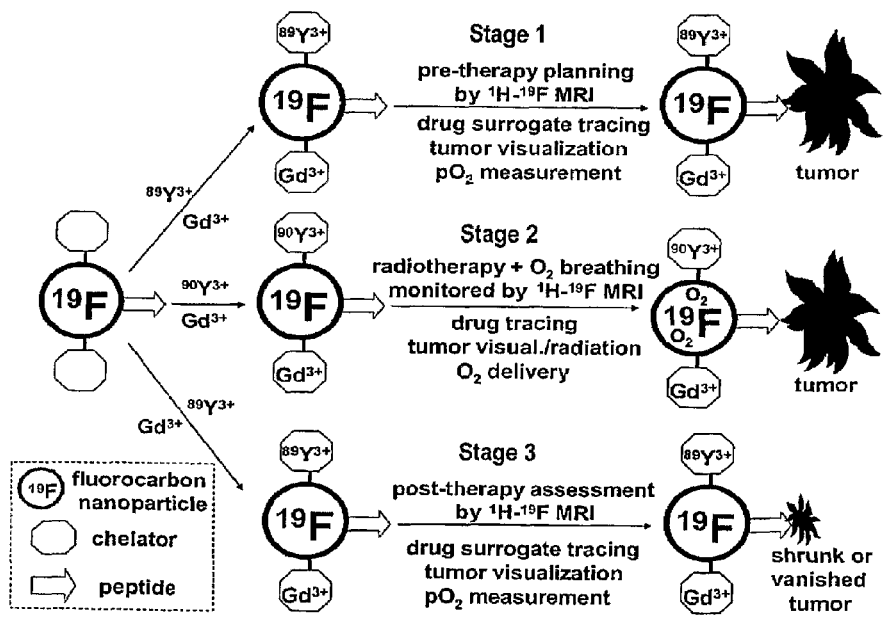
FIG. 2 shows a schematic of a multifunctional delivery vehicle for image-guided targeted radiotherapy. The fluorocarbon nanoparticle, the chelators, and the peptide are not drawn in proportion. In the diagram, each nanoparticle carries two chelators and one targeting peptide. Each nanoparticle can carry multiple chelators and targeting peptides.

As shown in FIG. 2, a multifunctional delivery vehicle can be used in three stages of targeted radiotherapy: pre-therapy planning, radiotherapy stage and post-therapy assessment.

a. Stage 1

At the pre-therapy planning stage (Stage 1), the delivery vehicle can help with two things. First, it can help with patient selection. This is accomplished by measuring local $pO_2$ via $^{19}$F MR relaxometry. Once the patient is selected, it can help with individualizing treatment plans by obtaining patient-specific pharmacokinetic information. This is accomplished by tracing the drug surrogate via $^{19}$F MR and visualizing the tumor via $^1$H MR imaging. The aim is to determine whether tumor targeting is achieved and whether the overall biodistribution of the drug is acceptable. The feasibility of $^{19}$F MRI to trace fluorocarbon nanoparticles or fluorinated drugs in vivo has been demonstrated by several previous studies [Meyer, K. L., Carvlin, M. J., Mukherji, B., Sloviter, H. A. & Joseph, P. M. Fluorinated blood substitute retention in the rat measured by fluorine-19 magnetic resonance imaging. Invest. Radiol. 27, 620-627, 1992; Kimura, A., Narazaki, M., Kanazawa, Y. & Fujiwara, H. $^{19}$F magnetic resonance imaging of perfluorooctanoic acid encapsulated in liposome for biodistribution measurement. Magn. Reson. Imag. 22, 855-860, 2004; Schlemmer, H. P., Becker, M., Bachert, P., Dietz, A., Rudat, V., Vanselow, B., Wollensack, P., Zuna, I., Knopp, M. V., Weidauer, H., Wannenrmacher, M. & van Kaick, G. Alterations of intratumoral pharmacokinetics of 5-fluorouracil in head and neck carcinoma during simultaneous radiochemotherapy. Cancer Res. 59, 2363-2369, 1999; Brix, G., Bellemann, M. E., Haberkom, U., Gerlach, L. & Lorenz, W. J. Assessment of the biodistribution and metabolism of 5-fluorouracil as monitored by $^{18}$F PET and $^{19}$F MRI: a comparative animal study. Nucl. Med. Biol. 23, 897-906, 1996; Brix, G., Schlicker, A., Mier, W., Peschke, P. & Bellemann, M. E. Biodistribution and phamacokinetics of the $^{19}$F-labeled radiosensitizer 3-aminobenzamide: assessment by $^{19}$F MR imaging. Magn. Reson. Imag. 23, 967-976, 2005].

At the pre-therapy planning stage, the cold surrogate can be given at a dose that will saturate the receptor sites in normal tissues but not in tumor tissues. This protects the normal tissues from radiation damage but still leaves the tumor tissue vulnerable. Indeed, it is a standard practice in targeted radiotherapy to first give a cold dose of drug surrogate to protect the normal tissues from radiation [Drug Label Information for Zevalin® and Bexxar®. Available at Drugs@FDA.].

Currently in targeted radiotherapy (Zevalin®, Bexxar® and OctreoTher®), pre-therapy imaging is achieved via nuclear imaging (γ-scintigraphy) [Drug Label Information for Zevalin® and Bexxar®. Available at Drugs@FDA.; Bushnell, et al., Evaluating the clinical effectiveness of 90Y-SMT 487 in patients with neuroendocrine tumors. J. Nucl. Med. 44, 1556-1560, 2003; Wahl, R. L. Tositumomab and 131I therapy in non-Hodgkin's lymphoma. J. Nucl. Med. 46 (Suppl. 1), 128S-140S, 2005; Otte, A., Herrmann, R., Heppeler, A., Behe, M., Jermann, E., Powell, P., Maecke, H. R. & Muller, J. Yttrium-90 DOTATOC: first clinical results. Eur. J. Nucl. Med. 26, 1439-1447, 1999; Paganelli, et al., Receptor-mediated radiotherapy with 90Y-DOTA-D-Phe1-Tyr3-octreotide. Eur. J. Nucl. Med. 28, 426-434, 2001]. This can have two shortcomings. First, nuclear imaging typically increases the radiation burden to both patient and health care providers. This extra radiation burden is worsened if multiple rounds of imaging are needed. In the present approach, nuclear imaging is replaced by MR imaging. Second, in the case of Zevalin® and OctreoTher®, nuclear imaging is done via a surrogate radio-nuclide, $^{111}In^{3+}$, a γ-emitter [Drug Label Information for Zevalin® and Bexxar®. Available at Drugs@FDA.; Bushnell, et al., Evaluating the clinical effectiveness of 90Y-SMT 487 in patients with neuroendocrine tumors. J. Nucl. Med. 44, 1556-1560, 2003; Otte, A., Herrmann, R., Heppeler, A., Behe, M., Jermann, E., Powell, P., Maecke, H. R. & Muller, J. Yttrium-90 DOTATOC: first clinical results. Eur. J. Nucl. Med. 26, 1439-1447, 1999; Paganelli, et al., Receptor-mediated radiotherapy with 90Y-DOTA-D-Phe1-Tyr3-octreotide. Eur. J. Nucl. Med. 28, 426-434, 2001]. The reason is that $^{90}Y^{3+}$ is a pure β-emitter and hence not suited for nuclear imaging. The working assumption is that the $^{90}Y^{3+}$-based drug and the $^{111}In^{3+}$-based surrogate have identical biodistribution. However, as a result of differences in their coordination chemistry [Liu, S., Pietryka, J., Ellars, C. E. & Edwards, D. S. Comparison of yttrium and indium complexes of DOTA-BA and DOTA-MBA: models for 90Y- and 111In-labeled DOTA-biomolecule conjugates. Bioconjugate Chem. 13, 902-913, 2002], this assumption is not always valid as demonstrated by several in vivo studies [Canera, et al., Eur. J. Nucl. Med. 21, 640-646, 1994; Lövqvist, et al., PET imaging of 86Y-labeled anti-LewisY monoclonal antibodies in a nude mouse model: comparison between 86Y and 111In radiolabels. J. Nucl. Med. 42, 1281-1287, 2001]. Hence, there is an element of uncertainty associated with this $^{111}In^{3+}$-based surrogate approach for biodistribution evaluation. In the disclosed approach, $^{89}Y^{3+}$ replaces $^{111}In^{3+}$ as the surrogate for $^{90}Y^{3+}$. Since $^{90}Y^{3+}$ and $^{89}Y^{3+}$ are isotopes, they have identical chemistry and hence uncertainty in biodistribution evaluation is minimized if not abolished completely.

b. Stage 2

At the therapy stage (Stage 2), the $^{1}H$-$^{19}F$ MR imaging capacity of the delivery vehicle allows the physician to monitor the radiotherapeutic drug directly in real time. Such real time feedback makes it possible to adjust treatment plans immediately. Currently in targeted radiotherapy, direct observation of the radiotherapeutic drug is not possible because $^{90}Y^{3+}$ is suitable for nuclear imaging.

Also, at the therapy stage, the delivery vehicle has the potential to modify the pharmacokinetics and the $pO_2$ profiles of each patient. $pO_2$ modification is achieved via the $O_2$ delivery capacity of fluorocarbon micro-emulsions, as mentioned before. Modification of pharmacokinetics can be achieved by modifying the physicochemical properties of the nanoparticles. Without wishing to be bound by theory, it is believed that the pharmacokinetics of the nanoparticles can be modulated by modulating their physicochemical properties. A well-known example of using nanoparticles to alter drug pharmacokinetics is delivering drugs through the blood-brain barrier via nanoparticles [Koziara, J. M., Lockman, P. R., Allen, D. D. & Mumper, R. J. In situ blood-brain barrier transport of nanoparticles. Pharm. Res. 20, 1772-1778, 2003; Kreuter, J. Nanoparticle systems for brain delivery of drugs. Adv. Drug. Del. Rev. 47, 65-81, 2001].

c. Stage 3

During the post-therapy assessment stage (Stage 3), the delivery vehicle can be used to visualize the residual tumor (via $^{1}H$-$^{19}F$ MR imaging) and evaluate its hypoxic status (via $^{19}F$ MR relaxometry). Such information helps to determine whether the previous round of therapy is effective and whether another round of therapy is needed. If another round of therapy is needed, the post-therapy assessment stage of the previous round automatically becomes the pre-therapy planning stage of the next round. In such multiple-round targeted radiotherapy, a critical factor in determining the timing of the next round of therapy is tumor $pO_2$ [O'Hara, J. A., Goda, F., Demidenko, E. & Swartz, H. M. Effect on regrowth delay in a murine tumor of scheduling spit dose radiation based on direct pO2 measurements by EPR oximetry. Radia. Res. 150, 549-556, 1998; O'Hara, et al., Response to radioimmunotherapy correlates with tumor pO2 measured by EPR oximetry in human tumor xenografts. Radia. Res. 155, 466-473, 2001]. Hence, $pO_2$ measurement plays an important role in the delivery of multi-rounds of targeted radiotherapy.

All the aforementioned functions of the delivery vehicle can be further extended. In terms of imaging, aside from carrying $^{90}Y^{3+}$ and $Gd^{3+}$, the chelators can also carry radionuclides for nuclear imaging (e.g., $^{111}In$ for γ-scintigraphy and $^{86}Y$ for positron emission tomography). In addition to $^{19}F$ MR imaging, fluorocarbon nanoparticles can be used for ultrasound imaging. For example, Optison® is an FDA-approved ultrasound contrast agent based on fluorocarbon microemulsions [Klibanov, A. L. Ligand-carrying gas-filled microbubbles: Ultrasound contrast agents for targeted molecular imaging. Bioconjugate Chem. 16, 9-17, 2005]. In addition to $pO_2$ measurement, $^{19}F$ relaxometry also has the potential for temperature measurement [Berkowitz, B. A., Handa, J. T. & Wilson, C. A. Perfluorocarbon temperature measurements using 19F NMR. NMR in Biomedicine, 5, 65-68, 1992; Mason, R. P., Shukla, H. & Antich, P. P. In vivo oxygen tension and temperature: simultaneous determination using 19F NMR spectroscopy of perfluorocarbon. Magn. Reson. Med. 29, 296-302, 1993]. Hence, these fluorocarbon nanoparticles can be easily converted unto multi-modality and multi-purpose imaging agents. In terms of targeting, more than one targeting molecules can be conjugated to nanoparticle surface as a result of the disclosed modular assembling approach. Hence, the nanoparticles can be converted into multi-targeting delivery vehicles. In terms of drug delivery, the nanoparticles can carry chemo-therapeutic agents in addition to radionuclides (e.g., encapsulation of paclitaxal). Similarly, the nanoparticles can also carry other radiotherapy adjuvant (e.g., nicotamide) or other hypoxia markers (e.g., fluorinated 2-nitro-imidazoles). Hence, the nanoparticles can be converted into multimodal delivery vehicles for combined radio-/chemo-therapy.

9. Nanoparticle Formulation

Figure 3:
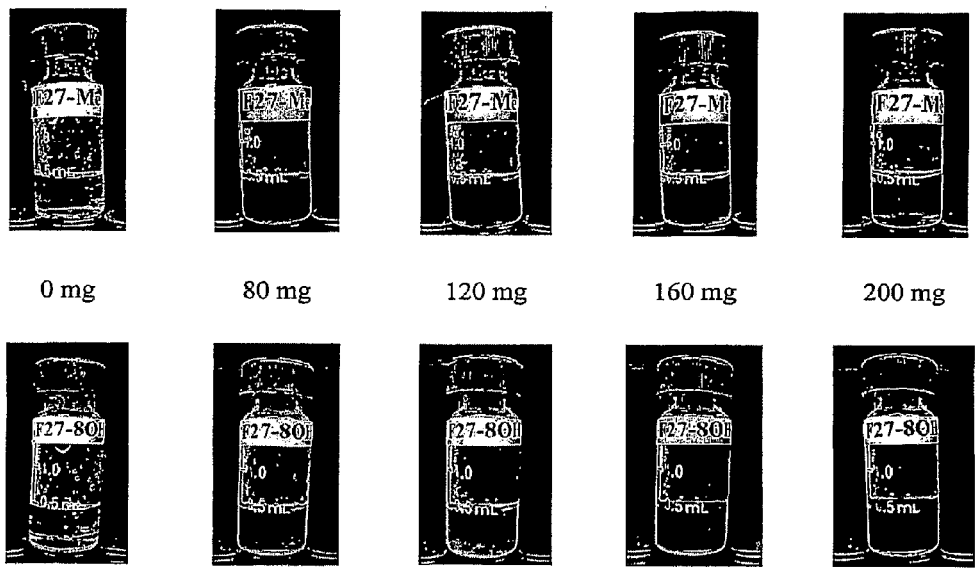
FIG. 3 shows microemulsions (and/or nanoemulsions) formed by two different F-surfactants. The F-oil used here was and analog of compound 4 with —OBn replaced by -Me; the F-surfactant used in the 1st row was compound 10, while that used in the 2nd row was an analog of compound 10 with eighth (—OCH$_2$CH$_2$—) units.

Fluorocarbon nanoparticle emulsions, using the synthesized F-oils and F-surfactants, can be prepared. FIG. 3 shows pictures of two such formulations. In both cases, the starting materials are 200 mg of F-oil ($R_o$=-Me) and 400 mg of PBS. The two F-surfactants have the same end group ($R_s$=—OH). The lengths of the oxyethylene unit for the top row (labeled F27-Me) and the bottom row (labeled F27-8OH) surfactants are 4 and 8, respectively. The F-surfactants were added to the vial gradually and the numbers between the two rows indicate the amount of added F-surfactant (in mg). (The color of the last 4 pictures in the bottom row is distorted somewhat due to the contrast of the wall which does not appear in other picture.) From visual observation, it is clear that different surfactants lead to different emulsions (one clear and one turbid), indicating that nanoparticle properties can be adjusted by modifying structures of F-oils and F-surfactants.

Figure 4:
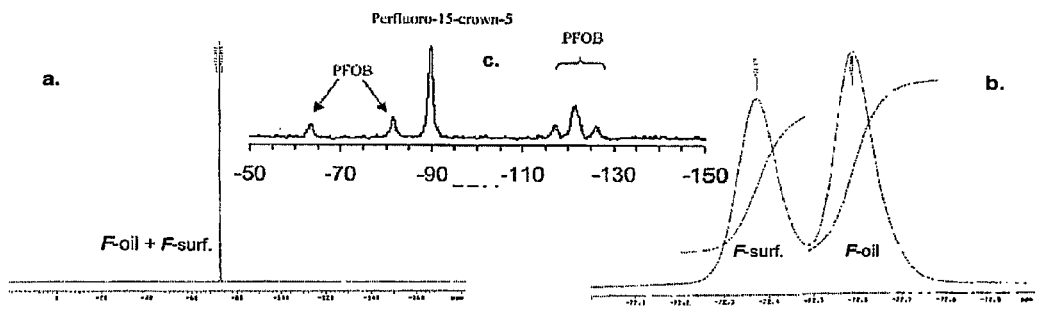
FIG. 4 shows

FIG. 4 shows the $^{19}$F NMR spectra of fluorocarbon nanoparticles for one representative spectrum. In the microemulsion sample, the $^{19}$F signals are very sharp (peak width is about 0.1 ppm), but the $^{19}$F signals in published works are much broader with peak width on the order of 2-3 ppm, about 20-30 time broader than the microemulsion sample. Without wishing to be bound by theory, it is believed that the broadness of the $^{19}$F signals in the published work is caused by the broadness of the size distribution of the nanoparticles [Winter, et al., Improved molecular imaging contrast agent for detection of human thrombus. Magn. Reson. Med. 50, 411-416, 2003]. Regardless of origin, broad $^{19}$F NMR signals lead to reduced $^{19}$F MRI sensitivity. Hence, the present fluorocarbon nanoparticles have a much higher sensitivity for the same amount of $^{19}$F content.

Figure 5:
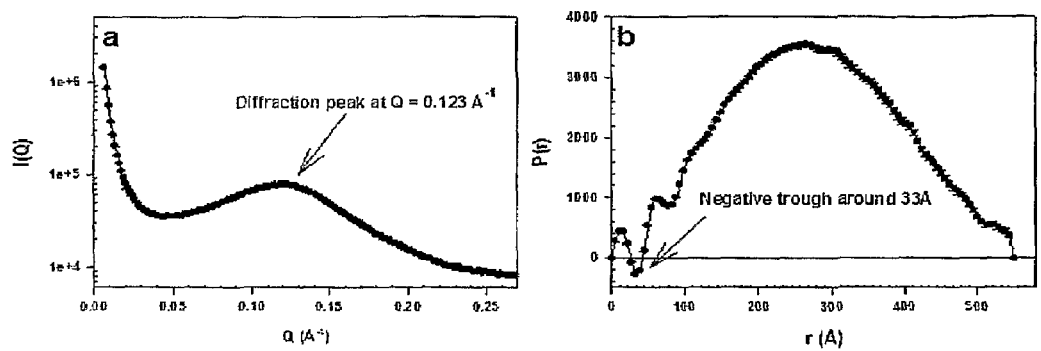
FIG. 5 shows the SAXS analysis of fluorocarbon nanoparticles.

SAXS has been used to characterize the size of the nanoparticle formulation. FIG. 5 presents the SAXS analysis results. The nanoparticle was made of an F-oil (300 mg, $R_o$=-Me), an F-surfactant (200 mg, $R_s$=—$NH_3^+$, j=4) and PBS (600 mg). a. Scattering intensity I(Q) vs. amplitude of the scattering vector Q. The diffraction peak maximum at 0.123 Å$^{-1}$ indicates long-range structural order on the order of 51 Å (=2π/0.123 Å). The origin of this diffraction peak is still under investigation. b. Pair-wise scattering distribution function P(r) vs. pair-wise distance. The radius of the nanoparticle is given by the position of the negative trough, which is 33 Å. Hence, the average diameter of the nanoparticles in this formulation is about 6.6 nm. The large broad peak in b. indicates strong inter-particle interaction, consistent with the positively charged status of the F-surfactant.

The fluorocarbon nanoparticles can be self-assembled from fluorocarbon modules with the inner core made of F-oils and the outer shell made of F-surfactants. The design and selection of F-oils and F-surfactants take both chemical and biological needs into consideration.

a. Nanoparticle Design

Chemically, the design takes four things into consideration. First, signal for $^{19}$F MR imaging. Second, signal for $^{19}$F oximetry. Third, nanoparticle stability. Fourth, derivatizability with chelators and peptides. Biologically, the design takes pharmacokinetics, biocompatibility, and toxicity into consideration. While the chemical requirements can be more easily translated into specifics of molecular design, biological requirements are typically met on a trial-and-error basis. Hence a strategy to meet the biological requirements is to make the structures of the F-oils and F-surfactants amenable to systematic variation. Nonetheless, some rudimentary measures, based on existing knowledge, are taken at the onset of molecular design to meet biological requirements.

For $^{19}$F MR imaging, a single sharp peak is preferred. In one aspect, this requires that all the fluorine atoms in a fluorocarbon module are indistinguishable (i.e., symmetric molecular construct). This requirement can rule out chain-like molecules such as perfluorooctyle bromide because the $^{19}$F signal splits [Morawski, et al., Quantitative "magnetic resonance immunohistochemistry" with ligand-targeted 19F nanoparticles. Magn. Reson. Med. 52, 1255-1262, 2004]. For $^{19}$F oximetry, —$CF_3$ is significantly more sensitive than —$CF_2$-sensitive toward $pO_2$ [Mason, R. P. Non-invasive physiology: 19F NMR of perfluorocarbons. Art. Cell, Blood Subs., and Immob. Biotech. 22, 1141-1153, 1994]. This requirement can rule out macrocyclic molecules such as per-fluoro-15-crown-5 which contains cyclically symmetric —$CF_2$— groups. As a result, a series of spherically symmetric F-oil molecules containing multiple —$CF_3$ groups can be preferred.

As can be seen below, the F-oils are heavily or highly fluorinated but not necessarily perfluorinated, i.e., they can have a hydrocarbon portion. This design feature is based on biocompatibility and toxicity considerations. It is known that in order for the F-oil molecules to be excreted efficiently from the body, certain lipophilicity can be needed [Riess, J. G. Oxygen carriers ("blood substitutes")-raison d'etre, chemistry and some physiology. Chem. Rev. 101, 2797-2919, 2001]. The hydrocarbon portion of F-oils provides this lipophilicity. Further, the F-oils have a variable portion $R_o$. This flexibility allows us to further adjust it lipophilicity. However, even though the F-oils are not per-fluorinated, their fluorine content (F %~65%) is comparable to that of perfluorocarbons used as blood substitutes (e.g., perfluorooctyl bromide, or PFOB, F %=64.6%). Hence, their $O_2$-carrying capacities are expected to be comparable to that of PFOB because such capacities depend primarily on fluorine content [Riess, J. G. Oxygen carriers ("blood substitutes")-raison d'etre, chemistry and some physiology. Chem. Rev. 101, 2797-2919, 2001].

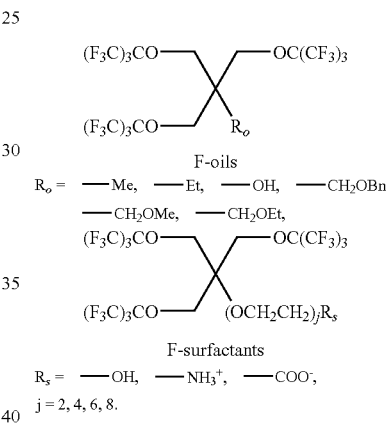

Only three representative F-surfactant structures are shown here. F-surfactants with other types of terminal groups (e.g., $R_s$=—$CNMe_2^+$) can also be prepared. Like the design of F-oils, the design of F-surfactants also takes chemical and biological requirements into consideration. One salient feature is that the fluorocarbon portion of F-surfactants can be identical to the fluorocarbon portion of F-oils. This is based on stability considerations. Without wishing to be bound by theory, it is believed that shape matching between the oil and the surfactant can lead to enhanced microemulsion stability, based on molecular theory of the liquid state [Chandler, D. Structures of molecular liquids. Annu. Rev. Phys. Chem. 29, 441-471, 1978]. In terms of derivatizability with peptides, one version of F-surfactants has carboxylate (—$COO^-$) as the end group. This allows it to be conjugated to the N-terminus of a peptide during solid-phase synthesis without any protection group needed.

To meet biological requirements, the hydrocarbon tail of the F-surfactants has three variable portions. The stem of the hydrophilic tail is made of an oligooxyethylene segment, (—$OCH_2CH_2$—)$_j$. The length of this segment is j. When j is small (in the range from 2 to about 10), for each F-surfactant, j is a fixed number. In such a case, each F-surfactant is a pure compound, not a mixture. A mixture of such pure compounds can be prepared simply by mixing these pure compounds. When j is large (>>10), then j does not have a fixed value as the surfactant will be prepared from polymers. In such a case, each surfactant is a mixture of multiple compounds. Fluorinated surfactants with oligooxyethylene segments as the hydrophilic moiety have been used extensively for the emulsification of fluorocarbons [Mathis, G., Leempoel, P., Ravey, J.-C., Selve, C. & Delpuech, J-J. A novel class of non-ionic microemulsions: fluorocarbons in aqueous solutions of fluorinated poly(oxyethylene) surfactants. J. Am. Chem. Soc. 106, 6162-6171, 1984; Cui, Z., Fountain, W., Clark, M., Jay, M. & Mumper, R. J. Novel enthanol-fluorocarbon microemulsions for topical genetic immunization. Pharm. Res. 20, 16-23, 2003]. Such fluorinated oligooxyethylene surfactants not only make fluorocarbon microemulsions more stable than EYP-based ones, but also make them more biocompatible by reducing phagocytosis [Peng, C.-A. & Hsu, Y.-C. Fluoroalkylated polyethylene glycol as potential surfactant for perfluorocarbon emulsion. Art. Cells, Blood Subs., and Immob. Biotech. 29, 483-492, 2001; Hsu, Y.-C. & Peng, C.-A. Diminution of phagocytosed perfluorocarbon emulsions using perfluoroalkylated polyethylene glycol surfactant. Biochem. Biophys. Res. Comm. 283, 776-781, 2001]. In terms of length, a recent study on fluorinated oligooxyethylene surfactants demonstrated that the oxyethylene segment starts to curl around each other and form micelles in water when the average segment length is longer than 8.7 [Li, Y., Chen, Z.-Q., Tian, J., Zhou, Y.-B., Chen, Z.-X. & Liu, Z.-J. Synthesis of novel type of hybrid fluorocarbon ionic surfactants containing polyoxyethylene chain. J. Fluorine Chem. 126, 888-891, 2005]. In certain aspects, the length of the oxyethylene segment is limited to 8 units. The short length is made up by high density, i.e., every surfactant molecule has a ($-OCH_2CH_2-$)$_j$ segment.

The second variable portion of the hydrocarbon tail of F-surfactants is the end group following the ($-OCH_2CH_2-$)$_j$ segment. To modulate the physicochemical properties of the nanoparticles, terminal groups of F-surfactants can be positively charged (e.g., $-NH_3^+$), negatively charged (e.g., $-COO^-$) and neutral (e.g., $-OH$). The biological relevancy of this type of variations is that the pharmacokinetics of fluorocarbon microemulsions can be adjusted through the adjustment of the physicochemical properties of the emulsifiers [Tsuda, Y., Yamanouchi, K., Okamoto, H., Yokoyama, K. & Heldebrant, C. Intravascular behavior of a perfluorochemical emulsion. J. Pharmacobiodyn. 13, 165-171, 1990; Obraztov, V. V., Kabalnov, A. S., Makarov, K. N., Gross, U., Radeck, W. & Rudiger, S. On the interactions of perfluorochemical emulsions with liver microsomal membranes. J. Fluorine Chem. 63, 101-111, 1993; Klein, D. H., Jones, R. C., Keipert, P. E., Luena, G. A., Otto, S. & Weers, J. G. Intravascular behavior of perflubron emulsions. Collods & Surf. A: Physicochem. Engineering Aspects, 84, 89-95, 1994].

The third variable is dendron type of branching and this is best represented by the generation number k. The number of terminal branches is given by $2^k$ (i.e., for F-surfactants with one, two, four, eight and sixteen terminal branches, k=0, 1, 2, 3, and 4, respectively).

Finally, for metallic ion complexation and tumor targeting, the terminal groups of certain surfactants can be conjugated to DOTA (F-surfactant-DOTA) or octreotide (F-surfactant-octreotide).

In one aspect, the compounds and/or compositions relate to a nanoparticle comprising at least one of the disclosed compounds. For example, in the nanoparticle, $R_4$ can comprise a moiety having the structure:

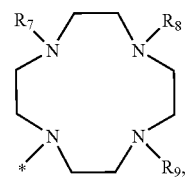

wherein $R_7$, $R_8$, and $R_9$ are, independently, H, $CH_2CO_2H$, or alkyl.

In a further aspect, the compound can comprise the structure:

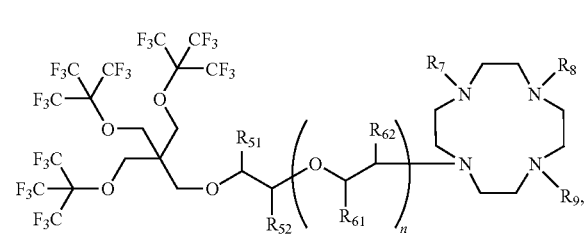

wherein n is 0 or a positive integer; wherein $R_{51}$, $R_{52}$, $R_{61}$, and $R_{62}$ are, independently, H or alkyl; and wherein $R_7$, $R_8$, and $R_9$ are, independently, H, $CH_2CO_2H$, or alkyl. In a further aspect, the nanoparticle can further comprise a metallic radionuclide (e.g., $^{90}Y^{3+}$) or non-ratioactive metallic ions (e.g., $Gd^{3+}$). In a further aspect, $R_4$ can comprise a moiety having the structure:

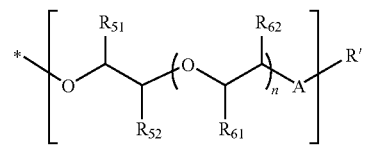

wherein n is 0 or a positive integer; wherein $R_{51}$, $R_{52}$, $R_{61}$, and $R_{62}$ are, independently, H or alkyl; wherein A is O, S, or amino; and wherein R' comprises a peptide. In a further aspect, the nanoparticle can comprises a compound comprising the structure:

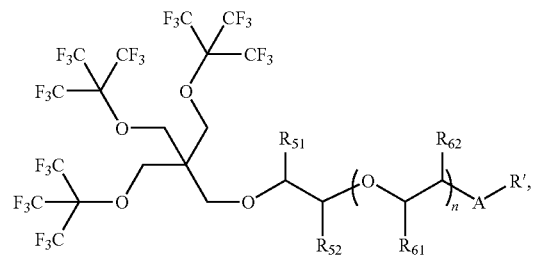

wherein n is 0 or a positive integer; wherein $R_{51}$, $R_{52}$, $R_{61}$, and $R_{62}$ are, independently, H or alkyl; wherein A is O, S, or amino; and wherein R' comprises a peptide.

The peptide can comprise octreotide and/or its various analogs (such as, but not restricted to, lanreotide, vapreotide, etc.). Other peptides (such as, but not restricted to, bombesin, vascoactive intestinal peptide, cholecystokinin, substance, P, etc.) can also be used for this purpose (L. Bodei, G. Paganelli & G. Mariani, Receptor radionuclide therapy of tumors: a road from basic research to clinical applications. J. Nucl. Med. 47, 375-377, 2006). Further, anybody molecules (such as, but not restricted to, rituximab, ibritumomab, tositumomab, trastuzuamb) and other targeting molecules (e.g., siRNA) are also suitable.

b. Nanoparticle Formulation

The nanoparticles can be formulated as microemulsions. Prior to nanoparticle formulation, each module can be purified. The F-surfactant-DOTA modules complex with $Gd^{3+}$ first, using standard protocols [Heppeler, et al., Radiometal-labelled macrocyclic chelator-derivatized somatostatin analogue with superb tumour-targeting properties and potential for receptor-mediated internal radiotherapy. Chem. Eur. J. 5, 1974-1981, 1999]. The complexation product, F-surfactant-DOTA-$Gd^{3+}$, can be further purified by HPLC and verified by mass spectrometry before use.

For nanoparticle formulation, mixture of the various modules can be passed through a high-pressure microfluidic device (model M-110S from Microfluidics, Newton, Mass.), following published procures [Morawski, et al., Quantitative "magnetic resonance immunohistochemistry" with ligand-targeted 19F nanoparticles. Magn. Reson. Med. 52, 1255-1262, 2004; Lanza, et al., A novel site-targeted ultrasonic contrast agent with broad biomedical application. Circulation, 94, 3334-3340, 1996]. The size of the nanoparticle can be modulated by adjusting the ratio of charged vs. neutral surfactants during formulation as high surface charge can result in electrostatic repulsion and hence reduced size. The intended radius of the nanoparticles is between 10-50 nm.

The dominant component of the outer shell of the nanoparticles can be neutral F-surfactants ending with the —OH group. Positively or negatively charged F-surfactants can be added to the formulation as modulators of physicochemical properties (size, surface charge, stability, etc.). Adjustment of the physicochemical properties of the nanoparticles can be achieved in a combinatorial fashion by combining different modules and by varying the molar ratios of different modules. For example, adding charged surfactants to fluorocarbon emulsions can enhance stability by preventing flocculation [Oleksiak, C. B., Habif, S. S. & Rosano, H. L. Flocculation of perfluorocarbon emulsions. Colloids Surf. A Physicochem. Engineering Aspects, 84, 71-79, 1994]. In addition, data indicate that properties of the microemulsions can be modulated by varying structures of F-surfactants (FIG. 3, page 40).

c. Nanoparticle Characterization

Basic features of the $^{19}F$, including chemical shift values, number of peaks, peak width, $T_1$ and $T_2$, can be characterized by NMR spectroscopy, using standard procedures. This serves as a quick screening in that formulations with broad $^{19}F$ peaks can be abandoned.

Nanoparticles can be visualized using freeze-fracture electron microscopy, using standard procedure [Postel, et al., Fluorocarbon/lecithin emulsions: identification of EYP-coated fluorocarbon droplets and fluorocarbon-empty vesicles by freeze-fracture electron microscopy. Biochim. Biophys. Acta, 1086, 95-98, 1991]. This can give a crude but quick estimation the size and heterogeneity of nanoparticles. Formulations leading to much heterogeneity can be abandoned.

The average size of the nanoparticles can be determined by small angle X-ray scattering (SAXS) technique. X-rays are scattered by electrons, the scattering densities are simply the sum of the number of electrons per unit volume. Due to the high electron density of the fluorine atom, fluorinated nanoparticles are particularly suited to be characterized by SAXS [Riess, J. G. Fluorous micro- and nanophases with a biomedical perspective. Tetrahedron, 58, 4113-4131, 2002].

Data can be measured using the SAXS instrument currently at the University of Utah and described in [Heidorn, D. B. & Trewhella, J. Comparison of the crystal and solution structures of calmodulin and troponin C. Biochemistry, 27, 909-915, 1988]. 20 µl of a fluorocarbon microemulsion sample can be loaded into a capillary of 1 mm diameter. The sample can be spun down in to the capillary and the scattering measurements can be done at 25° C. (maintained by the sample water bath). The x-ray scattering experiment typically takes minutes to hours. Hence, it measures the average sizes of the nanoparticles.

Data analysis follows established procedures on analyzing SAXS data of micro-emulsions [Wormuth, K. R. & Kaler, E. W. Microemulsifying polar oils. J. Phys. Chem. 93, 4855-4861, 1989; Pons, R., Ravey, J. C., Sauvage, S., Stebe, M. J., Erra, P. & Solans, C. Structural studies on gel emulsions. Colloids & Surf. A: Physicochem. Engineering Aspects, 76, 171-177, 1993]. Signal intensity in SAXS depends on the electron density contrast between a particle and its surrounding medium. Electron density is calculated by dividing the number of electrons of molecule by its van der Waals volume (the van der Waals volume of a molecule is calculated by adding up the van der Waals volumes of its constitutive groups, according to [Lepori, L. & Gianni, P. Partial molar volumes of ionic and nonionic organic solutes in water: a simple additivity scheme based on the intrinsic volume approach. J. Solution Chem. 29, 405-447, 2000)). For the present nanoparticles, electron densities of the inner score (made of F-oils and the fluorocarbon head of F-surfactants) and the outer shell (made of oxyethylene segments) are 0.85e/Å$^3$ and 0.57e/Å$^3$, respectively. The electron density of water is 0.33e/Å$^3$. As a result, the electron density contrast (calculated as the square of the difference between the electron density of the component and that of $H_2O$) between the fluorocarbon inner core and $H_2O$ is 4.7 times greater than the electron density contrast between the oxyethylene outer shell and $H_2O$. This constitutes the basis for separately obtaining the radius of the inner core and the radius of the entire nanoparticle.

Specifically, to obtain the radius of the fluorocarbon inner core, KCl is added to PBS buffer to match the electron density of the oxyethylene outer shell. This way, the outer shell makes no contribution to scattering, and the radius of the inner core, $r_{core}$, is obtained. To obtain the radius of the entire nanoparticle, no KCl would be added. In this case, both the inner core and the outer shell make contribution to the scattering intensity and consequently one can obtain the radius of the entire nanoparticle, $r_{NP}$.

From $r_{core}$, the average volume of the fluorocarbon inner core, $v_{core}$, can be calculated as:

$$v_{core} = \frac{4\pi}{3}(r_{core})^3 \quad (1)$$

From $r_{NP}$, the average volume of the entire nanoparticle, $v_{NP}$, can be calculated in a similar fashion. Such volume information can be useful in determining nanoparticle concentration.

d. Nanoparticle Stability

In vitro stability of the microemulsion can be evaluated by following the average size of the nano-particles over time, using SAXS. This has proven to be an effective method in monitoring fluorocarbon emulsion stability [Trevino, L., Solé-Violan, L., Daumur, P., Devallez, B., Postel, M. & Riess, J. G. Molecular diffusion in concentrated fluorocarbon emulsions and its effect on emulsion stability. New J. Chem. 17, 275-278, 1993].

e. Nanoparticle Concentration

Nanoparticle concentration can be calculated using the following equation [Morawski, et al., Quantitative "magnetic resonance immunohistochemistry" with ligand-targeted 19F nanoparticles. Magn. Reson. Med. 52, 1255-1262, 2004]:

$$[NP] = \frac{V_{core}}{v_{core} \cdot V_E \cdot N_{av}} \quad (2)$$

where $v_{core}$ is the volume of the fluorocarbon inner core of individual nanoparticles (determined by SAXS), $V_{core}$ is the total volume of the fluorocarbon phase, $V_E$ is the volume of the emulsion and $N_{av}$ is Avogadro's number. $V_{core}$ is calculated as: $V_{oil,add} + f_F \cdot V_{surf,add}$, where $V_{oil,add}$ and $V_{surf,add}$ are volumes of added F-oil and F-surfactant, respectively, and $f_F$ is the volume fraction of the fluorocarbon head of the F-surfactant. $f_F$ can be calculated from the van der Waals volumes of the constitutive groups of the F-surfactant [Lepori, L. & Gianni, P. Partial molar volumes of ionic and nonionic organic solutes in water: a simple additivity scheme based on the intrinsic volume approach. J. Solution Chem. 29, 405-447, 2000].

In the case that phase separation occurs, meaning only part of added F-oil and F-surfactant are incorporated into the nanoparticles, the fluorocarbon concentration in each phase can be determined by NMR spectroscopy, using a known amount of $CF_3$-containing compound (e.g., trifluoroethanol, $CF_3CH_2OH$) as an internal standard. From this concentration and the volume of each phase, the fraction of incorporated Foil and F-surfactant can be calculated. Then, volumes of incorporated Foil and F-surfactant, $V_{oil,incorp.}$ and $V_{surf,incorp.}$, respectively, can be calculated. These volumes can then be used to calculate $V_{core}$ as: $V_{oil,incorp.} + f_F \cdot V_{surf,incorp.}$.

f. Nanoparticle Payload

The concentration of $Gd^{3+}$ in an emulsion preparation can be determined by inductively coupled plasma optical emission spectrometry (ICP-OES). This method has been used routinely in determining $Gd^{3+}$ content in contrast agent samples [Zong, Y., Wang, X., Goodrich, K. C., Mohs, A., Parker, D. & Lu, Z. R. Contrast enhanced tumor MRI with new biodegradable macromolecular Gd(III) complexes in mice. Magn. Reson. Med. 53, 835-842, 2005]. Samples of known $Gd^{3+}$ concentrations can be used as standards for calibration.

The concentration of octreotide in each microemulsion sample can be determined by UV absorption spectroscopy. Trp, Tyr and the disulfide bond together gives an extinction coefficient of 7110 $M^{-1} \cdot cm^{-1}$ at 280 nm [Gill, S. C. & von Hippel, P. H. Calculation of protein extinction coefficients from amino acid sequence data. Analyt. Biochem. 182, 319-326, 1989]. Note that no other components of the nanoparticles absorb UV light around 280 nm. If needed, the sample can be diluted by 7M guanidinium chloride solution to dissolve the nanoparticle. If uncertainty still arises, the peptide concentration can be further determined by amino acid analysis (in which the peptide is broken into amino acids by concentrated HCl) and nitrogen analysis (in which the peptide is digested completely by concentrated $HClO_4$ and the amount of release ammonium is determined). For example, see [Yu, Y., Makhatadze, G. I., Pace, C. N. & Privalov, P. L. Energetics of ribonuclease T1 structure. Biochemistry, 33, 3312-3319, 1994]. From the concentration ratio of $Gd^{3+}$ vs. nanoparticle and that of octreotide vs. nanoparticle, the payload $Gd^{3+}$ and octreotide payload per nanoparticle can be determined.

g. Nanoparticle Biodistribution

For preliminary biodistribution evaluation, the retention of the nanoparticle in the tumor and spleen and liver can be determined. Spleen and liver are selected because these are the organs where fluorocarbons accumulate through the reticuloendothelial system [Mason, R. P., Antich, P. P., Babcock, E. E., Gerberich, J. L. & Nunnally, R. L. Perfluorocarbon imaging in vivo: A 19F MRI study in tumor-bearing mice. Magn. Reson. Imag. 7, 475-485, 1989; Riess, J. G. Oxygen carriers ("blood substitutes")-raison d'etre, chemistry and some physiology. Chem. Rev. 101, 2797-2919, 2001; Ratner, A. V., Hurd, R., Muller, H. H., Bradley-Simpson, B., Pitts, W., Shibata, D., Sotak, C. & Young, S. W. 19F magnetic resonance imaging of the reticuloendothelial system. Magn. Reson. Med. 5, 548-554, 1987]. In the R33 phase, more details biodistribution studies in involving other tissues and organs (blood, kidneys, brain, lung, etc.) can be determined.

The biodistribution evaluation compares the tumor-to-organ ratios of targeted versus non-targeted nanoparticles. Three different nanoparticles and their non-targeted counterparts (hence, a total of six samples) can be evaluated. The three nanoparticles can have neutral, positively and negatively charged F-surfactants, respectively ($R_s$=—OH, —$NH_3^+$ and $COO^-$). In one aspect, the non-targeted nanoparticles can be decorated with DOTA-$Gd^{3+}$, but no peptide. In a further aspect, a more rigorous control in which nanoparticles decorated with a non-targeting octreotide analog can be used.

h. Tumor Cell Lines and Animal Models

For biodistribution and imaging studies, the well characterized AR4-2J pancreatic carcinoma cell line (commercially available from American Type Cell Culture, ATCC) [Viguerie, N., Tahiri-Jouti, N., Esteve, J. P., Clerc, P., Logsdon, C., Svoboda, M., Susini, C., Vaysse, N. & Ribet, A. Functional somatostatin receptors on a rat pancreatic acinar cell line. Am. J. Physiol. 255, G113-G120, 1988] can be used. This cell line is selected because of its exclusive constitutive expression of type 2 somatostatin receptor (sstr2) [Froidevaux, et al., Differential regulation of somatostatin receptor type 2 (sst 2) expression in AR4-2J tumor cells implanted into mice during octreotide treatment. Cancer Res. 59, 3652-3657, 1999]. sstr2 is the receptor subtype most commonly over-expressed by neuroendocrine tumors and is the targeted for octreotide and its analogs [Kaltsas, G. A., Papadogias, D., Makras, P. & Grossman, A. B. Treatment of advanced neuroendocrine tumours with radiolabelled somatostatin analogues. Endocrine-Related Cancer, 12, 683-699, 2005]. AR4-2J cell line is derived from Wistar rats.

This cell line is implanted subcutaneously in Lewis rats. Lewis rats are suitable for this work because they are an inbred strain derived from the Wistar rat and therefore exhibit little genetic variability. Tumor models using this cell line in Lewis rats are already established [Storch, et al., J. Nucl. Med. 46, 1561-1569, 2005].

$10^7$ AR4-2J pancreatic tumor cells can be injected subcutaneously in 6-week old Lewis rats [Storch, et al., J. Nucl. Med. 46, 1561-1569, 2005]. Two weeks after tumor inoculation, the rats can be injected via the tail vein with nanoparticles at a $^{19}F$ dose of 50 mmole/kg (for rationale on dose selection, see the following section). As stated above, a total of six samples can be tested. For each sample, 6 rats (3 male/3 female) can be used. 3, 7 and 14 days after nanoparticle injection, animals from each group can be sacrificed (see section F for details of animal protocols). Tumor implants, liver and spleen can be collected from each animal for biodistribution assays. The total number of animals used is ca. 110.

A sample can be mixed with ultra pure water and homogenized at 9500 rpm for several minutes until there was no visible solid tissue. Each sample can be halved equally in so that the amount of nanoparticles in each homogenized sample can be determined by two independent methods. The first one determines the amount of fluorocarbon content. The second one determines the amount of $Gd^{3+}$.

To determine fluorocarbon content, a known amount trifluoroethanol ($CF_3CH_2OH$) can be added to the sample as internal reference. The sample can then be loaded into an NMR tube and the $^{19}F$ signal intensity can be determined by NMR spectroscopy. $^{19}F$ signal intensity can be converted into fluorocarbon concentration using the internal reference as the standard. This method has been used previously to determine the biodistribution of fluorocarbon emulsions in animal models [Zarif, et al., Biodistribution of mixed fluorocarbon-hydrocarbon dowel molecules used as stabilizers of fluorocarbon emulsions: a quantitative study by fluorine nuclear magnetic resonance (N). Pharm. Res. 11, 122-127, 1994; McGoron, et al., Art. Cells, Blood Subs., and Immob. Biotech. 22, 1243-1250, 1994].

$Gd^{3+}$ content in each sample can be determined by ICP-OES. This method is used routinely in the determination of $Gd^{3+}$ retention in tissues [Zong, Y., Wang, X., Goodrich, K. C., Mohs, A., Parker, D. & Lu, Z. R. Contrast enhanced tumor MRI with new biodegradable macromolecular Gd(III) complexes in mice. Magn. Reson. Med. 53, 835-842, 2005].

Fluorocarbon and $Gd^{3+}$ tissue retention can be represented by percentage of injected dose per organ. Fluorocarbon content and $Gd^{3+}$ content in each organ can be compared for consistency test, using the $^{19}F$-to-$Gd^{3+}$ ratio in the original microemulsion as the reference point.

An HPLC-MS-based method can be used as an alternative to $^{19}F$ NMR [Hansen, K. J., Clemen, L. A., Ellefson, M. E. & Johnson, H. O. Compound-specific, quantitative characterization of organic fluorochemicals in biological matrices. Environ. Sci. Technol. 35, 766-770, 2001]. This highly sensitive method has been used successfully to determine the concentration of fluorocarbons in human and monkey organs and blood samples [Olsen, G. W., Hansen, K. J., Burris, J. M. & Mandel, J. H. Human donor liver and serum concentrations of per-fluorooctanesulfonate and other perfluorochemicals. Environ. Sci. Technol. 37, 888-891, 2003; Butenhoff, J. L., Kennedy, G. L., Hinderliter, P. M., Lieder, P. H., Jung, R., Hansen, K. J., Gornan, G. S., Noker, P. E. & Thomford, P. J. Pharmacokinetics of perfluorooctanoate in cynomolgus monkeys. Toxicol. Sci. 82, 394-406, 2004].

The dose of fluorocarbon nanoparticles can be based on fluorine content from the F-oil molecules which form the inner core of nanoparticles. F-oils can be the dominant fluorocarbon component of the nanoparticles and $^{19}F$ MRI signal intensity can be determined by contributions from F-oils. Technically, the concentration of this particular $^{19}F$ concentration can be determined by NMR spectroscopy, using a known quantity of trifluoroethanol ($CF_3CH_2OH$) as the standard. From this concentration value, the $^{19}F$ dose in terms of mmole/kg can be determined.

As for dose selection, Table 1 lists $^{19}F$ doses of various fluorocarbon emulsions. $^{19}F$ refers to all the fluorine content in a fluorocarbon microemulsion. Some of the fluorocarbons give a single $^{19}F$ single (e.g., perfluoro-15-crown-5) while others give multiple $^{19}F$ signals (e.g., perfluorooctyl bromide). The $^{19}F$ dose range is from 25 to 598 mmole/kg body weight. Consequently, 50 mmol/kg can be used as the $^{19}F$ dosage.

TABLE 1

| $^{19}F$ doses | | |
|---|---|---|
| Applications | Dose and route | Subjects |
| I. Targeted fluorocarbon microemulsions for $^{19}F$ tumor imaging | | |
| perfluorotributylamine, $C_{12}F_{27}N$ (Schimizu et al., 1987) | 150 mmole $^{19}F/kg^1$, i.v. | mice |
| II. Non-targeted fluorocarbon microemulsions for $^{19}F$ tumor imaging | | |
| perfluorotributylamine, $C_{12}F_{27}N$ (Longmaid et al., 1985) | 363 mmole $^{19}F/kg$, i.v. | rats |
| perfluorooctyl bromide (PFOB), $C_8F_{17}Br$ (Ratner et al., 1988) | 340 mmole $^{19}F/kg$, i.v. | mice |
| mixture of $C_{12}F_{27}N$, $C_{10}F_{18}$ and $C_9F_{21}N$ (Mason et al., 1989) | 450 mmole $^{19}F/kg^1$, i.v | mice |
| III. Non-targeted fluorocarbon microemulsions for $^{19}F$ tumor oximetry | | |
| perfluoro-15-crown-5, $C_{10}O_5F_{20}$ (McIntyre et al., 1999) | 180 mmole $^{19}F/kg$, i.v | mice |
| perfluoro-15-crown-5, $C_{10}O_5F_{20}$ (van der Sanden et al., 1999 a, b) | 145 mmole $^{19}F/kg$, i.v | mice |
| perfluoro-15-crown-5, $C_{10}O_5F_{20}$ (Fan et al., 2002) | 25 mmole $^{19}F/kg^2$, i.v | rats |
| PFOB, $C_8F_{17}Br$ (Shukla et al., 1995) | 284 mmole $^{19}F/kg/$, i.v | rats |
| hexafluorobenzene, $C_6F_6$ (Zhao et al., 2001, 2004; Mason et al., 1998; Hunjan et al., 1998) | 1-5 mmole $^{19}F$/tumor, intra-tumor injection | rats |
| IV. Non-targeted fluorocarbon microemulsions for $O_2$ delivery to tumor | | |
| Fluorosol D, $C_{10}F_{18}$ (Teicher and Rose, 1984a) | 150 mmole $^{19}F/kg^1$, i.v | mice |
| Fluorosol D, $C_{10}F_{18}$ (Rose et al., 1986) | 598 mmole $^{19}F/kg$, i.v | human |

TABLE 1-continued $^{19}$F doses

| Applications | Dose and route | Subjects |
|---|---|---|
| perfluoro-15-crown-5, $C_{10}O_5F_{20}$ (Al-Hallaq et al., 2000) | 146 mmole $^{19}$F/kg, i.v | rats |
| PFOB, $C_8F_{17}Br$ (Thomas et al., 1991; 1995) | 102 mmole $^{19}$F/kg, retro-orbital sinus | mice |

[1]Dose is converted from mmole/mouse to mmole/kg body weight assuming the weight of a mouse is 20 gram.
[2]Dose is converted from mmole/rat to mmole/kg body weight assuming the weight of a rat is 200 gram.

i. Average Radii of the Nanoparticles

For a nanoparticle with an average radius of 25 nm (referring to the fluorocarbon core diameter), $v_{core}$ is $6.55 \times 10^{-23}$ m$^3$. The molar volume of such fluorocarbons is around 0.44 L/mole (calculated from the F-oil with $R_o$=-Me density=1.75 g/mL, M.W.=775). Hence, the number of F-oil molecule per nanoparticle is $9 \times 10^4$. Since each F-oil has, in one aspect, 27 identical fluorine atoms, the number of identical fluorine atoms is $2.5 \times 10^6$/particle. Similarly, for a nanoparticle with a radius of 50 nm, the number of fluorine atoms is $2.0 \times 10^7$/particle. Hence, for nanoparticles in the range of 25 nm-50 nm, the number of fluorine atoms is $2.5 \times 10^6$ to $2.0 \times 10^7$ per particle. The density of sstr2 in the AR4-2J cell line is ca. 10 nM [Froidevaux, et al., Differential regulation of somatostatin receptor type 2 (sst 2) expression in AR4-2J tumor cells implanted into mice during octreotide treatment. Cancer Res. 59, 3652-3657, 1999]. Hence, in vivo $^{19}$F signal density in the tumor can be in the range of 25-200 mM, sufficient for $^{19}$F MR imaging [Morawski, et al., Quantitative "magnetic resonance immunohistochemistry" with ligand-targeted $^{19}$F nanoparticles. Magn. Reson. Med. 52, 1255-1262, 2004]. A previous study reported that at 1.5 T the minimum detectable $^{19}$F level is 30 μM [Schlemmer, et al., Alterations of intratumoral pharmacokinetics of 5-fluorouracil in head and neck carcinoma during simultaneous radiochemotherapy. Cancer Res. 59, 2363-2369, 1999].

j. Pharmacokinetics of Fluorocarbon Nanoparticles

Thorough pharmacokinetic (PK) studies of fluorocarbon nanoparticles can be conducted, using high tumor-to-organ ratio and rapid excretion ($t_{1/2}$ ranging from hours to days, rather than weeks to months) as selection criteria to establish a quantitative relationship between the physicochemical properties (size, charge, peptide and chelator payload, dose, etc.) and the PK profiles of the nanoparticles. Without wishing to be bound by theory, it is believed that, by modulating physicochemical properties of the nanoparticles, their pharmacokinetics can be modulated. A series of $^1$H and $^{19}$F MR imaging experiments can be conducted to evaluate the various functions engineered for selected nanoparticles.

k. Fluorocarbon Nanoparticles as Drug Tracers $^{19}$F MR-based techniques can be implemented for estimation of biodistribution and tissue pharmacokinetics of the fluorocarbon nanoparticles. Accumulation of the nanoparticles in the tumor can be evaluated against liver and spleen, the major organs that non-specifically take up these particles. Without wishing to be bound by theory, it is believed that the targeting moiety on the fluorocarbon nanoparticles enhances the accumulation of the nanoparticles in a tumor significantly compared to those nanoparticles that lacks the targeting capability (i.e., carrying a non-targeting peptide). Signal enhancement in tumor can be increased, for example, ≧30% when the nanoparticle carries a targeting peptide compared to a non-targeting one.

l. Fluorocarbon Nanoparticles as pO$_2$ Probes and O$_2$ Delivery Vehicles

Without wishing to be bound by theory, it is believed that the tumor periphery can have significantly higher pO$_2$ than the tumor center; however, pO$_2$ of tumor center can be enhanced when the animal is breathing carbogen (95% O$_2$ and 5% CO$_2$). Also without wishing to be bound by theory, it is believed that, comparing to carbogen breathing alone (i.e., without nanoparticles), the tumor pO2 can be significantly increased by both carbogen breathing and nanoparticles delivery. Higher tumor-to-organ ratio and better excretion profile can be achieved by modifying the chemistry of the nanoparticles.

m. Non-Targeting Analogs of Octreotide

To verify the effect of targeting on nanoparticle pharmacokinetics, a non-targeted counterpart of each targeted nanoparticle can be prepared for comparison. A targeted nanoparticle is decorated with octreotide (sequence: DPhe1-c[Cys2-Phe3-DTrp-4-Lys5-Thr6-Cys7]-Thr8-NH$_2$), which targets sstr2 with high affinity and specificity. In a non-targeted nanoparticle, octreotide can be replaced by its inactive analog in which L-Thr6, located in the active site of octreotide, is replaced by D-Thr6 (commercially available in protected form). A previous study has demonstrated such an L→D replacement completely abolishes the binding affinity of octreotide toward all somatostatin receptors [Reuter, J. K., Mattern, R.-H., Zhang, L., Morgan, B., Hoyer, D. & Goodman, M. Syntheses and biological activities of sandostatin analogs containing streochemical changes in positions 6 or 8. Biopolymers, 53, 497-505, 2000]. Since these two peptides are otherwise identical, nanoparticles decorated with the L-Thr6→D-Thr6 analog of octreotide constitute a perfect control to verify the effect of octreotide targeting.

n. Pharmacokinetic Studies

Twenty different nanoparticles along with their non-targeted counterparts, all at one dose: 50 mmole $^{19}$F/kg, can be screened for high tumor-to-organ ratios and rapid excretion ($t_{1/2}$ in the range from hours to days). PK of each nanoparticle each nanoparticle sample can be evaluated at three doses (the default choices are 10, 50 and 100 mmole $^{19}$F/kg). Hence, again roughly 20 samples (6-7 different nanoparticles, each at three different doses) and their non-targeted counterparts can be evaluated. The cell line and the animal model can be as discussed previously. Tumor implantation and nanoparticle doses can be as discussed previously. For each nanoparticle sample and for each dose, data can be collected in 6 rats (3 male/3 female). Animals can be anesthetized with ketamine/xylazine and injection of the microemulsion will occur via tail vein. Anesthesia can be maintained with injection of a combination of ketamine/xylazine. At 0, 0.25, 0.5, 1, 2, and 4 hours after administration, a 0.5 mL blood sample can be drawn from the tail vein for assessing the plasma washout profile of the fluorocarbon nanoparticles. To limit the amount of blood withdrawn from each animal, samples can be staggered so that each animal has samples taken at four of the time points. This can allow collection of four samples per desired time point. Following this sample, animals can be allowed to recover and returned to the vivarium where they can be housed in metabolic cages. At 1, 3, 7, 14 and 28 days after injection, 6 rats can be sacrificed and their organs harvested for biodistribution analysis. Tumor, liver, spleen, kidney, lung, brain, and heart can be separately homogenized and assayed for nanoparticle concentration. Blood concentrations can also be measured at these time points. The function of the metabolic cages is to collect urine and feces so that the amount of F-oils and F-surfactants, particularly the less volatile F-surfactants, excreted though the trine and feces can be estimated.

The concentration measurements from the plasma samples during the first four hours can be fit to a compartmental pharmacokinetic model using a naïve pooled method. This will allows investigation of how rapidly the microemulsion is taken up into tissues. The tissue samples can be analyzed using non-compartmental pharmacokinetic modeling methods. Both approaches use commercially available pharmacokinetic software (WinNonLin, Pharsight, Mountain View Calif.). The naïve pooled compartmental pharmacokinetic model gives a general description of the rate at which the emulsion leaves the plasma and is taken up in the tissues. A naïve pooled approach can be used because it allows all the samples to be used in fitting one descriptive pharmacokinetic model with the limited number of samples per animal [Ette, E. I. & Williams, P. J. Population pharmacokinetics II: estimation methods. Ann. Pharmacotherapy, 38, 1907-15, 2004]. Estimates of systemic and local $C_{max}$, $T_{max}$, AUC, Mean Residence Time, Clearance, and Distribution can be made using WinNonLin. Accumulated drug in the organs can be assessed to identify relative efficacy in tissue targeting. Tissue targeting efficacy can be assessed by comparing the AUC for the each organ of interest compared to the AUC in the tumor. This gives an indication of the relative amount of drug exposure each tissue receives [Norwich, K. H. Noncompartmental models of whole-body clearance of tracers: a review. Ann Biomed. Eng. 25, 421-39, 1997; Gillespie, W. R. Noncompartmental versus compartmental modelling in clinical pharmacokinetics. Clin Pharmacokinetics, 20, 253-62, 1991]. Mean residence time, which determines the average time that drug molecules are present in the tissue, also provides a relative comparison of targeting efficacy. The remaining parameters (maximum concentration—$C_{max}$, and time of maximum concentration—$T_{max}$) can be used for assessing whether the exposure of different organ systems are bioequivalent. This is another metric for comparing the efficacy of the targeting capabilities of the microsomal constructs [Alvan, G., Paintaud, G. & Wakelkamp, M. The efficiency concept in pharmacodynamics. Clin Pharmaco-kinetics, 36, 375-89, 1999].

Without wishing to be bound by theory, it is believed that the accumulation of the nanoparticles in the tumor can be significantly enhanced comparing to the same nanoparticles that lacks the targeting capability (carrying the non-targeting octreotide analog). Since liver and spleen are major organs taking up fluorocarbons in a non-specific fashion [Ratner, A. V., Hurd, R., Muller, H. H., Bradley-Simpson, B., Pitts, W., Shibata, D., Sotak, C. & Young, S. W. $^{19}$F magnetic resonance imaging of the reticuloendothelial system. Magn. Reson. Med. 5, 548-554, 1987], tumor retention of fluorocarbon nanoparticles with liver and spleen can be evaluated. The PK profile in the liver & spleen also provides an assessment of potential radiation damage to normal tissues in the therapy, when a radioactive moiety, $^{90}$Y, is attached to the fluorocarbon nanoparticles.

o. Experimental Protocol

Accumulation of the nanoparticles in the tumor versus liver and spleen over a time course of 4 weeks can be compared over a group of rats bearing subcutaneous pancreatic tumors. Three doses can be tested for each type of nanoparticles: 10, 50 and 100 mmole $^{19}$F/kg. Long term (12 w) retention of the nanoparticles in the liver and spleen can be determined on a group of normal rats; for each type of nanoparticles, a dose of 50 mmole $^{19}$F/kg can be examined.

$^{19}$F imaging can be performed on 4.7 T horizontal bore magnet using a $^{1}$H/$^{19}$F dual tune volume coil. A spin echo pulse sequence can be used for acquisition of the $^{19}$F images. The nanoparticles give rise to two sharp yet closely spaced resonances in the $^{19}$F NMR spectrum; the peaks are 0.25 ppm apart and represent the F-oil and F-surfactant component of the nanoparticle respectively (FIG. 4). Both peaks can be used for imaging. Transaxial (perpendicular to the long axis of the rat) $^{19}$F images covering the liver and spleen and tumor can be acquired and overlaid with the H-1 MR images of the same orientation and slice thickness. A phantom containing a known concentration of the same nanoparticles can be placed beside the animal during imaging. $^{19}$F signals from liver & spleen and tumor can be integrated on each slice and summed up for the whole organ; signal from the whole phantom will also be obtained; a ratio of liver$_{F19}$/phantom$_{F19}$ and tumor$_{F19}$/phantom$_{F19}$ can be obtained. The ratio (i.e., normalized to phantom signal) is used as an index for nanoparticle accumulation in the liver & spleen and tumor respectively, and can be plotted over time. The accumulation in the tumor can be compared with that in the liver & spleen. The time course of nanoparticle accumulation in the liver & spleen of normal rats (no tumor) can be subjected to pharmacokinetic modeling [Wahl, R. L. Tositumomab and 131I therapy in non-Hodgkin's lymphoma. J. Nucl. Med. 46 (Suppl. 1), 128S-140S, 2005], which provides a profile of nanoparticle retention and excretion.

p. Data Analysis

A group (n=7 for each nanoparticle dose and for a control nanoparticle that carries a non-targeting peptide) of tumor bearing rats receives an intravenous injection of 50 mmole $^{19}$F/kg of the nanoparticle in saline when the tumor reaches about 10 mm×10 mm (measured from the two orthogonal axis of the tumor). They can be subjected to MR studies, for example, at day 1, 3, 7, 14, 21 and 28 days after injection of the nanoparticles. The tumor accumulation for various nanoparticles can be compared and can be compared to accumulation of nanoparticles without a targeting peptide; accumulation in the liver & spleen and tumor over time will also be compared; paired t-test can be used for statistical analysis; P value ≦0.05 can be considered as statistically significant.

A group (e.g., n=7) of normal rats will receive i.v. injection of 50 mmole $^{19}$F/kg nanoparticles and can be subjected to MR studies at 1, 3, 7 days and followed by weekly scan up to 12 weeks after administration. Time course of liver & spleen retention of the nanoparticles can be fitted to both single exponential and linear elimination models as described previously [Meyer, K. L., Carvlin, M. J., Mukherji, B., Sloviter, H. A. & Joseph, P. M. Fluorinated blood substitute retention in the rat measured by fluorine-19 magnetic resonance imaging. Invest. Radiol. 27, 620-627, 1992] and half life ($t_{1/2}$) for the exponential phase and linear phase of elimination can be obtained.

Owing to the targeting peptide on the nanoparticles and without wishing to be bound by theory, it is believed that that tumor retention of the nanoparticles can be significantly increased compared to nanoparticles that carry a non-targeting peptide (control particles). However, significant uptake in the liver & spleen is anticipated and can be monitored by $^{19}$F MR; however, without wishing to be bound by theory, it is believed that that the nanoparticles can be cleared out from the liver & spleen sooner than the tumor. The amount of accumulation and time of retention of the nanoparticles in the liver & spleen allows estimation of the radiation damage introduced when the nanoparticle carries $^{90}$Y$^{3+}$, a radioactive isotope. A more accurate estimate of $^{90}$Y distribution is to let the nanoparticle carry $^{89}$Y$^{3+}$ in addition to Gd$^{3+}$. In addition, the potential toxicity of the fluorocarbon nanoparticles to the liver & spleen can be examined by serum AGT level weekly and by histological examination of the liver & spleen at 8$^{th}$ week after administration of the nanoparticles (mice can be euthanized).

The Gd$^{3+}$ moiety associated with the fluorocarbon nanoparticle provides a tumor specific enhancement of $^1$H signal on MR images. This property can be extremely useful when tumor is located deep inside the body (e.g., a pancreatic tumor) or when its size is small. The enhancement of tumor signal can be compared before and 4, 24, 48 hours after administration of the Gd$^{3+}$ containing nanoparticles that contains either a targeting peptide or a non-targeting peptide. Without wishing to be bound by theory, it is believed that the signal enhancement in tumor can be increased ≧30% when the nanoparticle carries a targeting peptide compared to a non-targeting one.

Rats bearing subcutaneous tumors can be subjected to MR studies when the tumor reaches 10 mm×10 mm (measured from the two orthogonal axis of the tumor). A baseline scan ($^1$H and $^{19}$F imaging) can be performed before the rat is injected i.v. with 10, 50 or 100 mmole $^{19}$F/kg nanoparticles; for each dose, the particles that carry a non-targeting peptide can be used as control; $T_1$-weighted and $T_2$-weighted $^1$H images can be acquired along with $^{19}$F MR images at 4, 24, and 48 hours after administration of the nanoparticles.

$^{19}$F images can be overlaid with T1W and T2W H-1 images; T1W images indicates the effect of paramagnetic reagent (in this case Gd$^{3+}$) in which locations accumulating the Gd$^{3+}$ can have higher signal intensities; on the other hand, T2W images provides information about components of the tumor (necrotic, viable and edematous regions); by overlaying $^{19}$F signal on $^1$H images, important information regarding the location and extent of nanoparticle accumulation is gained. Signal intensities from tumor at pre- and post-contrast enhancement time points can be normalized to the intensity of phantom signal in the same field-of-view before comparing with each other. This is to ensure that any slight differences in receiver gain, magnetic homogeneity, etc., do not affect the quantification.

Without wishing to be bound by theory, it is believed that, with the targeting moiety, the enhancement of tumor $^1$H signal due to the presence of Gd$^{3+}$ can be ≧30% compared to non-targeted nanoparticles; due to long circulation time of these particles, the accumulation will increase over time so will the enhancement. By varying the payload of Gd$^{3+}$ moieties, the enhancement is likely to be optimized to detect small size tumor.

$^{19}$F MR relaxometry can be implemented for measurements of tumor pO$_2$ to evaluate O$_2$ delivery capacity of the fluorocarbon nanoparticles. Tumor pO$_2$ can be an important parameter that determines the success of radiotherapy because hypoxic tumor is resistant to radiation [Gray, L. H., Conger, A. D., Ebert, M., Hornsey, S. & Scott, O. C. The concentration of oxygen dissolved in tissues at the time of irradiation as a factor in radiotherapy. Br. J. Radiol. 26, 638-648, 1953; Hall; E. J., Radiobiology for the radiologist (4th edition). Lippincott, Philadelphia, 1994]. For a hypoxic tumor (pO2<10 mmHg), radiation dose three times higher than that for an oxygenated tumor (pO2>30 mmhg) is needed [Hall, E. J., Radiobiology for the radiologist (4th edition). Lippincott, Philadelphia, 1994]. Although polarographic needle oxygen electrodes (Eppendorf Histograph) are widely used in the clinic, it is an invasive (destructive) technique and can only access to relatively superficial tumors [Nelson, et al., A noninvasive approach for assessing tumor hypoxia in xenografts: developing a urinary marker for hypoxia. Cancer Res. 65, 6151-6158, 2005]. A unique capability of $^{19}$F MR is to allow non-invasive estimation of tissue pO$_2$ by measuring its spin-lattice relaxation time ($T_1$). By varying O$_2$ concentration in the phantom solution of fluorocarbon nanoparticles, a calibration curve ($T_1$ vs pO$_2$) can be constructed at a specific temperature using the same MR coil configuration and pulse sequence as for in vivo studies. Tumor pO$_2$ will then be obtained from the calibration curve once its $T_1$ is determined by $^{19}$F MR. Non-invasive MR technique can be validated against the oxygen sensitive electrode polarographic measurements. The fluorocarbon nanoparticles can then be evaluated for their sensitivity and accuracy for probing tumor pO$_2$.

Without wishing to be bound by theory, it is believed that tumor periphery can have significantly higher pO$_2$ than the tumor center; however, pO$_2$ of a tumor center can be increased when an animal is allowed to breathe carbogen (95% O$_2$ and 5% CO$_2$). Also without wishing to be bound by theory, it is believed that uptake of nanoparticles in the tumor can increase the tumor pO$_2$ when the animal breathes carbogen beyond the level that is achieved by carbogen breathing alone.

As shown in Stage 2 of FIG. 2, carbogen breathing combined with fluorocarbon nanoparticle delivery provides a potential to increase the tumor pO$_2$ leading to sensitization of tumor to radiotherapy. The mechanism of carbogen breathing to increase the tumor oxygenation has been studied extensively [Howe, F. A., Robinson, S. P., Rodrigues, L. M. & Griffiths, J. R. Flow and oxygenation dependent (FLOOD) contrast MR imaging to monitor the response of rat tumors to carbogen breathing. Magn. Reson. Imag. 17, 1307-1318, 1999] and carbogen breathing has been combined with perfluorocarbon compounds for delivery of oxygen to the hypoxic tissues [Teicher, B. A. & Rose, C. M. Oxygen-carrying perfluorochemical emulsion as an adjuvant to radiation therapy in mice. Cancer Res. 44, 4285-4288, 1984; Al-Hallaq, et al., MRI measurements correctly predict the relative effects of tumor oxygenation agents on hypoxic fraction in rodent BA1112 tumors. Int. J. Radiat. Oncology Biol. Phys. 47, 481-488, 2000; Koch, et al., Radiosensitization of hypoxic tumor cells by dodecafluoropentane: A gas-phase perfluorocarbon emulsion. Cancer Res. 62, 3626-3629, 2002].

q. Measurement of Tumor pO$_2$ by $^{19}$F-Relaxometry.

Rat pancreatic cancer (AR4-2J from American Type Tissue Culture, ATTC) over-expressing somatostatin receptor type 2 (sstr2) can be grown subcutaneously in the hind limbs of rats. The animal can be subjected to pO$_2$ measurements when tumor reaches to 10 mm×10 mm (measured from two orthogonal axes of the tumor).

Calibration curves ($T_1$ versus pO$_2$) can be constructed on a phantom containing fluorocarbon nanoparticles in saline following established procedures [Parhaml, P. & Fung, B. M. Fluorine-19 relaxation study of perfluoro chemicals as oxygen carriers. J. Phys. Chem. 87, 1928-1931, 1983; van der Sanden, et al., Characterization and validation of non-invasive oxygen tension measurements in human glioma xenografts by 19F-MR relaxometry. Int. J. Radiat. Oncology Biol. Phys. 44, 649-658, 1999; Mason, R. P., Shukla, H. & Antich, P. P. In vivo oxygen tension and temperature: simultaneous determination using 19F NMR spectroscopy of perfluorocarbon. Magn. Reson. Med. 29, 296-302, 1993]. During construction of calibration curve, the pO2 in the solution is known and controlled while the corresponding $T_1$ value is measured by $^{19}F$ MR. Note, same MR coil setting and pulse sequence can be used for phantom as well as for in vivo studies; temperature of the phantom solution is monitored by a thermister and is maintained to a specified value and a number of calibration curves corresponding to different temperatures can be constructed.

Once the calibration curve is constructed, animals can be injected intravenously (i.v.) the fluorocarbon nanoparticles; three doses, for example, can be tested, 10, 50 and 100 mmole $^{19}F/kg$ of body weight; rats can be subjected to $T_1$ measurement. The $^{19}F$ $T_1$ map can be generated using an imaging based multi-slice sequence developed previously [Zhou, et al., Simultaneous measurement of arterial input function and tumor pharmacokinetics in mice by dynamic contrast enhanced imaging: effects of transcytolemmal water exchange. Magn. Reson. Med. 52, 248-257, 2004]; on a $T_1$ map, each pixel intensity value represents its $T_1$ value and can be converted to $pO_2$ value using the calibration curve. High resolution $T_2$ weighted (T2W) H-1 spin echo images can be acquired; necrotic region (if any) can be identified on the $T_2$ weighted images; tumor can be segmented into peripheral and central region on the $T_2$ weighted images which are overlaid on corresponding $^{19}F$ images; regional $pO_2$ can be obtained by averaging the $pO_2$ of pixels in the specified region.

Immediately after $^{19}F$ relaxometry, rats can be subjected to computerized polarographic needle electrode system (KI-MOC 6650, Eppendorf) for measurements of tumor $pO_2$. The polarographic needle has a diameter of 300 µm with a sensitive membrane covered cathode of 17 µm, resulting in a hemispherical sensitive volume of 50 µm in diameter. In order to be able to compare $pO_2$ results from $^{19}F$ relaxometry, polarographic measurements can be performed along two perpendicular tracks in the corresponding tumor slices as used in the $^{19}F$ relaxometry.

r. Nanoparticles as $O_2$ Delivery Vehicles

Without wishing to be bound by theory, it is believed that carbogen breathing will enhance tumor $pO_2$ and the uptake of fluorocarbon nanoparticles in the tumor will further enhance tumor $pO_2$ beyond that achieved by carbogen breathing alone. Rat pancreatic cancer (AR4-2J) overexpressing somatostatin receptor type II (SSTRII) can be grown subcutaneously in the hind limbs of rats. When the tumor reaches to 10 mm×10 mm (measured from two orthogonal axes of the tumor), tumor $pO_2$ can be measured by Eppendorf needle electrodes with animal breathing air and then carbogen; then the animal can be injected intravenously with fluorocarbon nanoparticles (10, 50 or 100 mmole $^{19}F/kg$); twenty-four hours after nanoparticle administration, tumor $pO_2$ can be measured by Eppendorf needle electrodes with animal breathing air and then carbogen. Note when the breathing gas is shifted from air to carbogen; a stabilizing period of 5 min can be used before a $pO_2$ measurement starts and the rat remains inhaling carbogen during the measurement.

Three doses, with each dose having seven to ten (n=7-10) rats bearing subcutaneous pancreatic cancer can be utilized. Tumor can be segmented using T2W images into peripheral (4 mm rim from the boundary of the tumor) and the region inside the rim can be counted as the central region. Regional $pO_2$ assessed by MR and by polarographic measurements can be tabulated and compared using paired t-test. P value $\leq 0.05$ can be considered as statistically significant.

The relationship between $T_1$ and $pO_2$ can be formulated in the equation below [Zhao, D., Jiang, L. & Mason, R. P. Measuring changes in tumor oxygenation. Methods in Enzymology, 386, 378-418, 2004]:

$$R_1(\equiv 1/T_1)=a+bpO_2 \qquad (3)$$

The ratio $\eta=b/a$ has been proposed as a sensitivity index, therefore, $\eta$ values can be compared among various fluorocarbon nanoparticles to evaluate their sensitivity as a $pO_2$ probe. Seven to ten (n=7-10 for each dose) rats bearing subcutaneous pancreatic tumors can be used. Regional (periphery and center) tumor $pO_2$ before and during carbogen breathing can be compared using paired t-test. P value $\leq 0.05$ can be considered as statistically significant.

The $^{19}F$ $T_1$ of fluorocarbon compound varies linearly with $pO_2$, and each resonance is sensitive to pO2, temperature, and magnetic field, but importantly, is essentially unresponsive to pH, $CO_2$, charged paramagnetic ions, mixing with blood, or emulsification [Zhao, D., Jiang, L. & Mason, R. P. Measuring changes in tumor oxygenation. Methods in Enzymology, 386, 378-418, 2004]. Due to the temperature dependent of $T_1$ of the nanoparticles, maintaining the temperature of the tumor the same as the temperature under which the calibration curve is established is critical for accurate estimation of tumor $pO_2$. Two temperature sensors can be used, one in the rectum (core temperature) and the other on the surface of the subcutaneous tumor. Warm air can be directed to the bore of the magnet to maintain the core temperature at 37±0.2° C.; once the core temperature is stabilized, the temperature on the tumor surface can be used for the construction of the calibration curve.

It has been observed frequently by other investigators discrepancies between $^{19}F$ relaxometry and polarographic electrode based measurement of tumor $pO_2$: $^{19}F$ relaxometry generally yields higher $pO_2$ values than Eppendorf electrodes (Robinson, S. P. & Griffiths, J. R. Current issues in the utility of 19F nuclear magnetic resonance methodologies for the assessment of tumor hypoxia. Phil. Trans. R. Soc. Lond. B 359, 987-996, 2004]. It has been suggested that this is primarily due to the $^{19}F$ relaxometry measurements are more weighted towards tumor periphery, where the blood vessels are more abundant and perfluorocarbon compounds are carried in by perfusion; however, the needle electrodes do not have such bias. Without wishing to be bound by theory, it is believed that segmenting tumor into rim and central region and comparing the regional measurement of $pO_2$ by the two methods decreases the discrepancies. If the central region of the tumor is significantly necrotic, and thus has very limited perfusion leading to very low accumulation of nanoparticles, only the tumor rim regions are compared. Without wishing to be bound by theory, it is believed that both methods are sufficiently sensitive to detect the difference in $pO_2$ pre- and post carbogen breathing.

The amount of fluorocarbon nanoparticles accumulated in the tumor determines whether the signal-to-noise ratio (S/N) of $^{19}F$ signal is sufficient for imaging, which yields a pixel-by-pixel map of $pO_2$ of the tumor. In case of insufficient S/N, unlocalized $^{19}F$ spectroscopy is used, in which signal from whole tumor can be collected (using a solenoid coil) resulting in estimation of global $pO_2$ of the tumor. In such a case, the tumor periphery is not separated from tumor center; however, the spectroscopic method can be faster in measurements of global tumor $pO_2$ and is typically sensitive enough to detect difference in $pO_2$ before and after carbogen breathing.

Based on results of in vivo imaging studies, the fluorous nanoparticles can be modified and optimized. One goal of nanoparticle improvement can be in pharmacokinetics, i.e., higher tumor-to-organ ratio and optimal excretion profile (t½ in the range of hours to days, not minutes or weeks and months). The secondary goal can be in increasing imaging sensitivity of for drug tracing, tumor visualization and $pO_2$ oximetry. Modification of the nanoparticles can be conducted at both the molecular level and the formulation level, using the methods previously described herein. For example, the nanoparticles can be made more hydrophilic either at the molecular level incorporating more oxyethylene units to F-surfactants or at the formulation level by increasing the percentage of charged surfactants.

L. MICROBICIDAL FLUOROCARBON NANOEMULSIONS

Emulsions are ternary liquid systems made of oil, surfactant (emulsifier) and water. See, generally, [Hamouda, T., Myc, A., Donovan, B., Shih, A. Y., Reuter, J. D., Baker, J. R. A novel surfactant nanoemulsion with a unique non-irritant topical antimicrobial activity against bacteria, enveloped viruses and fungi. Microbiol. Res. 156, 1-7, 2001; Myc, A., Vanhecke, T., Landers, J. J., Hamouda, T. & Baker, J. R. The fungicidal activity of novel nanoemulsion (X8W60PC) against clinically important yeast and filamentous fungi. Mycopathologia, 155, 195-201, 2001; Chepurnov, A. A., Bakulina, L. F., Dadaeva, A. A., Ustinova, E. N., Chepurnova, T. S. & Baker, S. R. Inactivation of Ebola virus with a surfactant nanoemulsion. Acta Tropica, 87, 315-320, 2003]. In nanoemulsions, the size of oil droplets is on the order of several to tens of nanometers, hence the name nanoemulsion. It has been found that nanoemulsions have biocidal activities against a wide spectrum of microbial organisms, including viruses (e.g., Ebola virus, herpes simplex type 1, influenza A, vaccinia virus, etc.), bacteria (e.g., *Bacillus cereus, Bacillus subtilis, Haemophilus influenza, Niesseria gonorrhoeae, Streptococcus pneumoniae*, etc.) and fungi (e.g., *Candida albicans, Microsporuin gypseum, Fusarium oxysporum*, etc.). Without wishing to be bound by theory, the proposed mechanism of microbicial activity is that the high surface energy of the nanoparticles causes them to fuse with the outer membrane of the microbes, eventually causing the outer membrane to burst, hence killing the microbes.

Engineered fluorocarbon nanoemulsions can have microbicidal activities. The nanoparticles in such an emulsion are made of highly fluorinated oils and surfactants (F-oils and F-surfactants). The rationale is that F-surfactants have high surface activities. Hence, nanoemulsions formulated from F-oils and F-surfactants are more potent than hydrocarbon nanoemulsions in terms of microbicidal activities. Indeed, F-surfactants have been found in the past to have strong antibacterial and anti-HIV activities [Sawada, H., Ohashi, A., Baba, M., Kawase, T. & Hayakawa, Y. Synthesis and surfactant properties of fluoroalkylated sulfonic acid oligomers as a new class of human immunodeficiency virus inhibitors. J. Fluorine Chem. 79, 149-155, 1996; Sawada, et al., Synthesis of novel fluoroalkylated 4-vinylpyridinium chloride oligomers as functional materials possessing surfactant and biological properties. J. Fluorine Chem. 83, 125-131, 1997; Sun, J. Y., Li, J., Qiu, X.-L. & Qing, F.-L. Synthesis and structure-activity relationship (SAR) of novel perfluoroalkyl-containing quaternary ammonium salts. J. Fluorine Chem. 126, 1425-1431, 2005].

There are at least three specific uses for such nanoemulsions; each application takes advantage of unique properties of fluorocarbons. The first application is for first-line prevention and treatment of influenza and other respiratory viruses in the case of an outbreak. For this type application, the nanoemulsions can be formulated into aerosols (nasal sprays and inhalers). Note that fluorocarbons have traditionally been used in the formulation of aerosols [Lowe, K. C. Perfluorochemical respiratory gas carriers: benefits to cell culture systems. J. Fluorine Chem. 118, 19-26, 2002] and hence the present fluorocarbon-based nanoemulsions can have a distinct advantage in this regard. The second application is for first-line prevention and treatment in the case of bioterrorism attacks. In this case, the nanoemulsion can be formulated into either aerosols or sprays. Again, the weak intermolecular interactions among fluorocarbon compounds make them well-suited for such formulations. The third application is for preventing sexually transmitted diseases (STD). For this type of application, the nanoemulsions can be formulated as a gel. The weak intermolecular interactions of fluorocarbons make them suitable for lubricant-based anti-STD products (fluorocarbon materials can easily spread and are very slippery [Lemal, D. M. Perspective on fluorocarbon chemistry. J. Org. Chem. 69, 1-11, 2004]). Further, due to the chemical inertness of fluorocarbons, minimum storage restrictions are needed for such gels, making them suited for anti-STD applications in developing countries. An additional advantage is that the $^{19}F$ signal makes possible the measurement of the in vivo distribution of such gels in the vagina using $^{19}F$ MRI. Currently, this is investigated by incorporating $Gd^{3+}$-based contrast agents into the gel (E. S. Pretorius, K. Timbers, D. Malamud & K. Barnhart, Magnetic resonance imaging to determine the distribution of a vaginal gel: before and after both simulated and real intercourse. Contraception, 66, 443-451, 2002; K. T. Barnhart, E. S. Pretorius, K. Timbers, D. Shera, M. Shabbout & D. Malamud, In vivo distribution of a vaginal gel: MRI evaluation of the effects of gel volume, time and simulated intercourse. Contraception, 70, 498-505, 2004). However, whether the image reflects the distribution of the gel or the contrast agents can be questionable (K. Barnhart, E. S. Pretorius, A. Stolpen & D. Malarmud, Distribution of topical medication in the human vaginal as imaged by magnetic resonance imaging. Fertility and Sterility, 76, 189-195, 2001). One benefit of a fluorocarbon gel is that no extraneous MRI contrast agent is needed because the $^{19}F$ signal of the gel itself can be used for MRI detection. In such a case, the image always belongs to the gel itself.

The present compounds, specifically the disclosed F-oils and F-surfactants, can be used in connection with the nanoemulsions. That is, F-oils and F-surfactants can be formulated into nanoemulsions. Size of fluorocarbon particles the nanoemulsions can be determined by small-angle X-ray scattering (SAXS). Microbicidal activities of the formulated nanoemulsions are assayed in cell culture first. To enhance surface activity, the fluorocarbon moiety of each molecule is as expanded as possible. Also, the shape of F-surfactants matches that of F-oils so that any temporary "cavity" vacated by an F-oil can be filled in snugly by an F-surfactant and vice versa. This significantly increases the stability of the nanoemulsion. Structures of example suitable F-oils and F-surfactants are given in the scheme below.

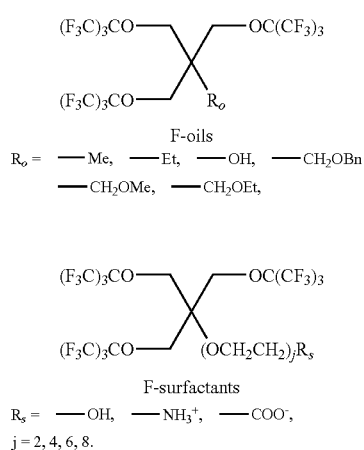

Figure 6:
FIG. 6 shows the gradual gelation of a fluorocarbon nanoemulsion as the amount of added F-surfactant increases (the amount of F-surfactant increases from left to right). The F-oil used in here was an analog of compound 4 with —OBn replaced by -Me; the F-surfactant used was compound 10.

F-oils $R_o$ = —Me, —Et, —OH, —$CH_2OBn$
—$CH_2OMe$, —$CH_2OEt$,

F-surfactants $R_s$ = —OH, —$NH_3^+$, —$COO^-$,
j = 2, 4, 6, 8.

The nanoemulsions can be formed simply by mixing the F-oil and F-surfactant with physiological buffer system and shaking vigorously. FIG. 6 shows pictures of one such formulation process (the amount of F-surfactant increases from left to right). As can be seen, the emulsion eventually gels (right-most picture) as more surfactants are added. The average particle size is 6.6 nm. Nanoemulsions of various surface charges and sizes can be formulated in a modular fashion by incorporating different F-oils and F-surfactants. Stability of the nanoemulsions can be followed by SAXS as a function of time and storage temperature (i.e., to monitor particle size as a function of time). Virucidal assays are conducted against a series of viruses; including respiratory viruses (Flu A & B, measles, Rhino and SARS), STD viruses (HSV-1, -2, HHV-8 and HIV) and biodefense-related viruses (VEE, punta toro, West Nile). Without wishing to be bound by theory, it is believed that the nanoemulsions also have bactericidal activities.

M. FLUOROUS MIXTURE SYNTHESIS OF FLUORINATED DENDRON AMPHILES WITH ONE SINGLET $^{19}F$ NMR SIGNAL

Fluorinated microemulsions have a long history in biomedicine as, for example, blood substitutes, ultrasound contrast agents, $^{19}F$ nuclear magnetic resonance (MR) imaging reagents, and tumor relaxometry and radiosensitization probes. Fluorocarbon liquid nanoparticles, formulated as microemulsions, can also be employed as multifunctional drug delivery vehicles for $^{19}F$ magnetic resonance image (MRI) guided targeted cancer therapy. [See, e.g., Yu, Y. B. *J. Drug Targeting* 2006, 14, 663-669; Lanza, G. M.; Wickline, S. A. *Prog. Cardiovasc. Dis.* 2001, 44, 13-31; Morawski, A. M.; Winter, P. M.; Yu, X.; Fuhrhop, R. W.; Scott, M. J.; Hockett, F., Robertson, J. D.; Gaffaey, P. J.; Lanza, G. M.; Wickline, S. A. *Magn. Reson. Med.* 2004, 52, 1255-1262; Krafft, M. P. *Adv. Drug. Del. Rev.* 2001, 47, 209-228; Riess, J. G. *Tetrahedron,* 2002, 58, 4113-4131; Kuznetsova, I. N. *Pharmaceutical Chem. J.* 2003, 37, 415-420.] However, because fluorinated amphiles A are highly hydrophobic and only slightly soluble in water, fluorinated amphiles A typically do not form fluorinated oil-in-water microemulsions. A class of fluorinated amphiles (G3 for an example) was then prepared.

G0

G1

G2
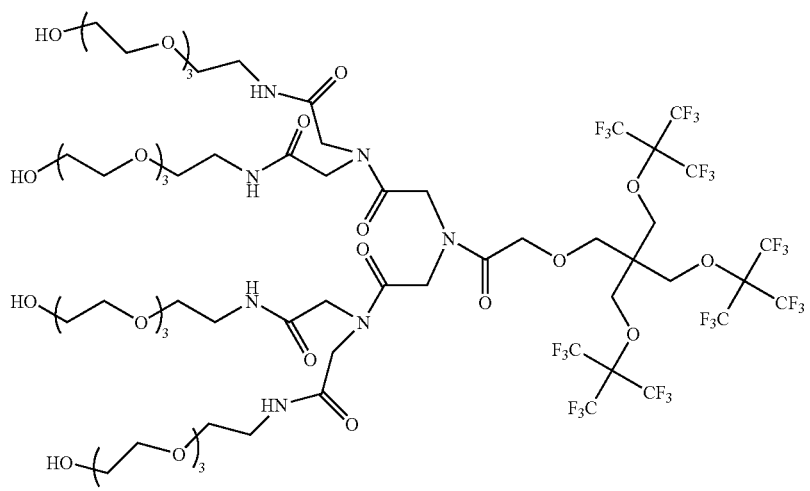
G3
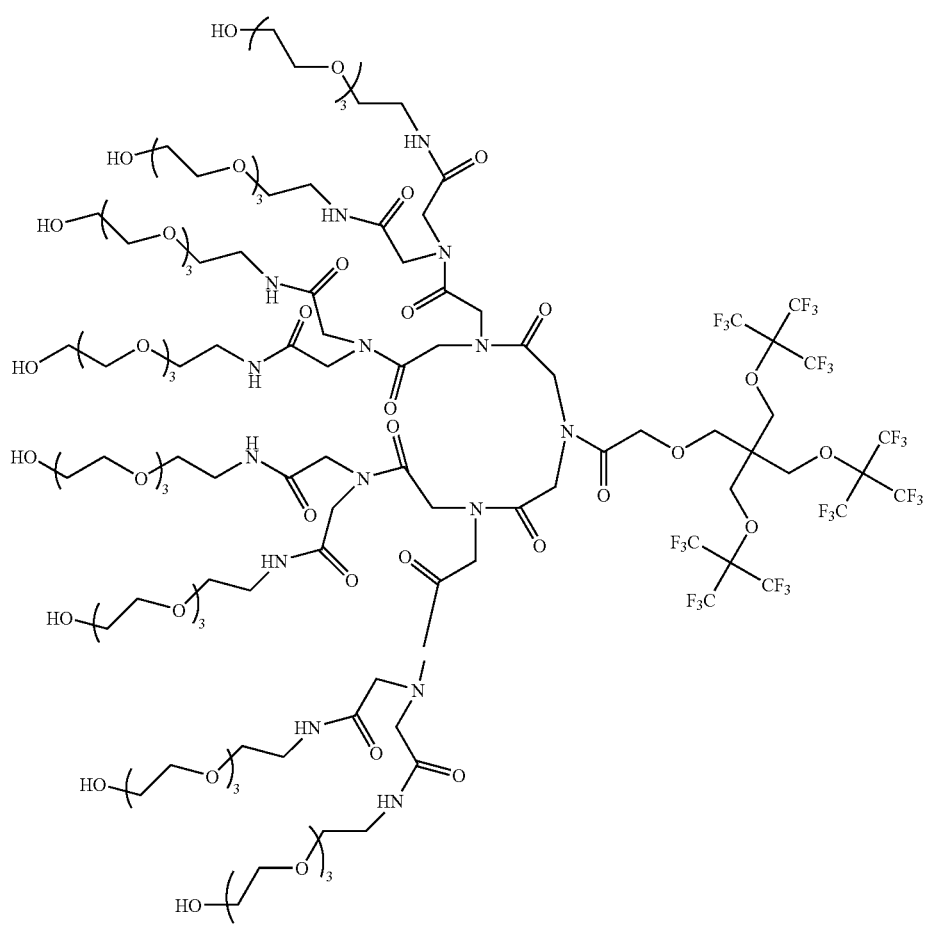

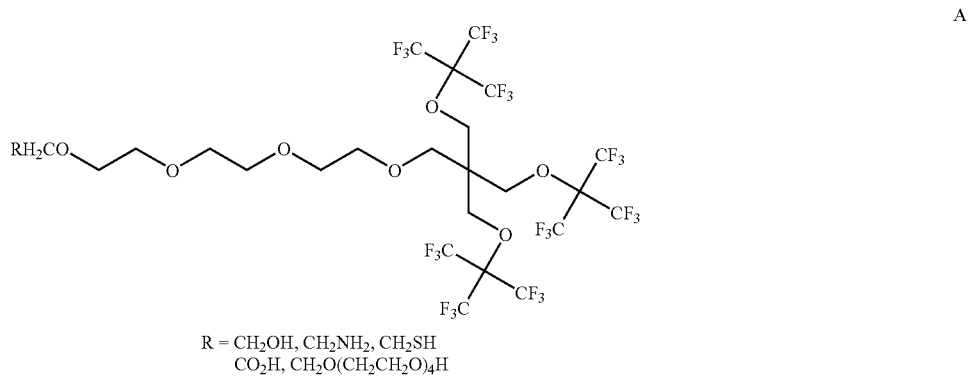

A

R = CH$_2$OH, CH$_2$NH$_2$, CH$_2$SH
CO$_2$H, CH$_2$O(CH$_2$CH$_2$O)$_4$H

In order to achieve high $^{19}$F signal intensity (twenty-seven chemically identical fluorine atoms), the perfluoro-tert-butyl ether moiety was selected. To increase the water solubility and biocompatibility, an amide-based dendron structure with tetra(ethylene glycol) ending groups was conjugated to the fluorinated part with an amide bond. For a systematic screen and properties study, a few continual generations of fluorinated dendron amphiles were preferred.

Fluorous mixture synthesis (FMS)—in which members of a series of substrates are tagged with different fluorous tags, mixed, carried through a series of reactions, and then separated based on the tag prior to detagging—provides a fast and convenient strategy for the synthesis of enantiomers, diastereomers and compound libraries. However, FMS has not before been used in connection with dendrimer synthesis. Here, EMS is employed in connection with the synthesis of the above mentioned fluorinated dendron amphiles. In this case, no detagging step is typically required, as the final products comprise fluorine. The demixing of different generations of fluorinated dendron amphiles can be based on the size of nonfluorinated portion instead of different fluorinated tags. As final products can be separated (or purified) by HPLC with a fluorinated column, each generation of fluorinated dendrons can be isolated in substantially pure form.

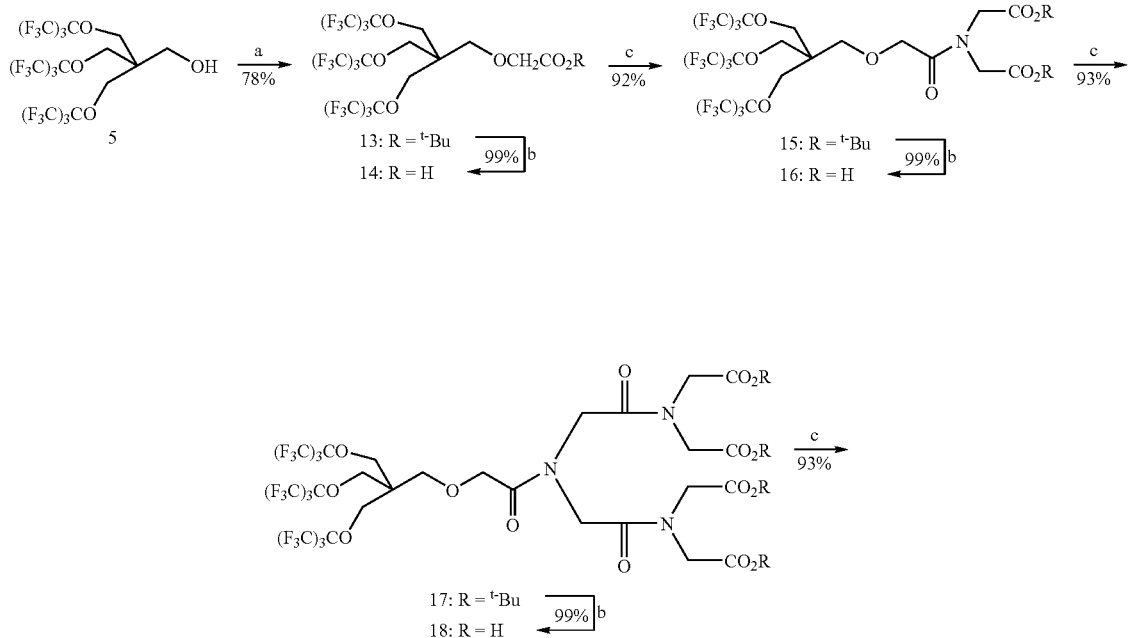

Scheme 1[i]

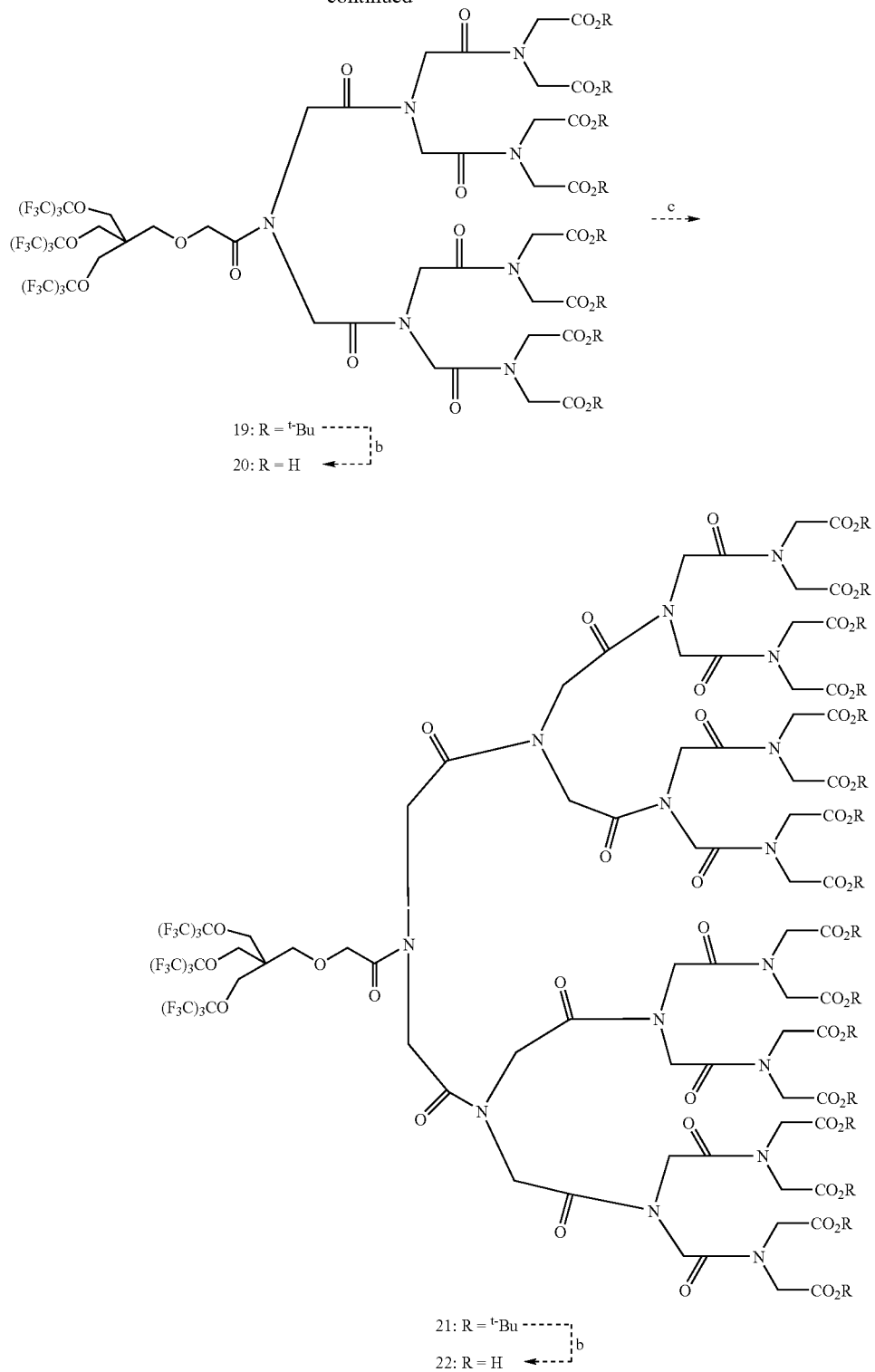

19: R = $^t$Bu
20: R = H

21: R = $^t$Bu
22: R = H $^i$Conditions: (a) KH (35%), BrCH$_2$CO$_2$$^t$Bu, THF, rt.; (b) TFA, anisol, CH$_2$Cl$_2$, rt.; (c) DIC, HOBt, HN(CH$_2$CO$_2$$^t$Bu)$_2$, DMF/THF (1/1), rt.

All the intermediates for five generations of fluorinated dendrons were then synthesized on a 300-mg scale in six steps from the common starting material perfluoro-tert-butyl ether 5 in high yield without any column purification. Treatment of alcohol 5 with potassium hydride and tert-butyl bromoacetate gave ester 13 with 78% yield after simple phase separation of the quenched reaction mixture. Ester 13 was reacted with trifluoroacetic acid to give the acid 14 in quantitative yield after removal of reaction solvent, anisol, and TFA. Acid 14 was then coupled with di-tert-butyl iminodiacetate to yield ester 15 after fluorous solid phase extraction. By repeating the coupling and deprotecting processes, intermediates for the other three generations of dendrons were obtained on 400-mg scales in excellent yields.

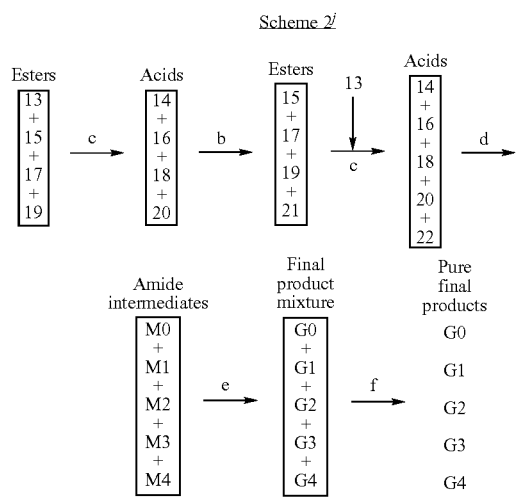

Scheme 2$^j$ $^j$Conditions: (b) TFA, anisol, CH$_2$Cl$_2$, rt.; (c) DIC, HOBt, HN(CH$_2$CO$_2^t$-Bu)$_2$, DMF/THF(1/1), rt.; (d) DIC, HOBt, H$_2$N(CH$_2$CH$_2$O)$_4$Bn, DMF/THF(1/1), rt.; (e). H$_2$, Pd/C, MeOH, rt.; (f). HPLC purification on FlouroFlash column.

Fluorous mixture synthesis was then carried out by mixing the four esters (13, 15, 17 and 19). The mixture of esters was then cleaved with TFA to give a mixture of acids, which was then coupled with di-tert-butyl iminodiacetate to yield a mixture of higher generation esters after fluorous solid phase extraction. After addition of another potion of ester 13, the new mixture of ester was then exposed to deprotection conditions, and the resulting acids were then coupled with tetra (ethylene glycol) derivative 20 to yield a mixture of benzyl ethers (M0-M4). Hydrogenolysis of the benzyl ether mixture gave a mixture of five fluorinated dendrons and their side products. The mixture can then be separated by HPLC on FluoroFlash® column to give each generation of pure fluorinated dendron amphile on 300-mg scales, except generation four. The overall yield after chromatographic purification is high for the first four generations (G0 (87%), G1 (88%), G2 (81%), and G3 (71%)). For the G4, the target compound and sideproducts formed an inseparable mixture by HPLC.

Figure 8:
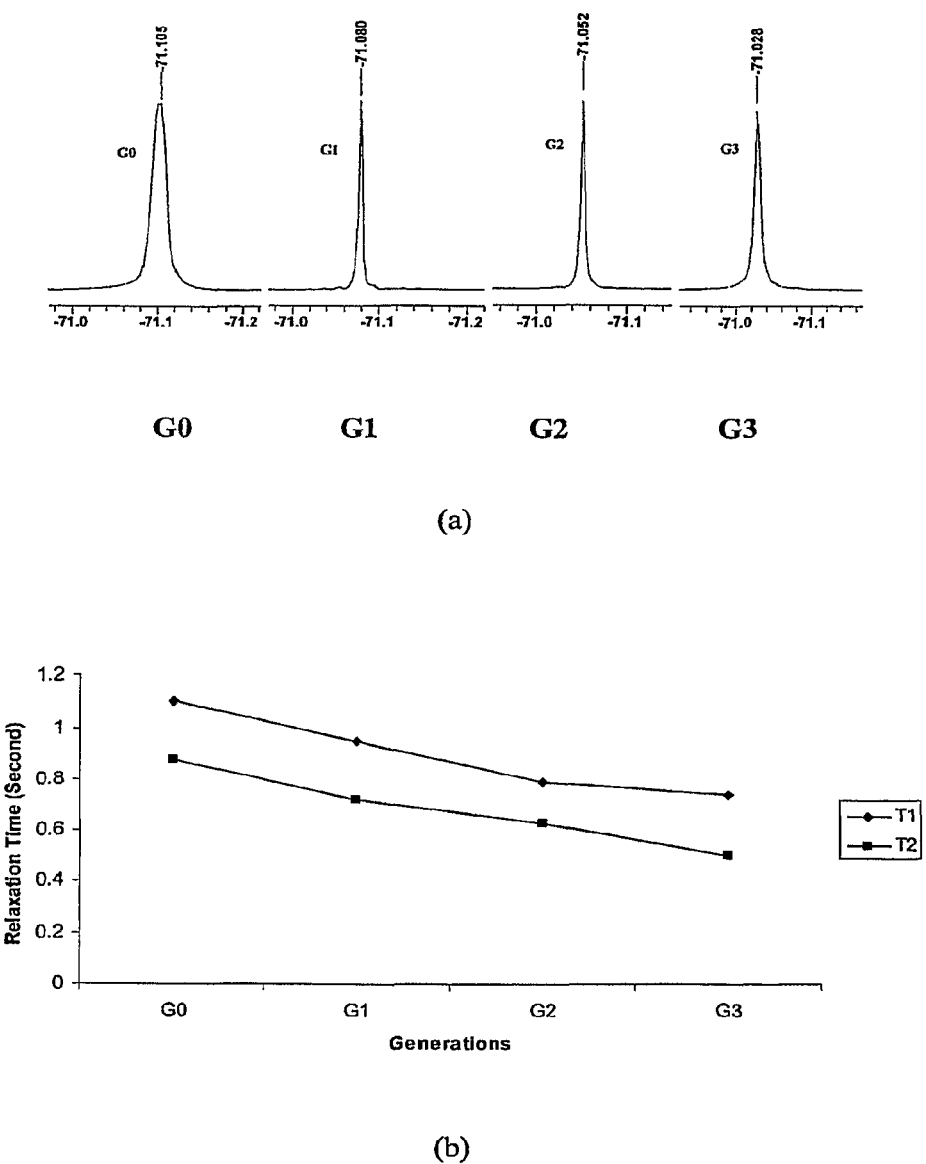
FIG. 8 shows (a) singlet $^{19}$F NMR peak of G0-G3 (25° C., 0.025M in CD$_3$OD, 376 MHz) and (b) T1 and T2 increase with molecular weight [T1 & T2 of G0-G3 ($^{19}$F, 25° C., 0.025M in CD$_3$OD, 376 MHz)].
Figure 9:
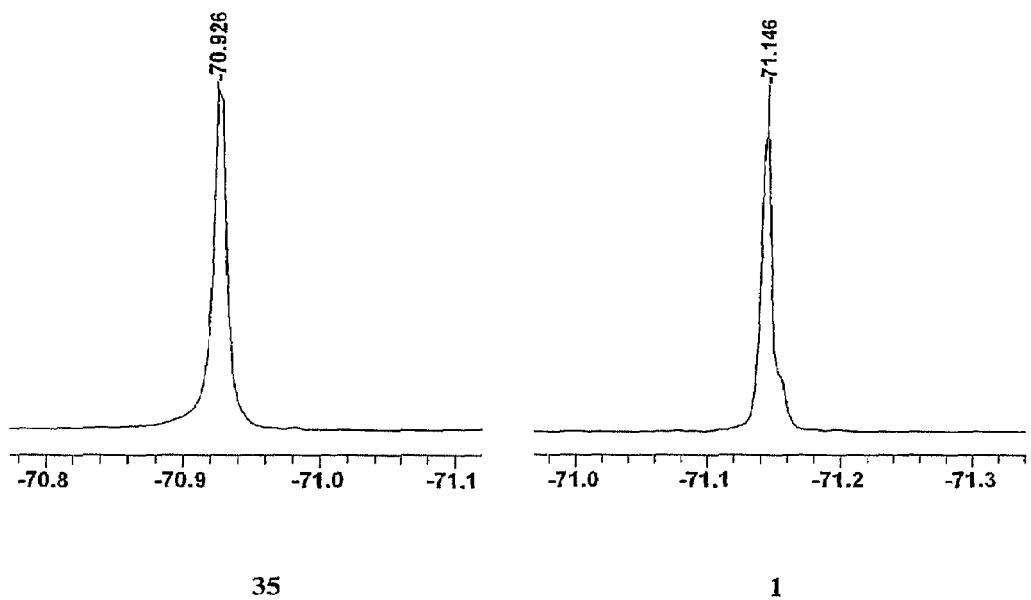
FIG. 9 shows $^{19}$F NMR spectra of chelator 35 and 1 (0.025 M in CD$_3$OD, 376 MHz).

With the four generations of fluorinated dendron amphiles in hand, some NMR experiments were carried out on G0-G3. All twenty-seven fluorine atoms in each generation of amphile give only one sharp singlet $^{19}$F NMR peak, which is ideal for $^{19}$F MR imaging (FIG. 5a). Also, T1 and T2 of G0-G3 increase with molecular weight (FIG. 8b).

N. FLUORINATED DENDRONS AS DRUG DELIVERY VEHICLES

In one aspect, fluorinated dendrons can be prepared according to Schemes 3-9.

Scheme 3. Synthesis of Amine 24.

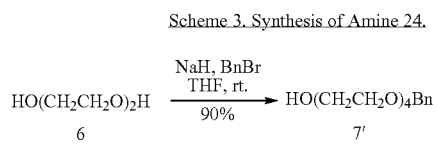

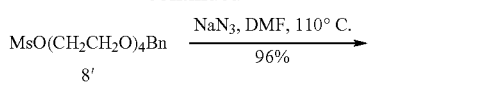

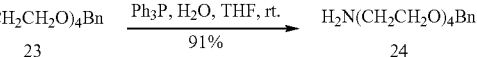

Scheme 2. Synthesis of Amine 26 (G0).

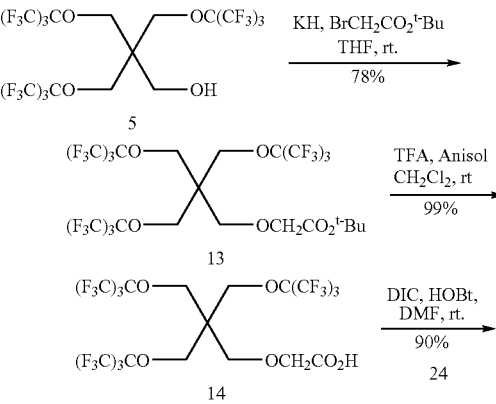

Scheme 5. Synthesis of F-surf 28 (G1).

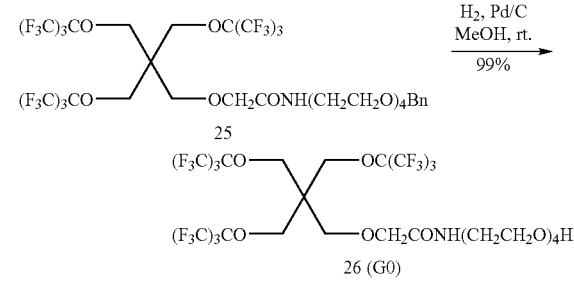

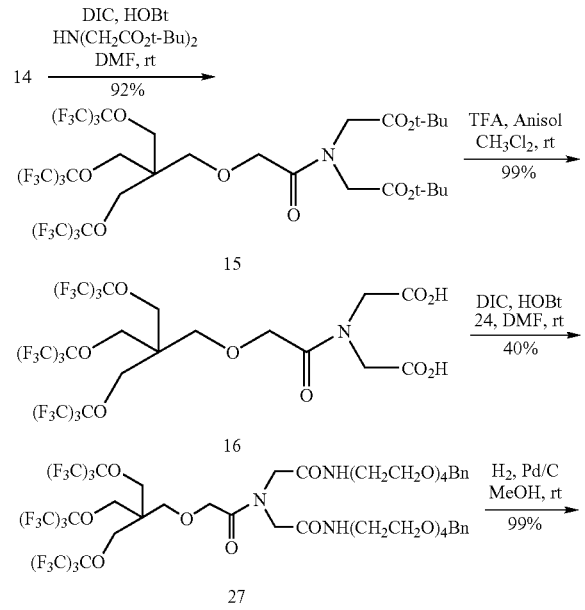

-continued
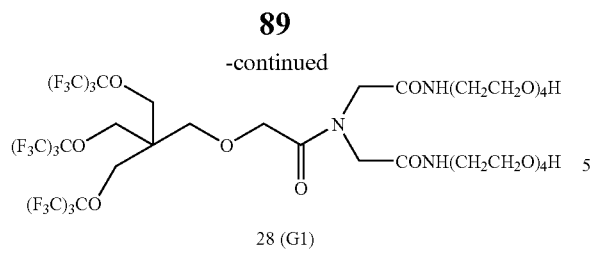
28 (G1)
Scheme 6. Synthesis of F-surf 30 (G2).
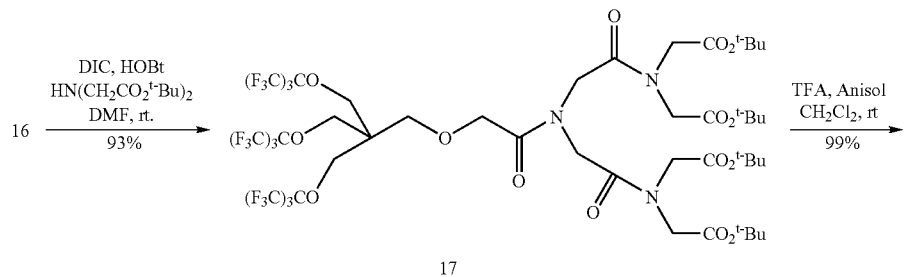
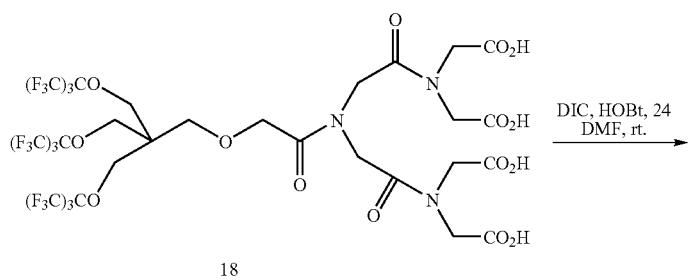
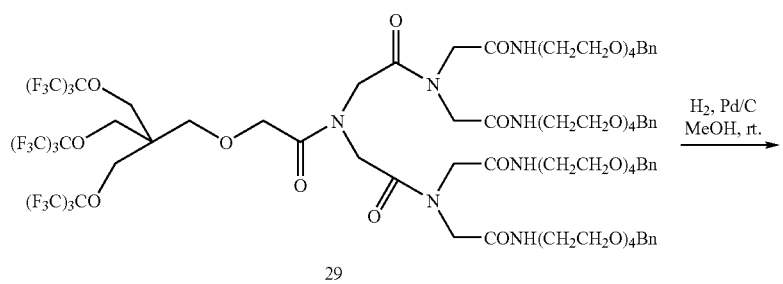
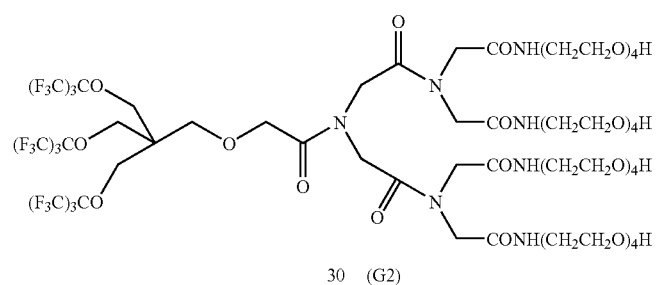
30 (G2)

Scheme 7. Synthesis of F-surf 32 (G3).
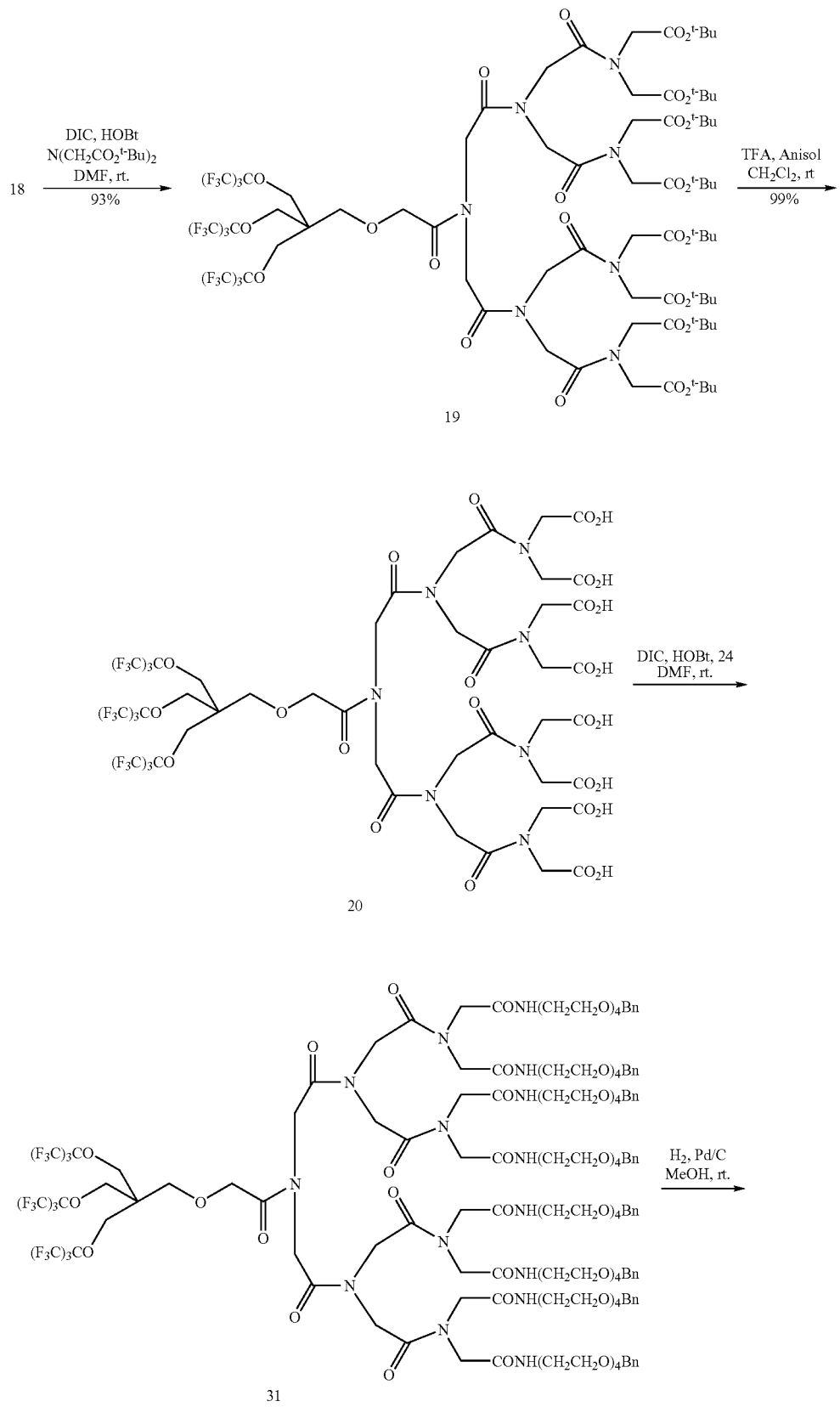

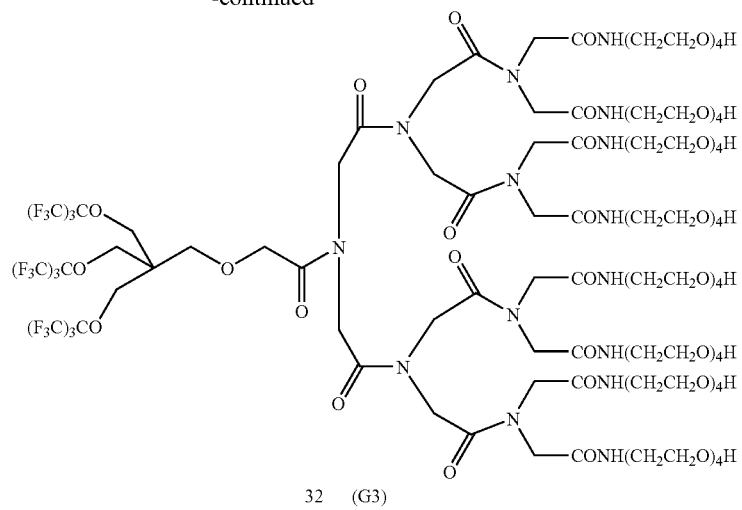
32 (G3)

Scheme 8.
Mixture Synthesis:
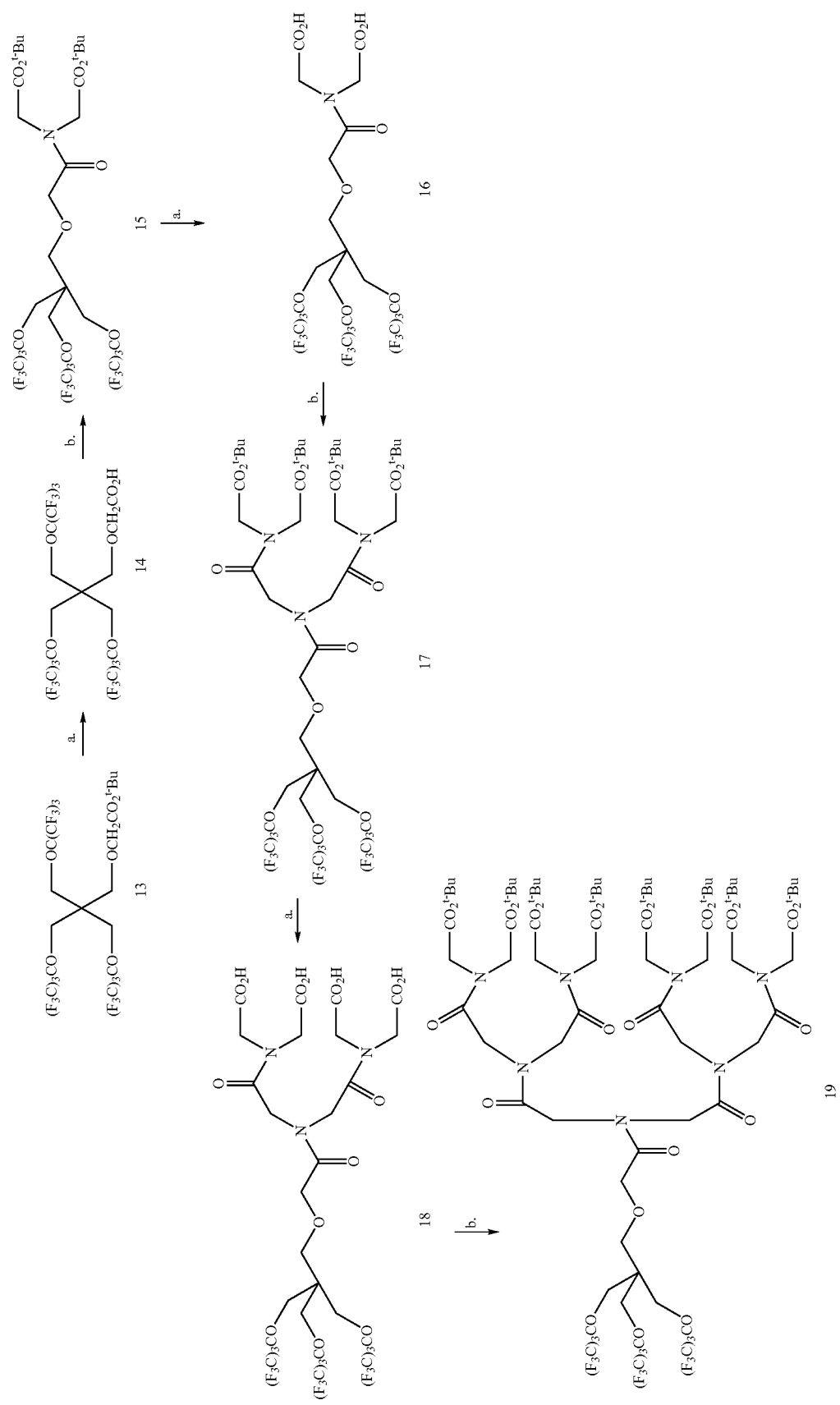
a. TFA, (iPr)₃SiH, CH₂Cl₂, rt, 2h.
b. DIC, HOBt, HN(CH₂CO₂tBu)₂, rt. overnight Starting material 13 (4.0 mmol, 3.62 g) was subjected to deprotection and coupling to provide pure 16 (Flash chromatography on F-silica gel purification gave 16 (3.96 g, 92% over all yield, 3.68 mmol)). After transferral of a portion of compound 16 (0.40 mmol, 430 mg) to a flask A, the remainder of compound 16 (3.27 mmol, 3.52 g) was then subjected to deprotection and coupling to provide pure compound 17 (Flash chromatography F-silica gel purification gave 17 (4.22 g, 2.98 mmol, 91% overall yield)). After transferral of a portion of compound 17 (0.3 mmol, 425 mg) to the flask A, the remainder of compound 17 (3.79 g, 2.68 mmol) was then subjected to deprotection and coupling to provide pure compound 19 (Flash chromatography F-silica gel purification gave 19 (4.84 g, 86% overall yield, 2.30 mmol)). After transferral of portions of compound 19 (0.2 mmol, 421 mg) and compound 13 (0.6 mmol, 543 mg) into the flask A, the mixture of starting material was put into the mixture synthesis.

Generation 0

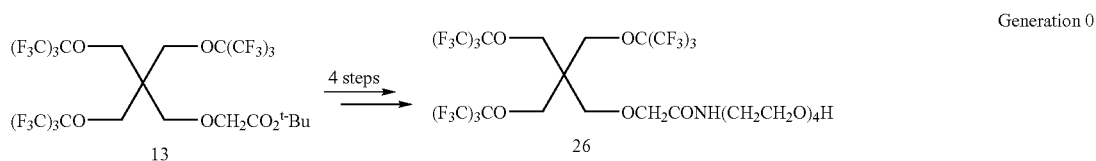

Generation 1

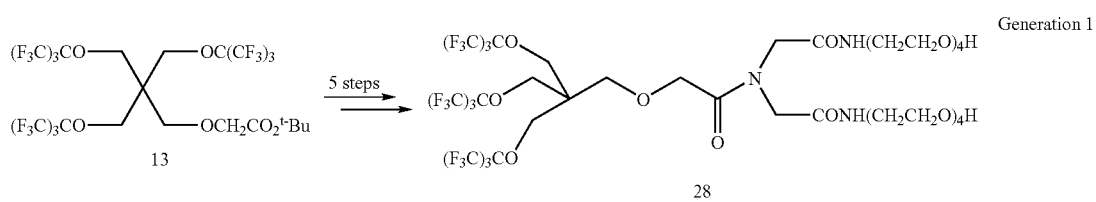

Generation 2

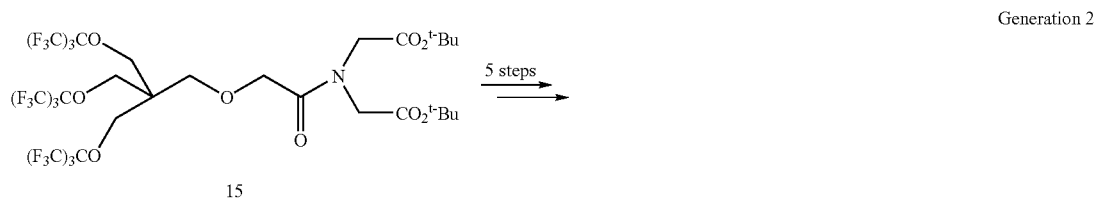

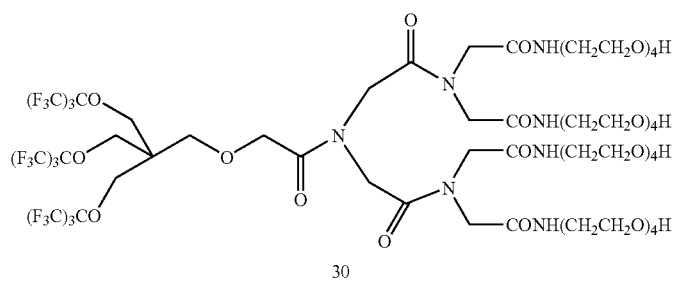

-continued
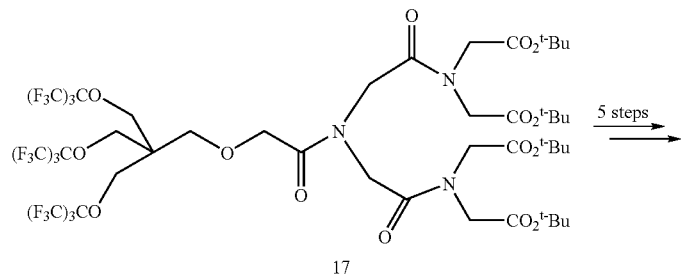
17
5 steps →
Generation 3
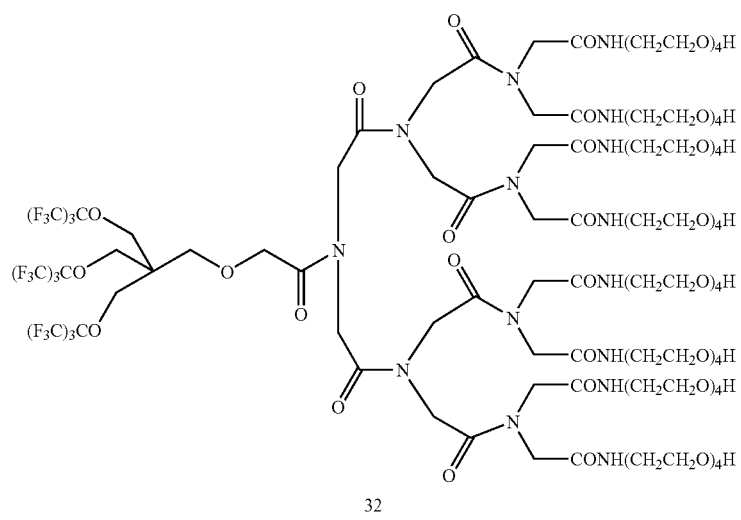
32
Generation 4
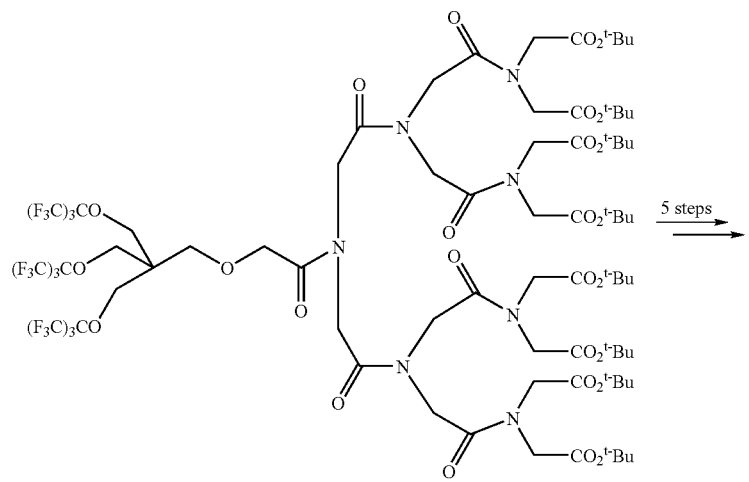
18
5 steps →

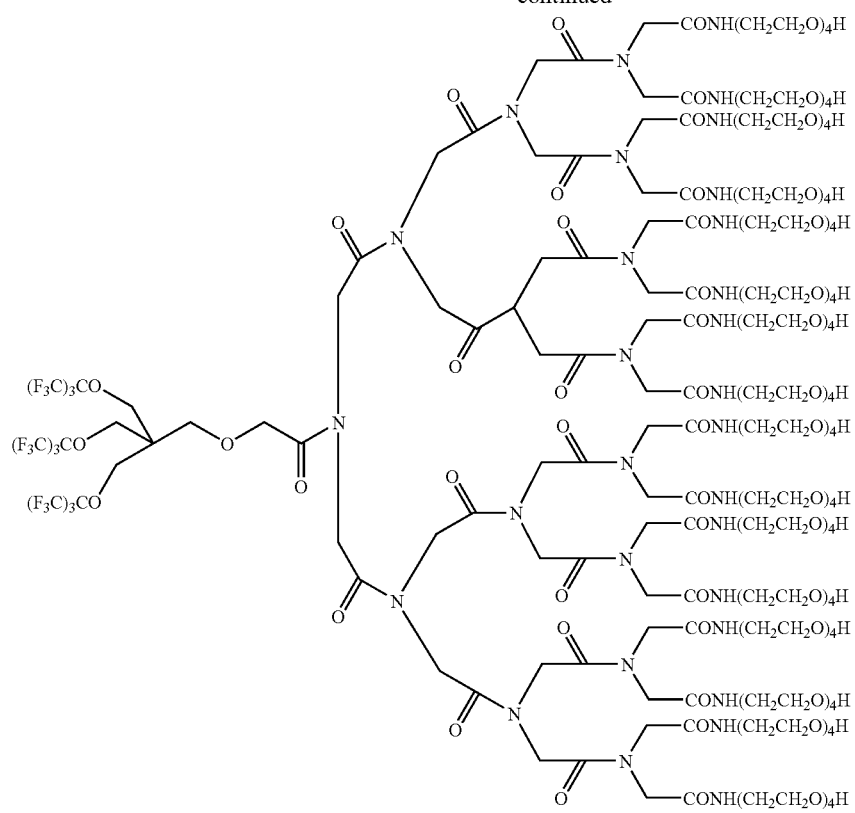

34

| Reaction Conditions | | | | | |
|---|---|---|---|---|---|
| Starting Material | 13 | 13 | 16 | 17 | 19 |
| | MW | MW | MW | MW | MW |
| | 904.35 | 904.35 | 1075.54 | 1417.93 | 2102.71 |
| Input of SM | 0.6 mmol | 0.5 mmol | 0.4 mmol | 0.3 mmol | 0.2 mmol |
| | 542.61 mg | 452.18 mg | 430.22 mg | 425.38 mg | 420.54 mg |
| Step 1 | | | | | |
| Amount of ester (4.1 mmol total) | | 0.5 mmol | 0.8 mmol | 1.2 mmol | 1.6 mmol |
| Deprotection | DCM (24 mL); TFA (16 mL), Anisol (1 mL), rt 2 h | | | | |
| Work up | Removal of solvent, the residue was evaporated with toluene (30 mL) twice to dryness and put into the next step. | | | | |
| Step 2 | | | | | |
| Amount of acid (4.1 mmol total) | | 0.5 mmol | 0.8 mmol | 1.2 mmol | 1.6 mmol |
| $HN(CH_2CO_2\text{-}^tBu)_2$ MW 245.32; 3 eq. 12.3 mmol, 3.02 g | | 1.5 mmol | 2.4 mmol | 3.6 mmol | 4.8 mmol |
| DIC MW 126.2, d = 0.815; 3 eq. 12.3 mmol, 1.552 g, 1.9 mL | | 1.5 mmol | 2.4 mmol | 3.6 mmol | 4.8 mmol |
| HOBt MW 135.1, 3 eq. 12.3 mmol, 1.662 g | | 1.5 mmol | 2.4 mmol | 3.6 mmol | 4.8 mmol |
| Work up | Reaction in DMF (40 mL) overnight. 1. Addition of 6 mL water to the reaction mixture 2. Load to the F-silica gel column (100 g) 3. Washed with MeOH/Water (8:2, 100 mL) 4. Washed with MeOH/TFE (8/2, 200 mL) and colleted the fraction 5. Washed with Acetone (200 mL 6. collected 4 & 5, removal of solvent to dryness | | | | |

-continued

| Reaction Conditions | | | | | |
|---|---|---|---|---|---|
| Step 3 | | | | | |
| Amount of ester (8.8 mmol total) | 0.6 mmol | 1.0 mmol | 1.6 mmol | 2.4 mmol | 3.2 mmol |
| Deprotection (Twice) | DCM (48 mL); TFA (32 mL), rt 2 h | | | | |
| Work up | Removal of solvent, the residue was evaporated with toluene (30 mL) to dryness and put into the next step. | | | | |
| Step 4 | | | | | |
| Amount of acid (8.8 mmol total) | 0.6 mmol | 1.0 mmol | 1.6 mmol | 2.4 mmol | 3.2 mmol |
| $H_2N(CH_2CH_2O)_4Bn$ MW 283.4, 26.4 mmol, 7.482 g | 1.8 mmol | 3.0 mmol | 4.8 mmol | 7.2 mmol | 9.6 mmol |
| DIC MW 126.2, d = 0.815; 3 eq. 26.4 mmol, 3.332 g, 4.01 mL | 1.8 mmol | 3.0 mmol | 4.8 mmol | 7.2 mmol | 9.6 mmol |
| HOBt MW 135.1, 3 eq. 26.4 mmol, 3.567 g | 1.8 mmol | 3.0 mmol | 4.8 mmol | 7.2 mmol | 9.6 mmol |
| Work up | Reaction in DMF (50 mL) overnight. 1. Addition of 6 mL water to the reaction mixture 2. Load to the F-silica gel column (100) 3. Washed with MeOH/Water (8:2, 30 mL) 4. Washed with MeOH (40 mL) and colleted the fraction 5. Washed with Acetone (40 mL) | | | | |
| Step 5 | | | | | |
| To a stirred solution of crude products in Methanol 100 mL was added Pd/C (2 g). After degassed for 5 min, the resulting suspension was stirred under an atmosphere of hydrogen gas overnight. After filtrated though a pad of Celite, the solution was concentrated under vacuum and purified by HPLC to give the 5 products. | | | | | |

O. HIGHLY FLUORINATED CHELATORS FOR $^1H$-$^{19}F$ MULTINUCLEAR MAGNETIC RESONANCE IMAGING

Multinuclear MR imaging, such as $^1H$-$^{31}P$ and $^1H$-$^{23}Na$, is playing an increasingly important role in cancer research and holds great potential for cancer diagnosis and intervention. Compared with other nuclei, $^{19}F$ has a sensitivity of only second to $^1H$ (83% as sensitive) and has negligible background interference in human tissues. Thus, areas of interest can be quickly identified based on Gd(M)-enhanced $^1H_2O$ signals, and a more accurate quantification can be based on the $^{19}F$ signal, by using a $^1H$-$^{19}F$ multinuclear MR reagent with the same imaging modality.

When conjugated to a drug, local drug concentration can be measured by $^{19}F$ MRI and hence an image-based dosing for each patient (individualized doimetry) can be developed. Moreover, $^{19}F$ MR relaxometry is a well-established non-invasive method for oxygen tension determination and is the only NMR technique to determine the absolute value of oxygen tension. The significance of oximetry in radiotherapy lies in the fact that oxygen tension plays a role in tumor hypoxia and sensitivity toward radiation.

However, conventional $^{19}F$ MR imaging studies typically employ either linear fluorocarbons (such as perfluorooctyl bromide), which exhibit a multipeak-spectra resulting in $^{19}F$ MR imaging with chemical shift artifacts, or perfluoro-15-crown-5, which —$CF_2$— groups are significantly less sensitive than —$CF_3$ group toward oxygen tension in $^{19}F$ oximetry. Therefore, the synthesis of novel —$CF_3$ group rich fluorinated MR imaging reagents with a single sharp resonance peak is desirable to optimize current $^{19}F$ MR imaging study.

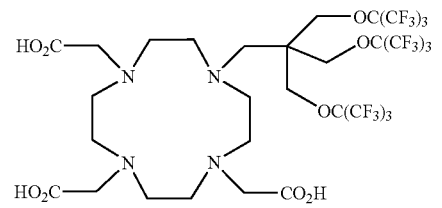

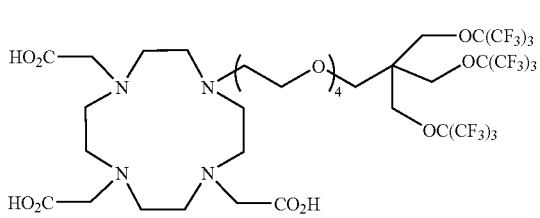

Two highly fluorinated DOTA derivatives (35 and 1) were prepared. These structures were selected based upon the following criteria: Firstly, cyclic chelator DO3A was chosen for $^1H$ MRI since it has the highest stability toward Gd(M) among the chelators currently used in clinic. Secondly, perfluoro-tert-butyl ether was used for $^{19}F$ MR imaging because of its high $^{19}F$ signal intensity (twenty-seven chemical identical fluorine atoms) and high stability (stable to base and acid). Finally, a tetraethylene glycol chain was introduced in compound 1 to avoid the possibility of the bulky and highly hydrophobic fluorinated ether part hampering the chelation process and reduce the water solubility.

The synthesis of target molecules 35 and 1 commenced with the preparation of common building block 5 (Scheme 10). Protection of pentaerythritol 2 as the orthoacetate, followed by protection of the fourth hydroxyl group with benzyl bromide and hydrolysis of the orthoacetate, finished the corresponding triol 3. After triol 3 was reacted with nonafluoro-tert-butanol to provide the perfluoro-tert-butyl ether 4, the benzyl group in ether 4 was removed by aluminum chloride to afforded desired heavy fluorinated alcohol 5 on a 50-gram scale.

F362 extraction with an 88% yield. The reaction of compound 37 with ethyl bromoacetate in the presence of potassium carbonate in a mixture of tetrahydrofuran/dimethylformamide (1/1) at 60° C. provided triethylester 38 with an excellent yield. Finally, hydrolysis of the triethylester with lithium hydroxide in water and methanol afforded 35 with a 97% yield.

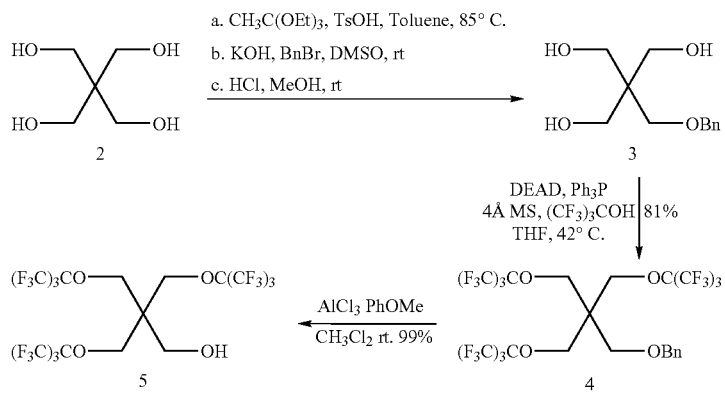

With building block 5 in hand, the target molecule 1 was then synthesized (Scheme 11). Treatment of alcohol 5 with trifluoromethanesulfonic anhydride in the presence of pyridine gave trifluoromethanesulfonate 36 with excellent yield by simply phase separation after the addition of a small amount of water to the reaction mixture.

Linker 8' was synthesized in good yield on a 50-gram scale from commercially available tetraethylene glycol 6 by selective protection of one of the hydroxyl groups with benzyl bromide and transformation of the other hydroxyl group into the corresponding methanesulfonate (Scheme 12).

Scheme 12. Preparation of methanesulfonate 8'.

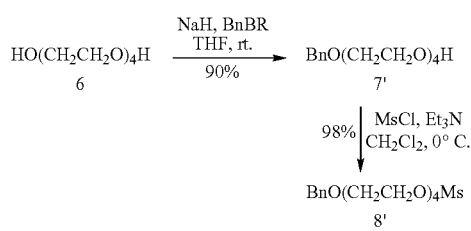

Scheme 11. Synthesis of fluorinated DOTA 35.

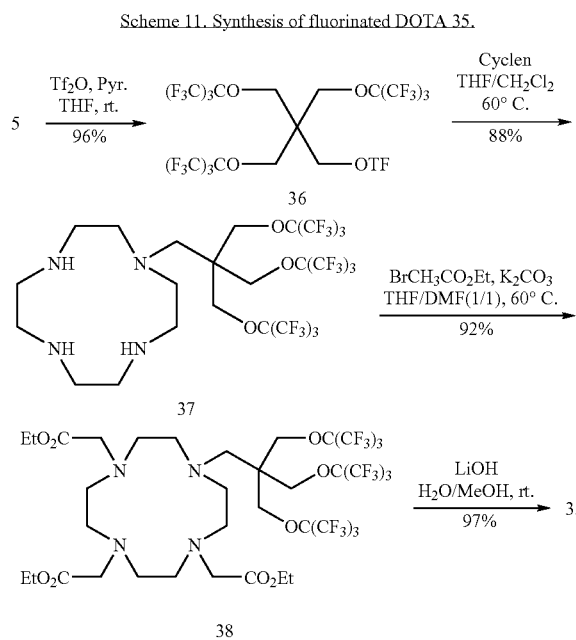

Tetrahydrofuran is an excellent solvent for this reaction due to good solubility of alcohol 5. The fluorinated fragment was then conjugated to the cyclene ring by reaction of trifluoromethanesulfonate 36 with two equivalents of cyclene in a mixture of tetrahydrofuran and dichloromethane (1/1) at 60° C. overnight. The pure product 37 was isolated by simple In the synthesis of DOTA 1 (Scheme 13), the heavily fluorinated alcohol 5 was first attached to the hydrophilic tetraethylene glycol chain to provide compound 9 in good yield by treating the alcohol 5 with potassium hydride in tetrahydrofuran at room temperature for 30 minutes, then slowly addition of the methanesulfonylate 8' at the same temperature. Due to the three bulky perfluoro-tert-butyl group in compound 5, use of sodium hydride as a base resulted in recovery of the alcohol 5 and methanesulfonylate 8' only after a long reaction time. Then, removal of the benzyl group in compound 9 by palladium hydroxide catalyzed hydrogenolysis gave alcohol 10 with an excellent yield, which was then treated with methanesulfonyl chloride and triethyl amine to give the methanesulfonylate 11 in a quantitative yield. Attaching the cyclene ring to the fluorinated moiety was achieved by treating compound 11 with two equivalents of cyclene at 60° C. Purification of the resulting cyclene derivative 12 from the reaction mixture was laborious. Then solid phase extraction on fluorinated silica gel was employed, and compound 12 was isolated with a 93% yield. Compound 12 was reacted with ethyl bromoacetate in the presence of potassium carbonate in dimethylformamide at 60° C. provided tri-ethyl ester 13 with an excellent yield. Finally, treatment of compound 13 with lithium hydroxide in water and methanol gave 1 with a 99% yield.

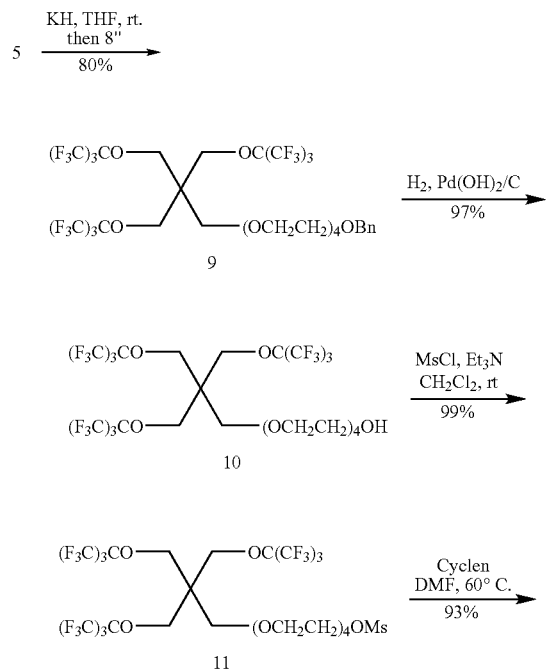

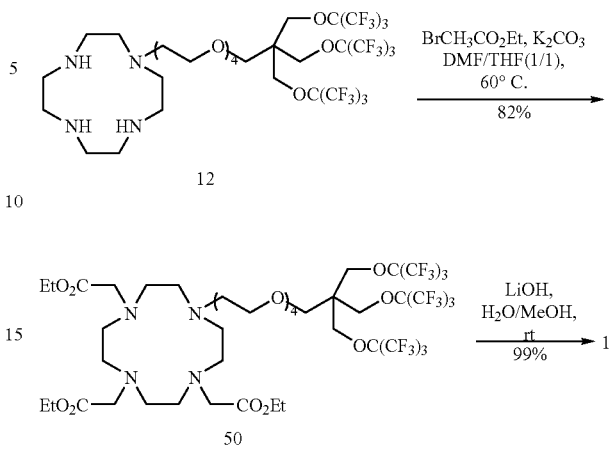

P. HIGHLY FLUORINATED DENDRON CHELATORS

Using methods analogous to those disclosed herein, highly fluorinated dendron chelators, which combine features of fluorinated dendrons as drug delivery vehicles and highly fluorinated chelators for $^1$H-$^{19}$F multinuclear magnetic resonance imaging, can be prepared. Exemplary compounds include:

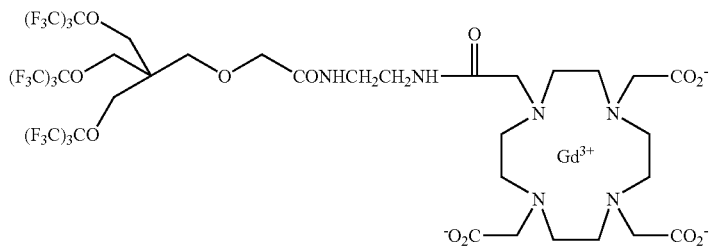

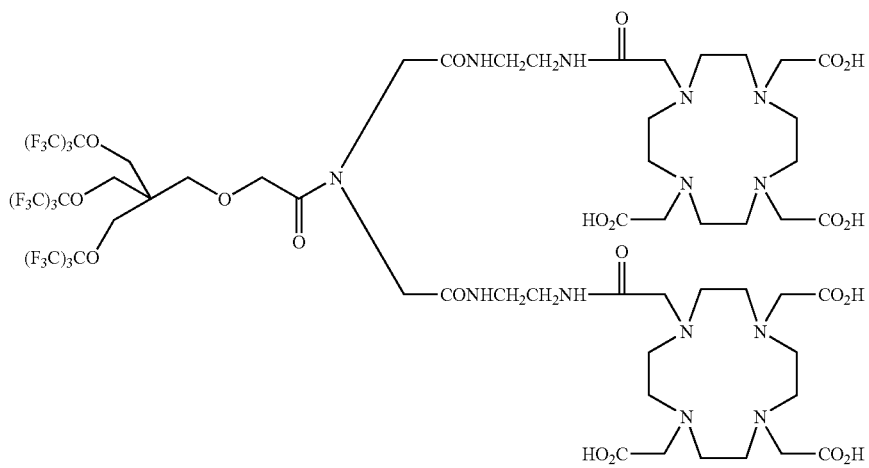

-continued
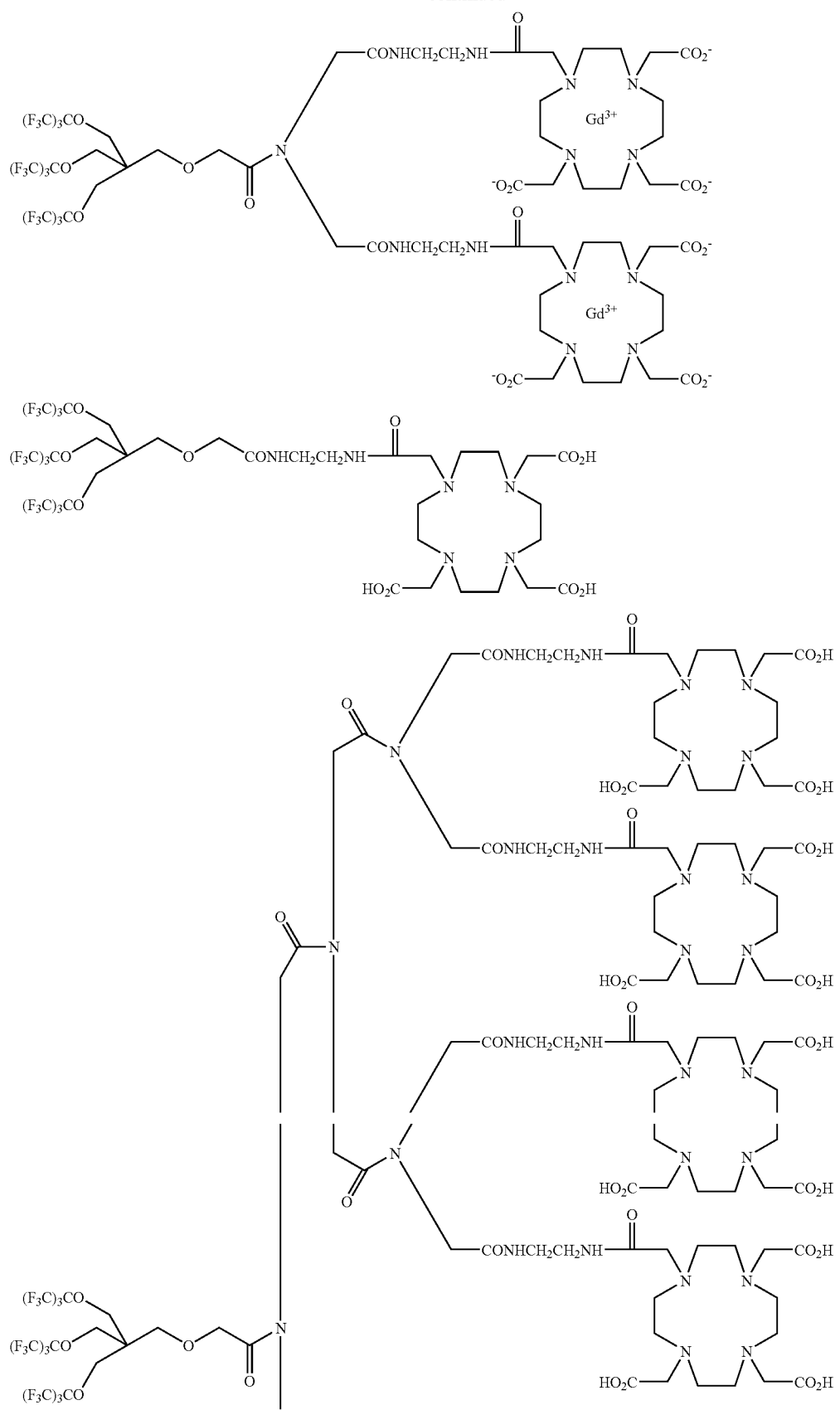

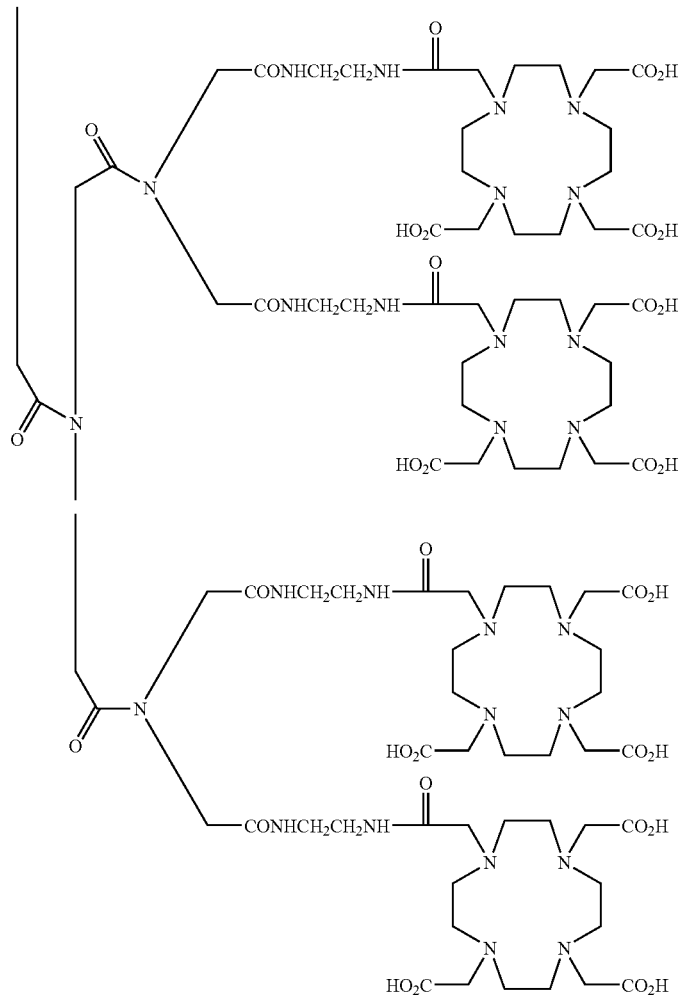
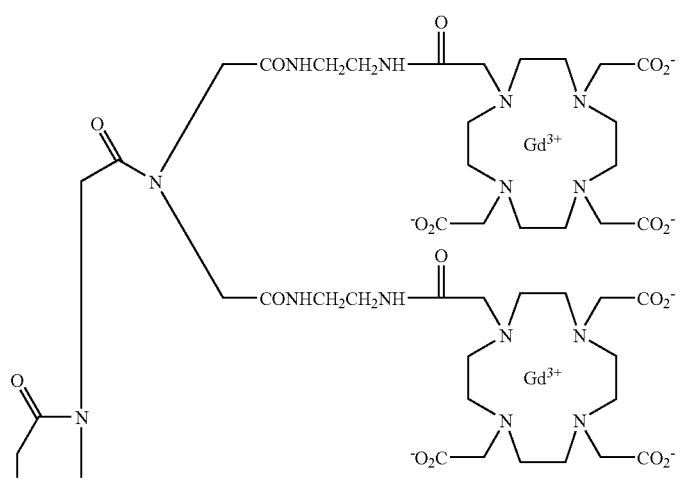

-continued
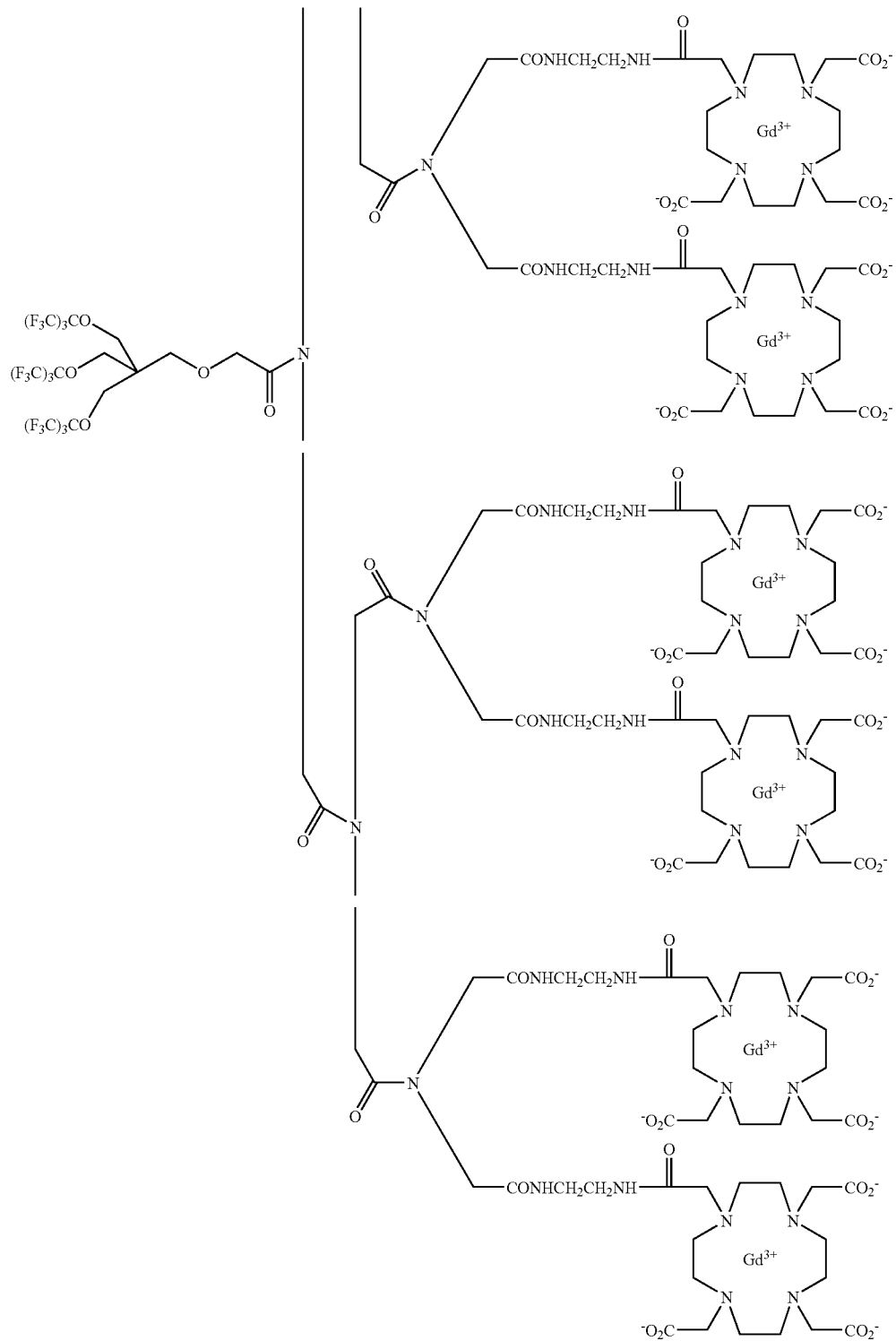

-continued
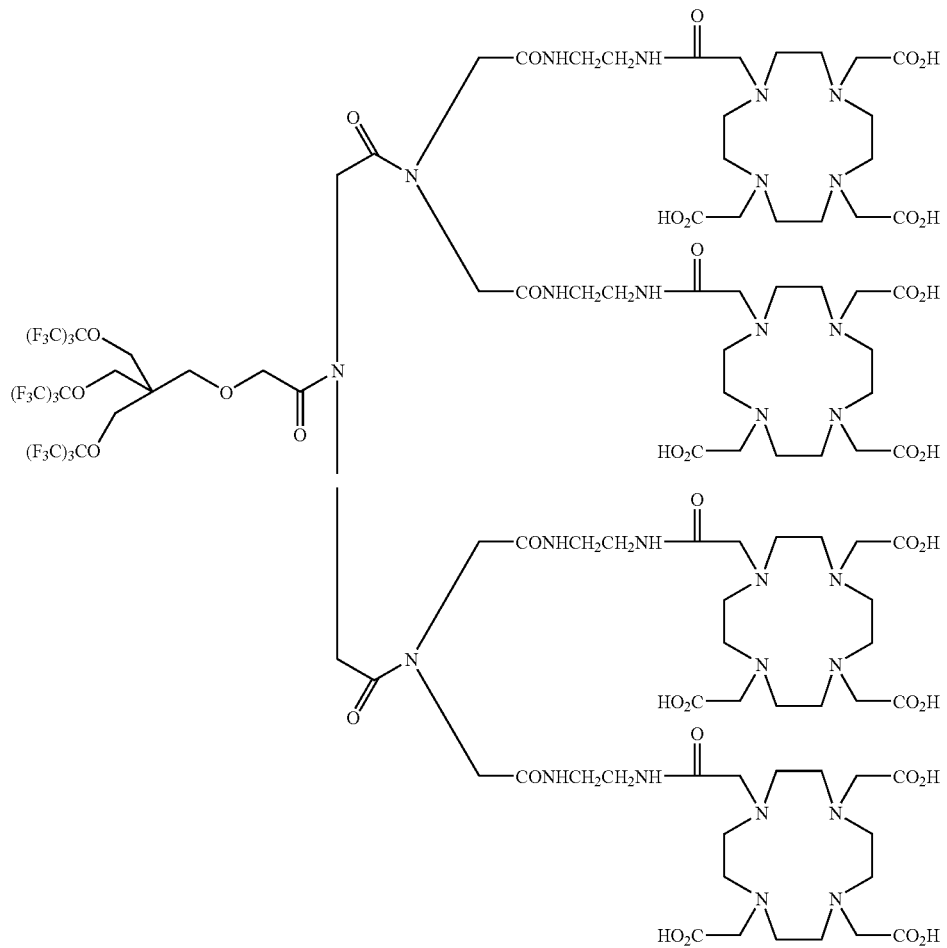
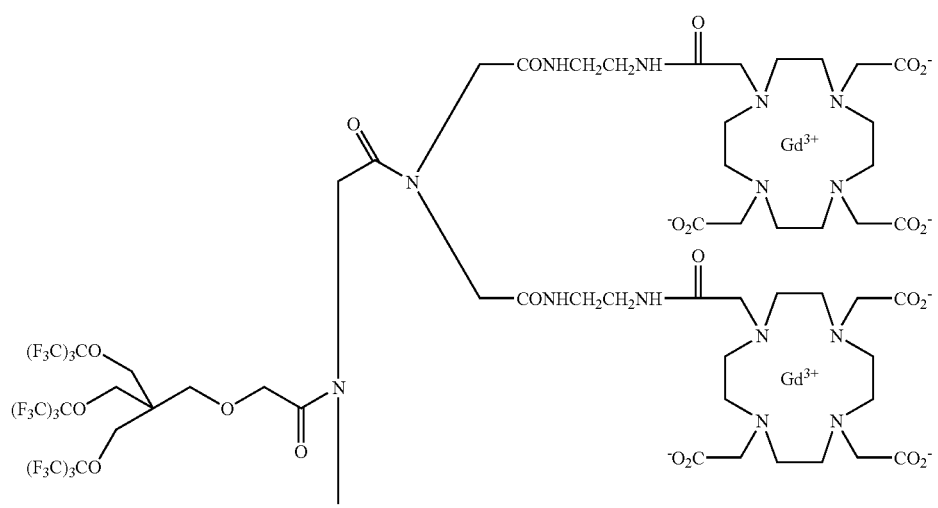

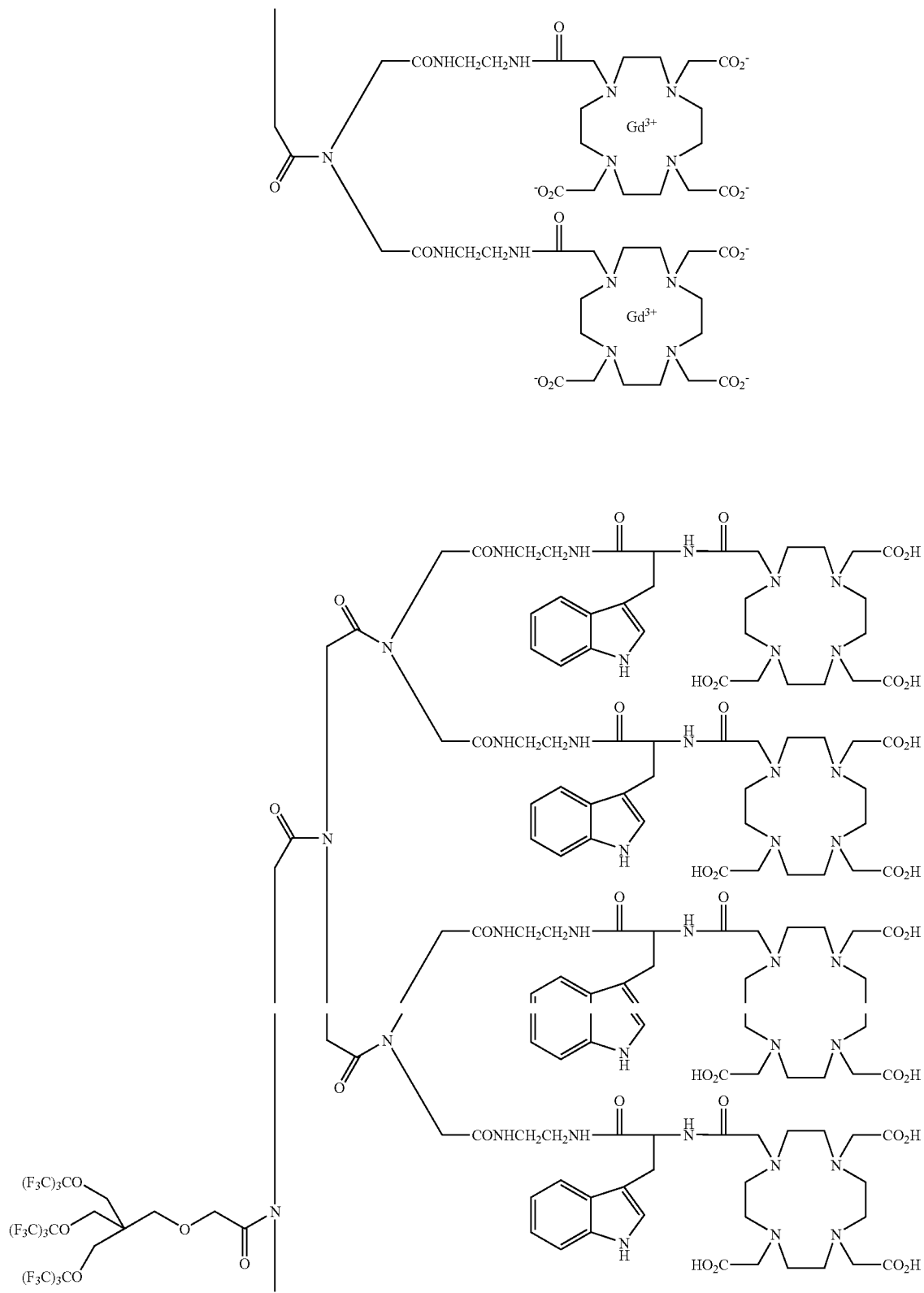

-continued
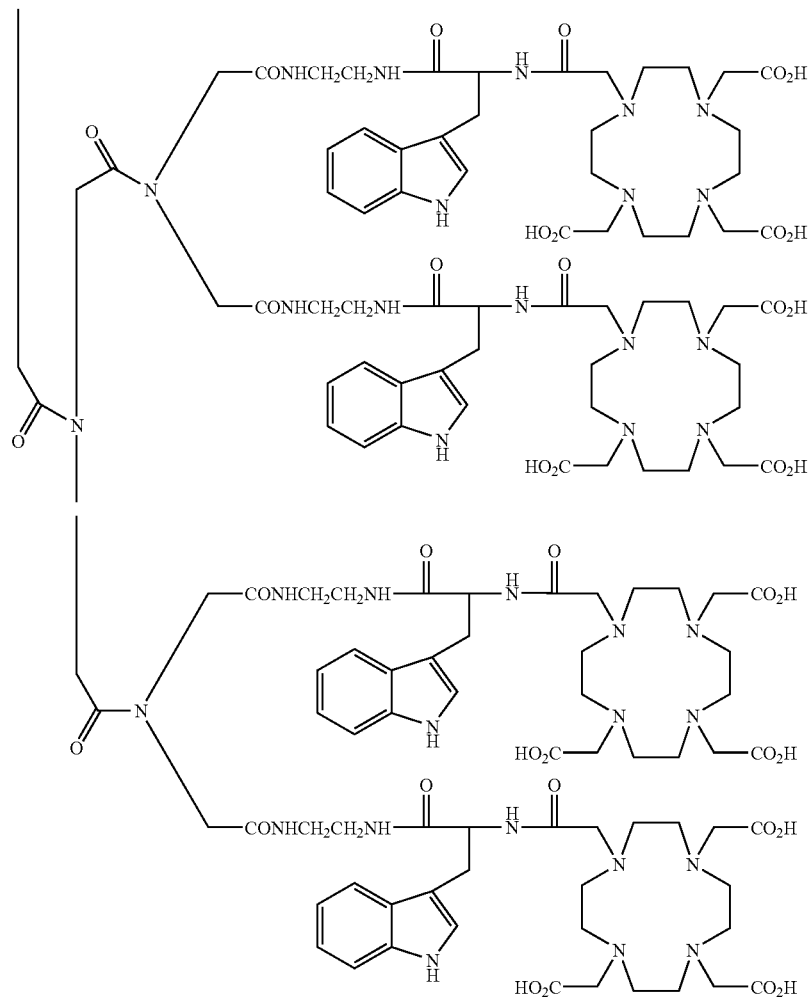
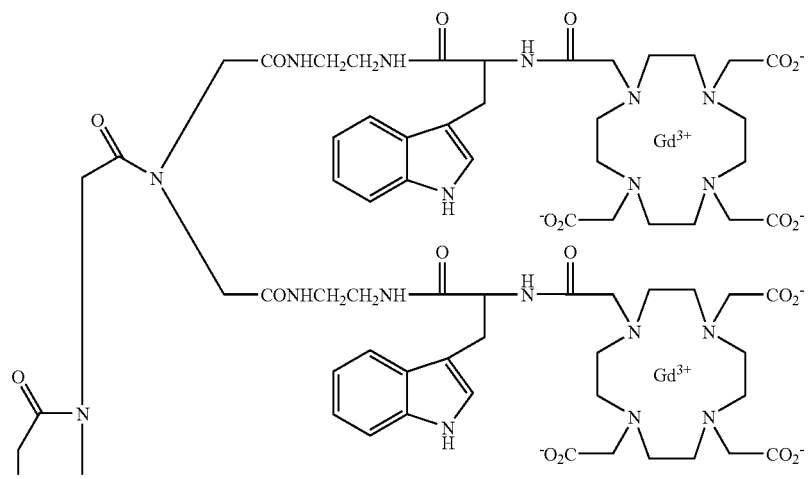

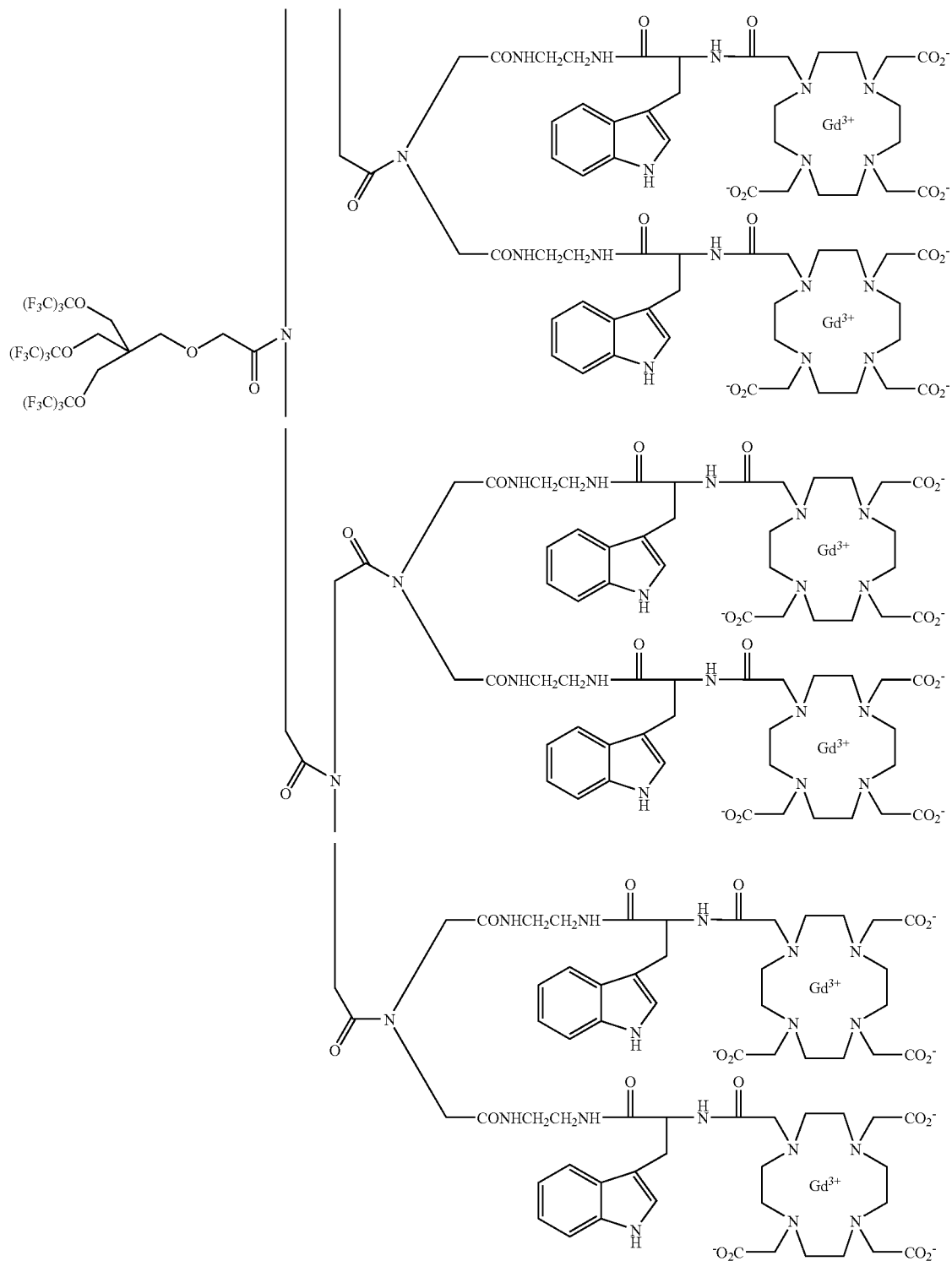

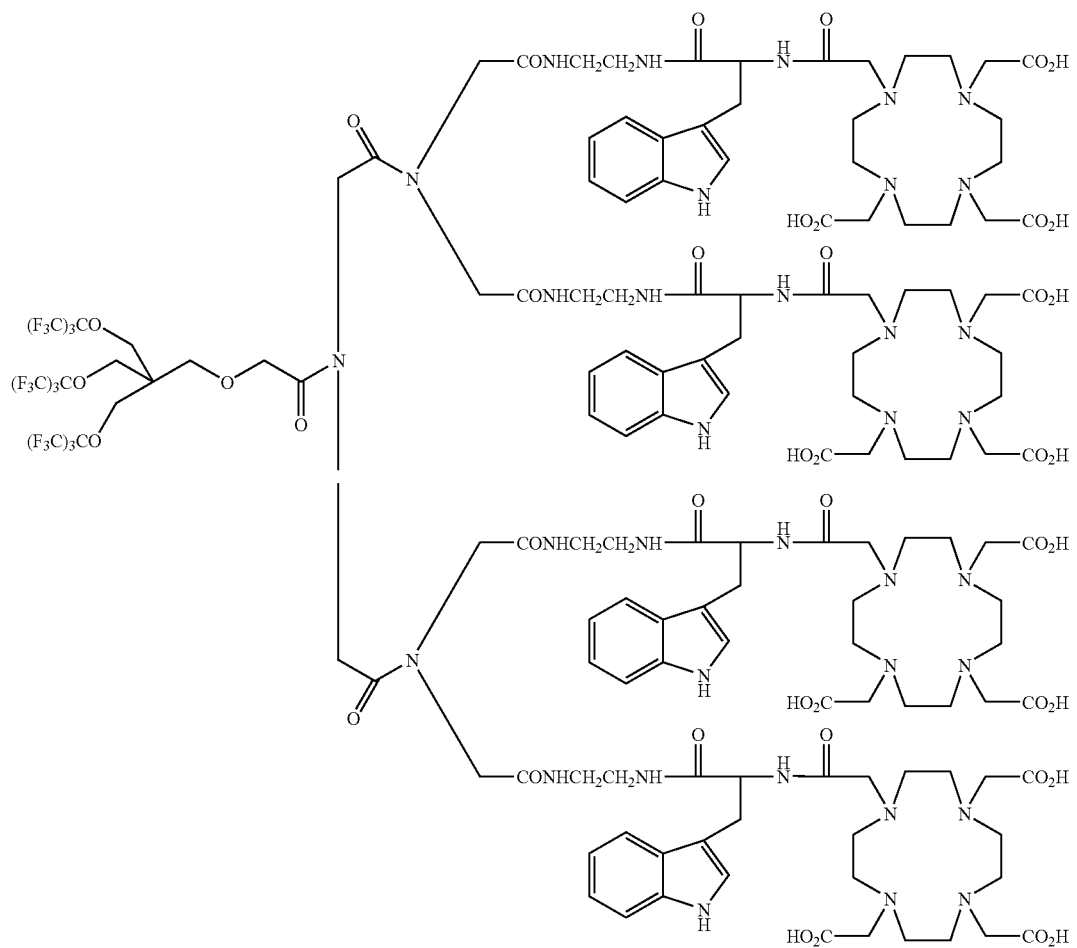
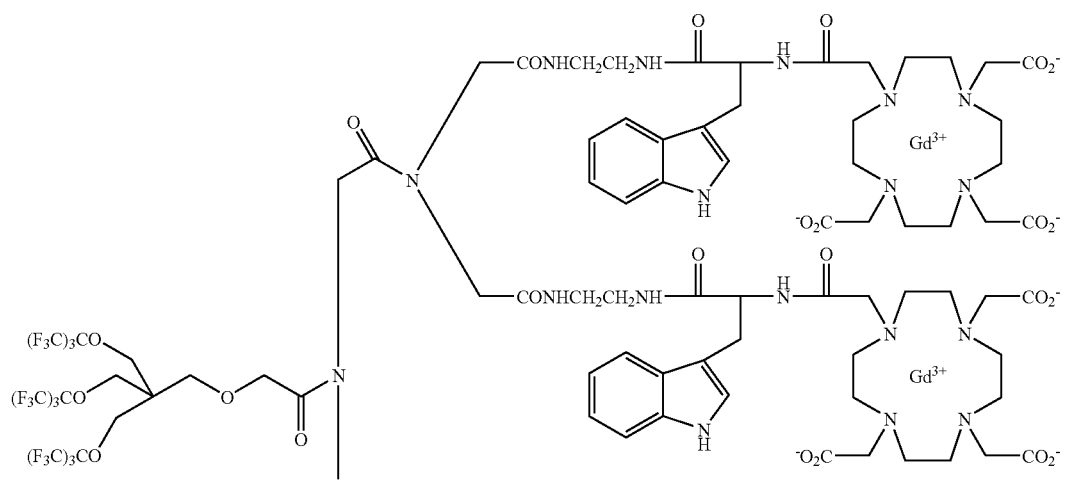

-continued
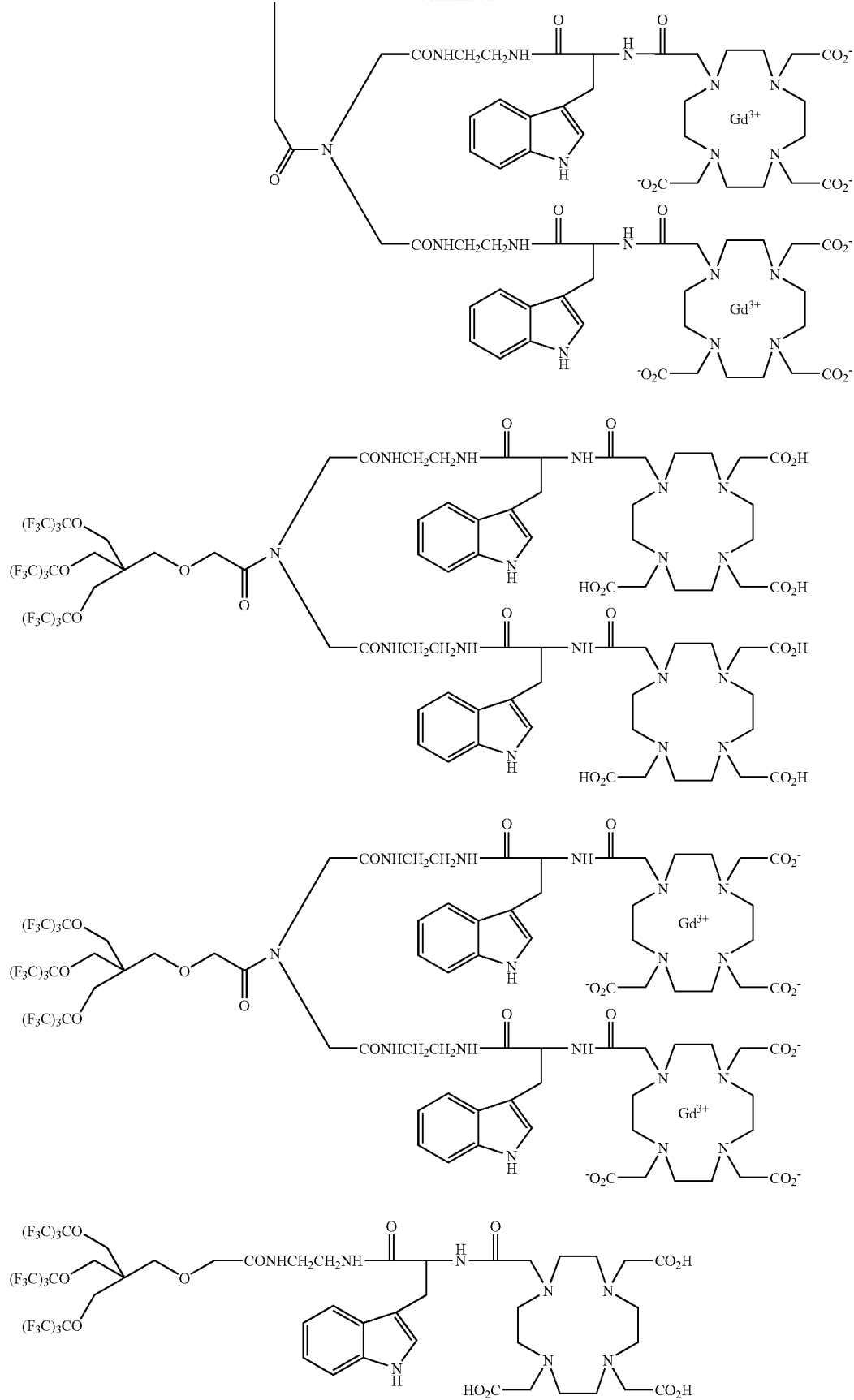

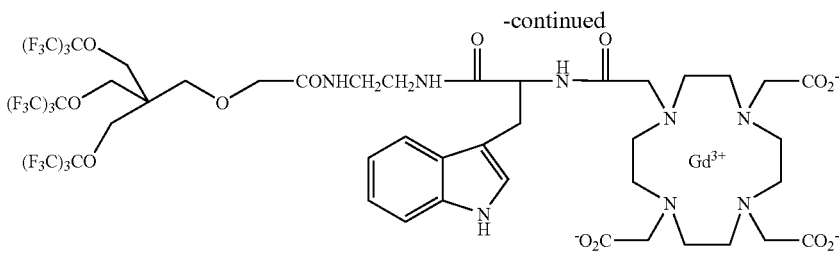

Q. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Unless otherwise indicated, reference numbers used in the synthetic procedures refer to the immediate schematic diagram.

1. Synthesis of Surfactant with —OH Ending Group methanol (100 mL) and treated with 0.01 N HCl (400 mL). The resulting mixture was stirred at 25° C. for 1 h, treated with sodium bicarbonate (14.5 g, 173.0 mmol), stirred for an additional 1 h, and concentrated. Trituration of the resulting solid residue with methanol (200 mL) and concentration of the triturate afforded 19.4 g (55%) of compound 3 as a colorless viscous oil. $^1$H NMR (CD$_3$OD) δ 3.34 (s, 2H), 3.55 (s, 6H), 4.37 (s, 2H), 7.17-7.33 (m, 5H).

b. Synthesis of Compound 4

To a mixture of compound 3 (30.1 g, 128 mmol), triphenylphosphine (150.7 g, 575 mmol) and 4 Å molecular sieve (30.0 g) in tetrahydrofuran (500 mL) at 0° C. was added dropwise diethylazodicarboxylate (100.0 g, 575 mmol). After the addition, the reaction mixture was allowed to warm to room temperature and stirred for additional 20 minutes. Then perfluoro-tert-butanol (135.7 g, 575 mmol) was added in one portion and the resulting mixture was stirred at 45° C. for 30

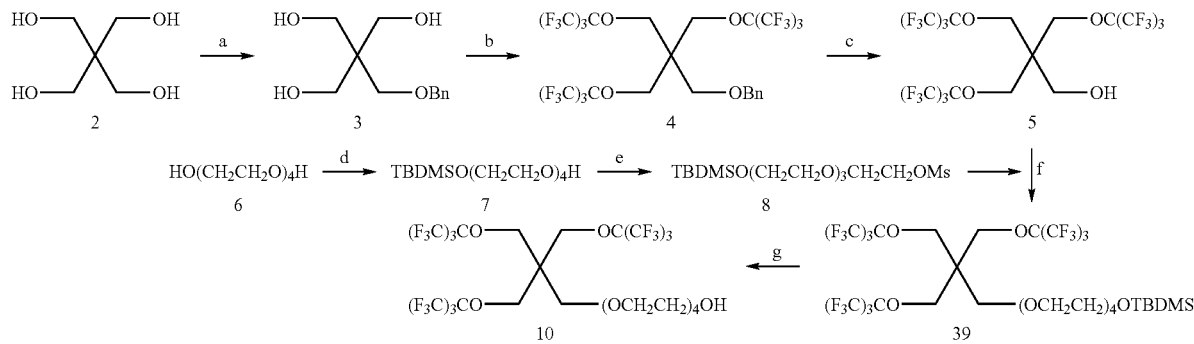

a. Synthesis of Compound 3

To a suspension of pentaerythritol 2 (21.2 g, 156 mmol) in toluene (20 mL) was added triethyl orthoacetate (25.3 g, 156 mol) and p-toluenesulfonic acid monohydrate (100 mg). The resulting mixture was gradually heated with an oil bath, and ethanol was slowly distilled from the mixture overnight. After all ethanol had distilled, the bath temperature was raised to 125° C. and toluene was distilled off until the solution was homogeneous. The solution was allowed to cool and the residue was used in the next step without further purification. Powdered KOH (41.2 g, 734.3 mmol) was suspended in dimethyl sulfoxide (250 mL), and this mixture was stirred at room temperature for 15 min. The residue from the former step (25.0 g, 156 mmol) was added in one portion followed quickly by benzyl bromide (32.2 g, 188.0 mmol). The reaction mixture (which became quite hot) was stirred for 4 hours and then diluted with water (2500 mL) and extracted with diethyl ether (250 mL). The combined extracts were washed with brine (50 mL) and water (50 mL), dried over MgSO$_4$, concentrated to dryness and flash chromatography to afford 39.0 g of intermediate. The intermediate was dissolved in hours. The mixture was evaporated to dryness and dissolved in dichloromethane (600 mL). The resulting mixture was extracted with perfluorohexane (200 mL, 3 times). The combined extraction was washed with dichloromethane (50 mL) and concentrated to give compound 4 as a clear oil (90.5 g, 81%). $^1$H NMR (400 MHz, CDCl$_3$) δ 3.45 (s, 2H), 4.08 (s, 6H), 4.47 (s, 2H), 7.25-7.35 (m, 5H); $^{19}$F NMR (376 MHz, CDCl$_3$) δ−73.49 (s); $^{13}$C NMR (100.7 Hz, CDCl$_3$) δ 46.43, 65.49, 65.62, 73.94, 79.70 (q, J=29.9 Hz), 120.33 (q, J=292.5 Hz), 127.99, 128.11, 128.57, 137.34; MS (CI) m/z 881 (M$^+$+ 1, 31), 880 (M$^+$, 11), 803 (26), 91 (100); HRMS (CI) Calcd for C$_{24}$H$_{15}$F$_{27}$O$_4$: 880.0539, Found: 880.0515.

c. Synthesis of Compound 5

To a stirred mixture of compound 4 (90.4 g, 102.7 mmol) and anisole (44.4 g, 410.9 mmol) in dichloromethane (500 mL) at 0° C. was slowly added powdered aluminum chloride anhydrous (41.1 g, 308.1 mmol). After the addition, the reaction mixture was allowed to warm to room temperature and stirred for additional 30 minutes. The reaction mixture was quenched by slowly addition of 1N HCl (100 mL) and the resulted mixture was extracted with perfluorohexane (200 mL, 3 times). The combined extraction was washed with dichloromethane (50 mL) and concentrated to give compound 5 as a clear oil (80.3 g, 99%). $^1$H NMR (400 MHz, Acetone-d6) δ 3.73 (d, J=4.0 Hz, 2H), 4.27 (s, 6H), 4.44 (t, J=4.0 Hz, 1H); $^{19}$F NMR (376 MHz, Acetone-d6) δ−71.20 (s); $^{13}$C NMR (100.7 MHz, Acetone-d6) δ 52.05, 62.84, 71.65, 84.75 (q, J=29.9 Hz), 122.77 (q, J=291.8 Hz); MS (CI) m/z 791 (M$^+$+1, 8), 91 (100); HRMS (CI) Calcd for $C_{17}H_{10}F_{27}O_4$: 791.0149, Found: 791.0131.

d. Synthesis of Compound 7

To a stirred mixture of tetraethylene glycol 6 (66.0 g, 340 mmol), imidazole (33.9 g, 498 mmol) and 4-dimethylaminopyridine (5 g, 41 mmol) in dichloromethane (1000 mL) and dimethylformamide (100 mL) at 0° C. was slowly added a solution of tert-Butylchlorodimethylsilane (25.1 g, 166 mmol) in dichloromethane (100 mL) over 4 hours. The resulted mixture was stirred overnight. The reaction mixture was quenched with 1N HCl (300 mL), extracted with ethyl acetate. The combined organic phase was dried over magnesium sulfate, concentrated to dryness, and purified by flash chromatography to afford compound 7 (44.5 g, 87%) as clear oil. $^1$H NMR (400 MHz, CDCl$_3$) δ 0.00 (s, 6H), 0.83 (s, 9H), 1.79 (s, 1H), 3.45-3.70 (m, 16H).

e. Synthesis of Compound 8

To a stirred mixture of 7 (44.5 g, 145 mmol) and triethylamine (58.4 g, 578 mmol) in dichloromethane (700 mL) at 0° C. was added methanesulfonyl chloride (33.1 g, 289 mmol). After the addition, the reaction mixture was stirred overnight at room temperature. The reaction mixture was quenched with 1N HCl (300 mL), extracted with ethyl acetate. The combined organic phase was dried over magnesium sulfate, concentrated to dryness and flash chromatography to afford compound 8 (55.3 g, 99%) as clear oil. $^1$H NMR (400 MHz, CDCl$_3$) δ 0.00 (s, 6H), 0.83 (s, 9H), 3.01 (s, 3H), 3.48 (t, J=5.2 Hz, 2H), 3.55-3.61 (m, 8H), 3.68-3.71 (m, 4H), 4.29-4.32 (m, 2H).

f. Synthesis of Compound 39

To a stirred mixture of 5 (23 g, 29 mmol) in tetrahydrofuran (150 mL) at 0° C. was treated with potassium hydride (7.0 g, 25% on mineral oil, 44 mmol) and the resulting mixture was stirred for additional 1 hour at room temperature. A solution of compound 7 (17.0 g, 44 mmol) in tetrahydrofuran (20 mL) was then added and the resulting mixture was stirred overnight. The reaction mixture was quenched with 1N HCl (100 mL), extracted with ethyl acetate. The combined organic phase was dried over magnesium sulfate, concentrated to dryness and flash chromatography to afford compound 39 (17.2 g, 61%) as clear oil. $^1$H NMR (400 MHz, CDCl$_3$) δ 0.00 (s, 6H), 0.833 (s, 9H), 3.41 (s, 2H), 3.49-3.60 (m, 14H), 3.71 (t, J=5.6 Hz, 2H), 4.01 (s, 6H); $^{19}$F NMR (376 MHz, CDCl$_3$) δ−73.19 (s); $^{13}$C NMR (100.7 Hz, CDCl$_3$) δ−5.58, 0.37, 18.25, 25.71, 46.23, 62.72, 65.52, 66.37, 70.30, 70.62, 70.70, 70.75, 70.79, 72.69, 79.52 (q, J=30.0 Hz), 120.17 (q, J=292.5 Hz);

g. Synthesis of Compound 10

To a stirred mixture of 39 (17.2 g, 15.9 mmol) in tetrahydrofuran (100 mL) at 0° C. was treated with tetrabutylammonium fluoride (20 mL, 1N solution in THF, 20 mmol) and resulting mixture was stirred for additional 2 hour at room temperature. The reaction mixture was concentrated to dryness and flash chromatography to afford compound 10 (12.8 g, 83%) as clear oil. $^1$H NMR (400 MHz, CDCl$_3$) δ 3.39 (s, 2H), 3.53-3.60 (m, 16H), 3.99 (s, 6H); $^{19}$F NMR (376 MHz, CDCl$_3$) δ−73.49 (s); $^{13}$C NMR (100.7 Hz, CDCl$_3$) δ 46.22, 58.78, 61.69, 65.55, 66.41, 70.30, 70.32, 70.54, 70.65, 70.76, 72.49, 79.51 (q, J=36.7 Hz), 120.16 (q, J=292.6 Hz), MS (CD) m/z 967 (M$^+$+1, 100); HRMS (CI) Calcd for $C_{25}H_{26}F_{27}O_8$: 967.1150, Found: 967.1173.

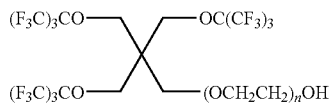

When n is 1, 2, 3, 5, 6, 7, 8, the compounds can also be synthesized by the same procedure as compound 10. When n is larger than 8, the PEG is in a form of a mixture. Fluorinated Surfactant with such PEG group can also be synthesized with the same procedure as outlined for compound 10.

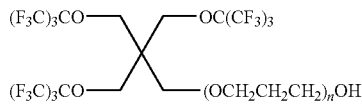

Such compound can also be synthesized with the same procedure as outlined for compound 10.

2. Synthesis of Surfactant with —NR$_2$ Ending Group

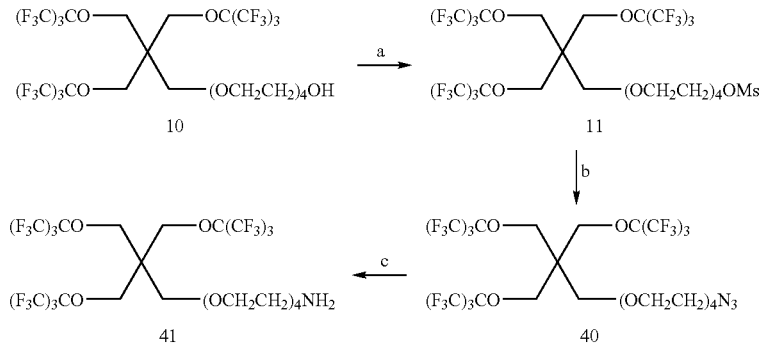

a. Synthesis of Compound 11

To a stirred mixture of 10 (15.5 g, 16 mmol) and triethylamine (6.5 g, 64 mmol) in dichloromethane (100 mL) at 0° C. was added methanesulfonyl chloride (3.64 g, 32 mmol). After the addition, the reaction mixture was stirred overnight at room temperature. The reaction mixture was quenched with 1N HCl (100 mL), extracted with ethyl acetate. The combined organic phase was dried over magnesium sulfate, concentrated to dryness and flash chromatography to afford compound 11 (15.8 g, 95%) as clear oil. $^1$H NMR (400 MHz, CDCl$_3$) δ 3.04 (s, 3H), 3.43 (s, 2H), 3.53-3.58 (m, 8H), 3.61-3.67 (m, 4H), 3.73-3.76 (m, 2H), 4.04 (s, 6H), 4.35-4.37 (m, 2H); $^{19}$F NMR (376 MHz, CDCl$_3$) δ −73.37 (s); $^{13}$C NMR (100.7 Hz, CDCl$_3$) δ 37.54, 46.18, 63.53, 65.45, 66.31, 68.99, 69.09, 69.22, 70.23, 70.52, 70.58, 70.72, 79.46 (q, J=30.7 Hz), 120.11 (q, f=294.1 Hz); MS (Maldi) m/z 1067 (M+Na$^+$, 100); HRMS (Maldi) Calcd for C$_{26}$H$_{27}$F$_{27}$O$_{10}$SNa: 1067.0792, Found: 1067.0755.

b. Synthesis of Compound 40

A mixture of compound 11 (15.8 g, 15.2 mmol) and sodium azide (2.0 g, 30.4 mmol) in dimethylformamide (100 mL) was stirred at 60° C. for 6 hour. Removal of solvent, the residue was purified by flash column chromatography on silica gel to give compound 40 as a liquid (13.1 g, 87%).

c. Synthesis of Compound 41

A mixture of palladium on carbon (400 mg) in methanol (20 μL) was degassed for 1 minute and stirred under an atmosphere of hydrogen for 30 minute. The compound 40 (1.92 g, 1.94 mmol) in methanol (5 mL) was added to the mixture and the resulting mixture was stirred under hydrogen atmosphere overnight. After filtration, the mixture was concentrated under vacuum and purified by flash column chromatography on silica gel to compound 41 as a liquid (1.17 g, 63%).

3. Synthesis of Surfactant with a —SH Ending Group

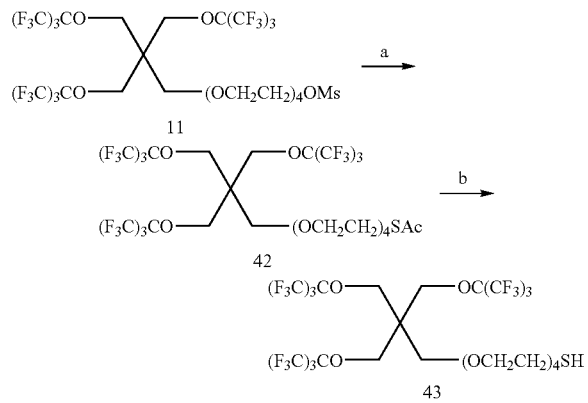

a. Synthesis of Compound 42

Potassium thioacetate (1.71 g, 15 mmol) was added to a stirred mixture of compound 11 (6.76 g, 7 mmol) in dimethylformamide (50 mL). The resulting mixture was stirred at 50° C. overnight. After removal of solvent under vacuum, the residue was purified by flash column chromatography on silica gel to give compound 42 as a liquid (5.91 g, 83%).

b. Synthesis of Compound 43

To a stirred mixture of compound 42 (4.7 g, 4.6 mmol) in methanol (20 mL) was added 1N sodium hydroxide (15 mL) and the resulting mixture was stirred at room temperature for 5 hours. Then 2N hydrochloric acid (8 mL) was added. After removal of solvent, the residue was purified by flash column chromatography on silica gel to give compound 43 as a liquid (4.18 g, 93%).

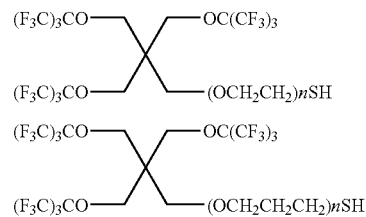

Such compound can also been synthesized with the same procedure as outlined for compound 43.

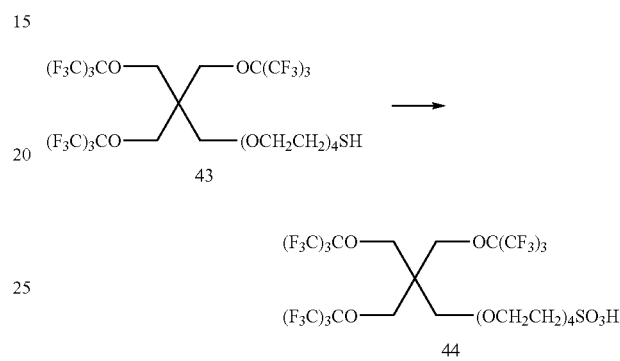

4. Synthesis of Surfactant with a —COOH Ending Group

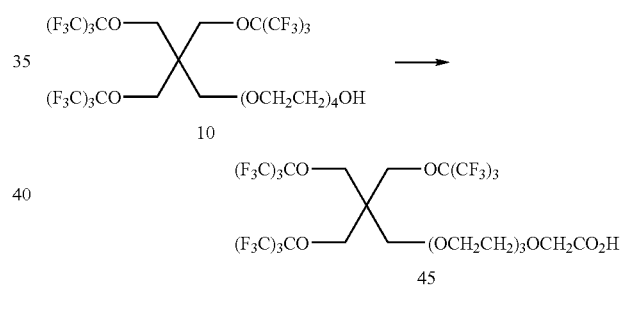

To a stirred mixture of compound 10 (3.87 g, 4 mmol) in acetone at 0° C. was added dropwise a solution of Jones Reagent (3N, 12 mL). After the addition, the mixture was stirred at room temperature for additional 2 hours. Removal solvent under reduced pressure, the residue was purified by flash column chromatography on silica gel to give compound 45 as a viscous oil (3.30 g, 84%).

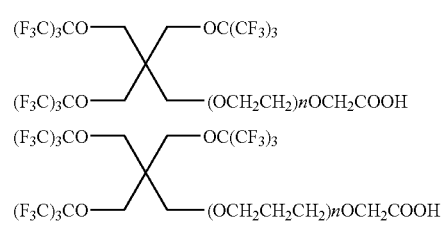

Such compound can also be synthesized with the same procedure as outlined for compound 45.

5. Synthesis of Surfactant with a Chelator Ending Group

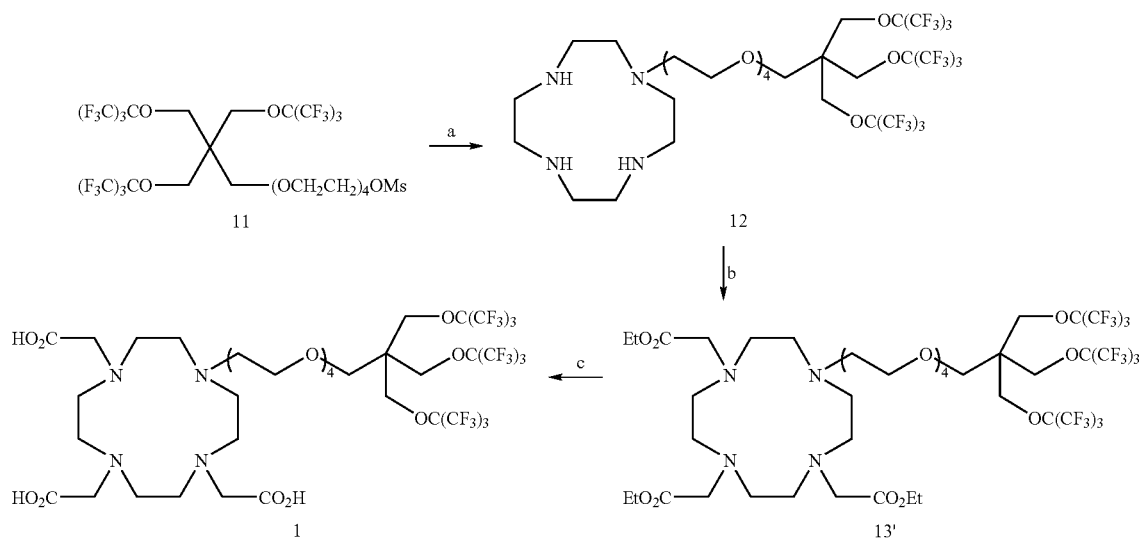

a. Synthesis of Compound 12

To a stirred solution of compound 11 (10.3 g, 9.8 mmol) in dimethylformamide (100 mL) was added cyclen (3.48 g, 20 mmol) in one portion. Then the mixture was stirred at 60° C. overnight. After removal of solvent under vacuum, the residue was purified by flash column chromatography on basic aluminum oxide to compound 12 as viscous oil (10.2 g, 93%).

b. Synthesis of Compound 50

To a stirred solution of compound 12 (9.8 g, 8.8 mmol) in tetrahydrofuran (50 mL) and dimethylformamide (80 mL) was added anhydrous potassium carbonate (9.66 g, 70 mmol) and ethyl bromoacete (7.3 g, 43.8 mmol). The resulting mixture was stirred overnight at 60° C. Then the mixture was washed with brine (200 mL), the aqueous layer was extracted with ethyl acetate (100 mL, 4 times). The combined layers were dried over magnesium sulfate, concentrated under vacuum. The residue was purified by flash column chromatography on silica gel to give the compound 50 as viscous oil (9.95 g, 82%).

c. Synthesis of Compound 1

Lithium hydroxide (622 mg, 28 mmol) was added to a solution of compound 13 (5.52 g, 4 mmol) in tetrahydrofuran (100 mL), methanol (100 mL) and water (100 mL). The resulting mixture was stirred at room temperature for 8 hours. Then 1N hydrochloride acid was added to adjust the solution to pH 3. Removal of solvent under vacuum, the residue was purified by flash column chromatography on aluminum oxide to give compound 1 as a solid (5.0 g, 97%).

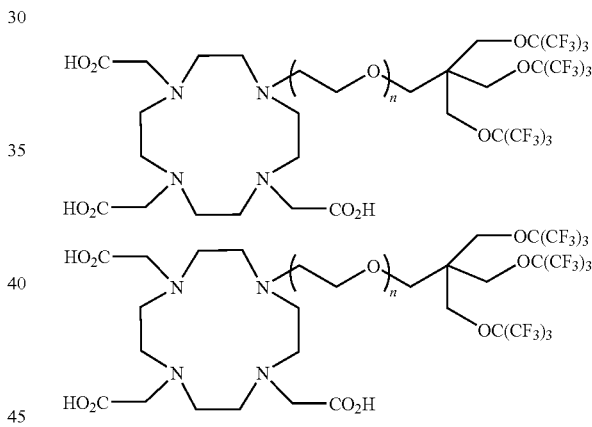

When n is other than 4, such as 0, 1, 2, 3, 8, such surfactants can also be synthesized in the same way as for 1.

6. Synthesis of Surfactant with a Peptide as an Ending Group:

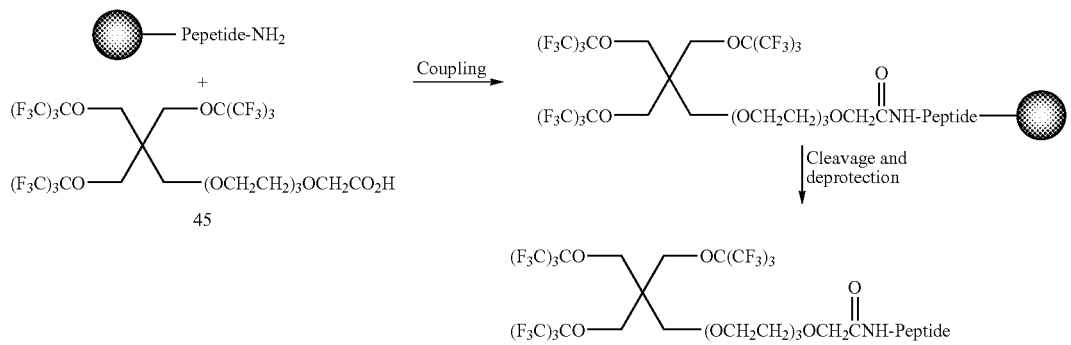

The fluorinated surfactant 45 was incorporated into peptide during the solid phase peptide synthesis as a terminal amino acid by employ the routing coupling, cleavage and deprotection procedure.

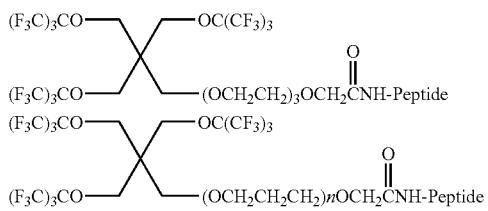

Such compounds can also be synthesized as outlined above.

7. Synthesis of Surfactant with a Nitrogen Atom as Branch Point in a Hydrophobic Moiety

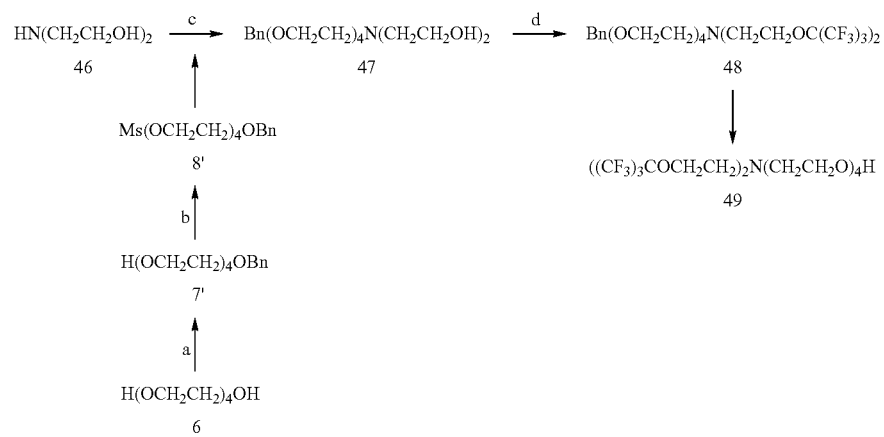

a. Synthesis of Compound 7'

An 60% dispersion of Sodium hydride (20.8 g, 0.52 mol) in paraffin was washed twice with tert-butyl methyl ether and decanted; the sodium hydride was suspended in tetrahydrofuran (300 mL), and then a mixture of tetraethylene glycol 6 (97 g, 0.5 mol) and tetrahydrofuran (50 mL) was added dropwise. After the evolution of hydrogen had stopped, benzyl bromide (51.2 g, 0.3 mol) was added and the reaction mixture stirred for 2 h. Water was added, the organic layer separated, and the aqueous phase extracted with tert-butyl methyl ether. The combined organic phases were dried and the solvents removed under reduced pressure. The crude product 7' (76.5 g, 90%) was used in the next step without further purification.

b. Synthesis of Compound 8'

To a stirred mixture of 7' (45.1 g, 159 mmol) and triethylamine (62.2 g, 636 mmol) in dichloromethane (800 mL) at 0° C. was added methanesulfonyl chloride (36.4 g, 318 mmol). After the addition, the reaction mixture was stirred overnight at room temperature. The reaction mixture was quenched with 1N HCl (300 mL), extracted with ethyl acetate. The combined organic phase was dried over magnesium sulfate, concentrated to dryness and flash chromatography to afford compound 8' (56.2 g, 98%) as clear oil.

c. Synthesis of Compound 47

To a mixture of compound 8' (36.2 g, 100 mmol) in chloroform (800 mL) was added commercial available 46 (52.5 g, 500 mmol) and the resulting mixture was stirred at 40° C. overnight. Then removal solvent under vacuum, the residue was purified by flash column chromatography on silica gel to give compound 48 as a liquid (19.7 g, 53%).

d. Synthesis of Compound 48

To a mixture of compound 47 (18.6 g, 50 mmol), triphenylphosphine (39.5 g, 150 mmol) and 4 Å molecular sieve (15.0 g) in tetrahydrofuran (200 mL) at 0° C. was added dropwise diethylazodicarboxylate (26.1 g, 150 mmol). After the addition, the reaction mixture was allowed to warm to room temperature and stirred for additional 20 minutes. Then perfluoro-tert-butanol (35.4 g, 150 mmol) was added in one portion and the resulting mixture was stirred at 45° C. for 30 hours. The mixture was evaporated to dryness and purified by flash column chromatography on silica gel to give compound 48 as a clear oil (24.6 g, 61%).

e. Synthesis of Compound 49

A mixture of compound 48 (12.1 g, 15 mmol) and palladium on carbon (1.2 g) in methanol (80 mL) was degassed for 1 minute. Then the mixture was stirred under an atmosphere of hydrogen for 12 hours. After filtration, the filtrate was concentrated under vacuum and the residue was purified by flash column chromatography on silica gel to give compound 49 as clear oil (10.2 g, 95%).

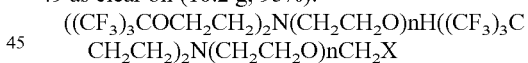

8. Synthesis of Fluorinated Dendrons a. Alcohol 7'

To a stirred solution of tetraethylene glycol 6 (97.0 g, 500.0 mmol) in tetrahydrofuran (450 mL) at 0° C. was added sodium hydride (60% in paraffin, 20.8 g, 520.0 mmol) slowly and the resulted mixture was stirred at rt. for 30 min. Then benzyl bromide (51.2 g, 300.0 mmol) was added and the resulted mixture was stirred at rt. overnight. After quenched the reaction with water (200 mL), the mixture was extracted with ethyl acetate (100 mL, 4 times). The combined organic phase was dried over anhydrous magnesium sulfate. After concentration under vacuum, the residue was purified by flash chromatography on silica gel (n-hexane/ethyl acetate=1/1) to give alcohol 7' as clear oil (76.5 g, 90%). $^1$H NMR (400 MHz, CDCl$_3$) δ 1.28-7.29 (m, 5H), 4.51 (s, 2H), 3.52-3.66 (m, 16H).

b. Methanesulfonate 8'

To a stirred solution of alcohol 7' (69.3 g, 243.7 mmol) and triethylamine (49.2 g, 68.4 mL, 487.0 mmol) in CH$_2$Cl$_2$ (700 mL) at 0° C. was added methanesulfonyl chloride (41.9 g, 28.3 mL, 365.6 mmol). The resulted mixture was stirred at rt.

overnight and quenched with water (400 mL). Organic phase was collected and the aqueous phase was extracted with ethyl acetate. The combined organic phase was washed with 2N HCl (100 mL), brine (100 mL) and dried over anhydrous magnesium sulfate. Concentrated the solution under vacuum gave the methanesulfonate 8' as clear oil (86.6 g, 98%). $^1$H NMR (400 MHz, CD$_3$Cl$_3$) δ 7.25-7.32 (m, 5H), 4.54 (s, 2H), 4.32-4.34 (m, 2H), 3.71-3.73 (m, 2H), 3.59-3.66 (m, 12H), 3.03 (s, 3H).

c. Azide 23

The suspension of methanesulfonate 8' (69.3 g, 191.2 mmol) and sodium azide (16.2 g, 254.6 mmol) in dimethylformamide (800 mL) was stirred at 110° C. overnight. After removal of the solvent under vacuum, the residue was purified by plash chromatography on silica gel ((n-hexane/ethyl acetate=2/1)) to give the azide 23 as clear oil (56.8 g, 96% yield). $^1$H NMR (400 MHz, CD$_3$OD) δ 7.20-7.27 (m, 5H), 4.49 (s, 2H), 3.55-3.61 (m, 14H), 3.29 (t, J=5.0 Hz, 2H).

d. Amine 24

To a stirred solution of azide 23 (55.2 g, 178.4 mmol) in dry tetrahydrofuran (700 mL) at 0° C. was added triphenyl phosphine (59.7, 227.7 mmol) and the resulted mixture was stirred at rt. for 10 h. Water (5.8 mL, 323.4 mmol) then added to hydrolysis the intermediate phosphorous adduct. After 10 h, the reaction mixture was diluted with water (1000 mL) and washed with toluene (200 mL, twice). Evaporation of the aqueous phase yielded the product (50.6 g, 91% yield). $^1$H NMR (400 MHz, CD$_3$OD) δ 7.21-7.29 (m, 5H), 4.51 (s, 2H), 3.55-3.64 (m, 12H), 3.43 (t, J=5.2 Hz, 2H), 2.78 (t, J=5.2 Hz, 2H).

e. Tert-Butyl Ester 13

A suspension of potassium hydride (30%, 3.2 g, 24.0 mmol) was added slowly to a stirred solution of alcohol 5 (15.8 g, 20.0 mmol) in tetrahydrofuran (200 mL) at 0° C. After 10 min, tert-butyl bromoacetate (5.9 mL, 7.8 g, 40.0 mmol) was added to the suspension in one portion at rt and the resulted mixture was stirred at rt overnight. After quenched the reaction with water (20 mL), the mixture was transferred into separatory funnel and the lower phase was collected as clear oil. Removal of low boiling point impurities under vacuum gave the ester 13 as clear oil (14.1 g, 78% yield). $^1$H NMR (400 MHz, CD$_3$Cl$_3$) δ 4.14 (s, 6H), 3.91 (s, 2H), 3.57 (s, 2H), 1.46 (s, 9H); $^{19}$F NMR (376 MHz, CD$_3$Cl$_3$) δ-73.51 (s); $^{13}$C NMR (100.7 MHz, CD$_3$Cl$_3$) δ 168.5, 120.2 (q, J=293.4 Hz), 81.8, 79.3-80.0 (m), 69.2, 67.2, 66.2, 46.1, 27.9; MS (MALDI-TOF) m/z 905 (M$^+$+1, 100); HRMS (MALDI-TOF) calcd for C$_{23}$H$_{20}$F$_{27}$O$_6$ 905.0829, found 905.0823.

f. Acid 14

The compound was prepared as shown in Schemes 3-9 using procedures analogous to those disclosed for lower analogues. $^1$H NMR (400 MHz, Acetone-d6) δ 4.29 (s, 6H), 4.14 (s, 2H), 3.73 (s, 2H); $^{19}$F NMR (376 MHz, Acetone-d6) δ-71.24 (s); $^{13}$C NMR (100.7 MHz, Acetone-d6) δ 170.9, 121.2 (q, J=292.5 Hz), 80.1-81.0 (m), 68.6, 67.5, 67.1, 47.1; MS (MALDI-TOF) m/z 849 (M$^+$+1, 100); HRMS (MALDI-TOF) calcd for C$_{19}$H$_{12}$F$_{27}$O$_6$ 849.0203, found 849.0197.

g. Amide 25

The compound was prepared as shown in Schemes 3-9 using procedures analogous to those disclosed for lower analogues. $^1$H NMR (400 MHz, CD$_3$OD) δ 7.20-7.33 (m, 5H), 4.53 (s, 2H), 4.19 (s, 6H), 3.92 (s, 2H), 3.54-3.66 (m, 12H), 3.52-3.54 (m, 4H), 3.42 (t, J=5.6 Hz, 2H); $^{19}$F NMR (376 MHz, CD$_3$OD) δ-71.13 (s); $^{13}$C NMR (100.7 m/z, CD$_3$OD) δ 168.1, 138.2, 128.2, 127.6, 127.5, 120.0 (q, J=293.3 Hz), 79.2-79.9 (m), 73.1, 71.1, 70.54, 70.5, 70.4, 70.3, 70.2, 69.6, 69.3, 66.7, 65.0, 46.1, 38.6; MS (MALDI-TOF) m/z 1136 (M$^+$+1, 100); HRMS (MALDI-TOF) calcd for C$_{34}$H$_{34}$F$_{27}$NNaO$_9$ 1136.1700, found 1136.1669.

h. Surfactant 26

The compound was prepared as shown in Schemes 3-9 using procedures analogous to those disclosed for lower analogues. $^1$H NMR (400 MHz, CD$_3$Cl$_3$) δ 4.03 (s, 6H), 3.89 (s, 2H), 3.54-3.64 (m, 12H), 3.43-3.54 (m, 6H); $^{19}$F NMR (376 MHz, CD$_3$Cl$_3$) δ-73.44 (s); $^{13}$C NMR (100.7 MHz, CD$_3$Cl$_3$) δ 168.4, 120.0 (q, J=293.3 Hz), 79.4-79.9 (m), 72.4, 71.0, 70.4, 70.2, 70.1, 70.08, 66.5, 64.9, 61.5, 46.2, 38.7; MS (MALDI-TOF) m/z 1046 (M$^+$+Na), 1024 (M$^+$+1, 100); HRMS (MALDI-TOF) calcd for C$_{27}$H$_{28}$F$_{27}$NNaO$_9$ 1046.1231, found 1046.1220.

i. Di-Tert-Butyl Ester 15

The compound was prepared as shown in Schemes 3-9 using procedures analogous to those disclosed for lower analogues. $^1$H NMR (400 MHz, CD$_3$Cl$_3$) δ 4.12 (s, 6H), 4.10 (s, 2H), 4.02 (s, 2H), 3.92 (s, 2H), 3.59 (s, 2H), 1.44 (s, 9H), 1.42 (s, 9H); $^{19}$F NMR (376 MHz, CD$_3$Cl$_3$) δ-73.29 (s); $^{13}$C NMR (100.7 MHz, CD$_3$Cl$_3$) δ 168.7, 167.9, 167.7, 120.1 (q, J=293.4 Hz), 82.8, 82.0, 69.9-79.8 (m), 69.5, 67.7, 66.5, 49.9, 48.6, 46.0, 27.8, 27.76; MS (MALDI-TOF) m/z 1098 (M$^+$+Na); HRMS (MALDI-TOF) calcd for C$_{31}$H$_{32}$F$_{27}$NNaO$_9$ 1098.1544, found 1098.1538.

j. Diacid 16

The compound was prepared as shown in Schemes 3-9 using procedures analogous to those disclosed for lower analogues. $^1$H NMR (400 MHz, CD$_3$OD) δ 4.22 (s, 8H), 4.16 (s, 2H), 4.14 (s, 2H), 3.60 (s, 2H); $^{19}$F NMR (376 MHz, CD$_3$OD) δ-71.18 (s); $^{13}$C NMR (100.7 m/z, CD$_3$OD) δ 172.5, 172.1, 171.7, 121.6 (q, J=293-4 Hz), 80.4-81.5 (m), 70.3, 68.6, 67.9, 50.0, 47.4; MS (MALDI-TOF) m/z 986 (M$^+$+Na), 964 (M$^+$+1); HRMS (MALDI-TOF) calcd for C$_{23}$H$_{17}$F$_{27}$NO$_9$ 964.0472, found 964.0476.

k. Diamide 27

The compound was prepared as shown in Schemes 3-9 using procedures analogous to those disclosed for lower analogues. $^1$H NMR (400 MHz, CDCl$_3$) δ 7.27-7.34 (m, 10H), 4.56 (s, 2H), 4.54 (s, 2H), 4.11 (s, 6H), 4.03 (s, 2H), 3.86 (s, 2H), 3.84 (s, 2H), 3.60-3.69 (m, 24H), 3.54-3.58 (m, 6H), 3.40-3.48 (m, 4H); $^{19}$F NMR (376 MHz, CDCl$_3$) δ-73.49 (s); $^{13}$C NMR (100.7 MHz, CDCl$_3$) δ 169.2, 169.1, 168.4, 138.1, 138.0, 128.33, 128.3, 127.74, 127.7, 127.67, 127.6, 120.0 (q, J=292.5 Hz), 79.0-79.7 (m), 77.2, 73.2, 73.16, 70.5, 70.46, 70.4, 70.27, 70.17, 70.08, 69.4, 69.35, 69.3, 69.0, 68.9, 67.5, 66.1, 60.3, 53.1, 53.0, 46.0, 39.6, 39.2, 20.9, 14.1; MS (MALDI-TOF) m/z 986 (M$^+$+Na), 1516 (M$^+$+1, 100); HRMS (MALDI-TOF) calcd for C$_{53}$H$_{62}$F$_{27}$N$_3$NaO$_{15}$ 1516.3647, found 1516.3599.

l. Surfactant 28

The compound was prepared as shown in Schemes 3-9 using procedures analogous to those disclosed for lower analogues. $^1$H NMR (400 MHz, CD$_3$OD) δ 4.24 (s, 6H), 4.22 (s, 2H), 4.06 (s, 2H), 4.05 (s, 2H), 3.58-3.67 (m, 22H), 3.54-3.57 (m, 8H), 3.39-3.43 (m, 4H); $^{19}$F NMR (376 MHz, CD$_3$OD) δ-71.17 (s); $^{13}$C NMR (100.7 MHz, CD$_3$OD) δ 172.0, 171.4, 170.8, 121.6 (q, J=292.5 Hz), 80.4-81.4 (m), 73.7, 71.6, 71.4, 71.3, 71.2, 70.4, 70.3, 69.7, 68.7, 68.1, 62.2, 52.4, 47.3, 40.6, 40.4; MS (MALDI-TOF) m/z 1336 (M$^+$+Na, 100); MS (MALDI-TOF) calcd for C$_{39}$H$_{50}$F$_{27}$N$_3$NaO$_{15}$ 1336.2708, found 1336.2703.

m. Tetra-Tert-Butyl Ester 17

The compound was prepared as shown in Schemes 3-9 using procedures analogous to those disclosed for lower analogues. $^1$H NMR (400 MHz, CDCl$_3$) δ 3.80-4.13 (m, 20H), 3.47 (s, 2H), 1.28-1.31 (m, 36H); $^{19}$F NMR (376 MHz, CDCl$_3$) δ-72.94 (s); $^{13}$C NMR (100.7 MHz, CDCl$_3$) δ 169.2, 169.1, 168.2, 167.6, 167.5, 167.45, 167.3, 120.0 (q, J=293.4 Hz), 82.9, 82.6, 81.8, 81.5, 78.7-79.8 (m), 68.3, 67.4, 66.6, 50.4, 50.1, 49.3, 48.9, 47.6, 46.6, 45.8, 27.5, 27.4; MS (MALDI-TOF) m/z 1456 (M$^+$+K); HRMS (MALDI-TOF) calcd for $C_{47}H_{58}F_{27}KN_3O_{15}$ 1456.3074, found 1456.3327.

n. Tetraacid 18

The compound was prepared as shown in Schemes 3-9 using procedures analogous to those disclosed for lower analogues. $^1$H NMR (400 MHz, CD$_3$OD) δ 4.15 (s, 2H), 4.05-4.09 (m, 100H), 3.90-4.01 (m, 6H), 3.53-3.59 (m, 2H), 3.43 (s, 2H); $^{19}$F NMR (376 MHz, CD$_3$OD) δ−71.13 (s); $^{13}$C NMR (100.7 MHz, CD$_3$OD) δ 172.5, 172.4, 172.3, 172.15, 172.0, 171.6, 171.0, 121.6 (q, J=292.6 Hz), 80.4-81.5 (m), 69.7, 69.1, 68.7, 68.2, 67.5, 50.5, 50.3, 49.8, 49.77, 47.3; MS (MALDI-TOF) m/z 1216 (M$^+$+Na); HRMS (MALDI-TOF) calcd for $C_{31}H_{26}F_{27}N_3NaO_{15}$ 1216.0830, found 11216.0820.

o. Tetraamide 29

The compound was prepared as shown in Schemes 3-9 using procedures analogous to those disclosed for lower analogues. $^1$H NMR (400 MHz, CDCl$_3$) δ 7.25-7.34 (m, 20H), 4.55 (s, 8H), 4.07-4.15 (m, 14H), 3.90-3.95 (m, 6H), 3.50-3.68 (m, 48H), 3.37-3.43 (m, 10H); $^{19}$F NMR (376 MHz, CDCl$_3$) δ−73.47 (s); $^{13}$C NMR (100.7 MHz, CDCl$_3$) δ 169.8, 169.7, 169.1, 168.9, 168.7, 168.3, 168.0, 138.0, 128.3, 127.7, 127.6, 120.0 (q, J=293.3 Hz), 79.1-80.3 (m), 73.1, 70.4, 70.3, 70.0, 69.9, 69.8, 69.3, 69.1, 69.0, 68.3, 67.4, 66.4, 52.8, 52.7, 52.5, 48.3, 47.2, 45.8, 39.3, 39.2; MS (MALDI-TOF) m/z 2276 (M$^+$+Na, 100); HRMS (MALDI-TOF) calcd for $C_{91}H_{118}F_{27}N_7NaO_{27}$ 2276.7542, found 2276.7494.

p. Surfactant 30

The compound was prepared as shown in Schemes 3-9 using procedures analogous to those disclosed for lower analogues. $^1$H NMR (400 MHz, CD$_3$OD) δ 4.25 (s, 10H), 4.22 (s, 2H), 4.19 (s, 2H), 4.15 (s, 2H), 4.06 (s, 2H), 4.05 (s, 2H), 3.60-3.60 (m, 42H), 3.54-3.58 (m, 16H), 3.44 (t, J=4.2 Hz, 4H), 3.38 (t, J=5.6 Hz, 4H); $^{19}$F NMR (376 MHz, CDCl$_3$) δ−73.48 (s); $^{13}$C NMR (100.7 MHz, CDCl$_3$) δ 172.2, 171.9, 171.3, 171.2, 171.1, 170.8, 170.5, 121.6 (q, J=292.5 Hz), 80.3-81.5 (m), 73.7, 71.6, 71.4, 71.2, 71.18, 71.1, 70.4, 70.3, 69.5, 68.7, 68.3, 62.2, 53.2, 53.0, 52.5, 49.7, 47.2, 40.5, 40.4; MS (MALDI-TOF) m/z 1916 (M$^+$+Na, 100); HRMS (MALDI-TOF) calcd for $C_{63}H_{94}F_{27}N_7NaO_{27}$ 1916.5664, found 1916.5694.

q. Octa-Tert-Butyl Ester 19

The compound was prepared as shown in Schemes 3-9 using procedures analogous to those disclosed for lower analogues. $^1$H NMR (400 MHz, CD$_3$OD) δ 4.40 (s, 2H), 4.34 (s, 2H), 4.28 (s, 4H), 4.25 (s, 8H), 4.12-4.17 (m, 12H), 4.03-4.07 (m, 8H), 3.59 (s, 2H), 1.45-1.50 (m, 72H); $^{19}$F NMR (376 MHz, CD$_3$OD) δ−71.16 (s); $^{13}$C NMR (100.7 MHz, CD$_3$OD) δ 172.0, 171.6, 171.2, 171.1, 171.0, 170.8, 170.6, 169.7, 169.6, 169.55, 169.43, 169.4, 121.6 (q, J=293.3 Hz), 84.1, 84.0, 83.8, 83.7, 83.1, 83.0, 82.9, 80.3-81.5 (m), 69.5, 68.6, 68.3, 51.6, 51.5, 51.0, 50.8, 50.77, 50.1, 49.9, 49.1, 48.4, 47.2, 28.4, 28.3, 28.29; MS (MALDI-TOF) m/z 2125 (M$^+$+Na); HRMS (MALDI-TOF) calcd for $C_{79}H_{110}F_{27}N_7NaO_{27}$ 2124.6916, found 2124.7023.

r. Surfactant 22

The compound was prepared as shown in Schemes 3-9 using procedures analogous to those disclosed for lower analogues. $^1$H NMR (400 MHz, CD$_3$OD) δ 4.39 (s, 2H), 4.35 (s, 2H), 4.21-4.24 (m, 14H), 4.18 (s, 6H), 4.05-4.10 (m, 10H), 3.54-3.67 (m, 116H), 3.42-3.47 (m, 8H), 3.36-3.40 (m, 8H); $^{19}$F NMR (376 MHz, CD$_3$OD) δ−71.11 (s); $^{13}$C NMR (100.7 MHz, CD$_3$OD) δ 172.1, 171.7, 171.6, 171.59, 171.3, 171.26, 171.1, 171.06, 170.8, 170.7, 170.6, 170.5, 121.5 (q, J=292.6 Hz), 80.2-81.6 (m), 73.6, 71.5, 71.3, 71.2, 71.17, 71.1, 70.35, 70.3, 70.2, 69.4, 68.6, 68.3, 62.2, 53.3, 53.2, 53.1, 53.08, 52.9, 52.7, 50.5, 50.3, 49.5, 49.3, 48.1, 47.2, 40.5, 40.47, 40.4; MS (MALDI-TOF) m/z 3077 (++Na, 100); HRMS (MALDI-TOF) calcd for $C_{111}H_{182}F_{27}N_{15}NaO_{51}$ 3077.1576, found 3077.1570.

9. Synthesis of Highly Fluorinated Chelators a. Triol 3

To a stirred suspension of pentaerythritol 2 (68.0 g, 0.5 mol) in toluene (50.0 mL) at rt. was added triethyl orthoacetate (81.0 g, 92.0 mL, 0.5 mol) and p-toluenesulfonic acid monohydrate (0.3 g). Then ethanol was removed by distillation from the mixture at 80° C. overnight. After all the ethanol had been distilled, the bath temperature was raised to 125° C., and toluene was distilled off until the solution became homogeneous. The residue was purified by column chromatography on neutral aluminum oxide (n-Hexane/Ethyl acetate=1/1) to give the alcohol intermediate as white solid (73.6 g, 92% yield). $^1$H NMR (400 MHz, CDCl$_3$) δ 4.00 (s, 6H), 3.44 (s, 2H), 1.44 (s, 3H). Powdered potassium hydroxide (123.2 g, 2.2 mol) was added to a stirred dimethyl sulfoxide (750 mL), and the resulting mixture was stirred at rt. for 10 min. Then the alcohol intermediate (73.6 g, 460.0 mol) was added, followed quickly by benzyl bromide (94.7 g, 65.9 mL, 554.0 mmol). The reaction mixture was stirred for 2 h, then diluted with water (3000 mL) and extracted with diethyl ether. The combined organic phases were washed with brine and water, dried with magnesium sulfate and concentrated to afford the 4-benzyloxymethyl-1-methyl-2,6,7-trioxa-bicyclo[2.2.2]octane intermediate as a white solid. The intermediate was then dissolved in methanol (300 mL) and treated with 0.1N HCl (600 mL). The resulting mixture was stirred at rt. for 4 h, treated with sodium bicarbonate (42.5 g, 506.0 mmol), stirred for an additional 1 h, and concentrated under vacuum. The residue was purified by flash chromatography on silica gel (CH$_2$Cl$_2$/Methanol=10/1) to give the pure triol 3 as viscous oil (59.3 g, 57% yield). $^1$H NMR (400 MHz, CDCl$_3$) δ 7.26-7.33 (m, 5H), 4.46 (s, 2H), 3.64 (s, 6H), 3.39 (s, 2H).

b. Perfluoro-Tert-Butyl Ether 4

To a stirred suspension of triol 3 (11.30 g, 50.0 mmol), triphenylphosphine (59.0 g, 225.1 mmol), and 4 Å molecular sieves (6.0 g) in tetrahydrofuran (300 mL) at 0° C. was added dropwise diethylazodicarboxylate (39.2 g, 225.1 mmol). After the addition, the reaction mixture was allowed to warm to rt. and stirred for an additional 20 min. Then perfluoro-tert-butanol (53.2 g, 225.1 mmol) was added in one portion, and the resulting mixture was stirred for 30 h at 45° C. in a sealed vessel. Water (30 mL) was added to the reaction mixture and stirred for an additional 10 min. Then the mixture was transferred to a separatory funnel, and the lower phase was collected. Removal of low boiling point impurities under vacuum gave the product 4 as clear oil (35.6 g, 81% yield). $^1$H NMR (400 MHz, CDCl$_3$) δ 7.25-7.35 (m, 5H), 4.47 (s, 2H), 4.08 (s, 6H), 3.45 (s, 2H).

c. Alcohol 5

To a stirred solution of ether 4 (29.3 g, 33.2 mmol) and anisole (14.4 g, 132.9 mmol) in dichloromethane (500 mL) at 0° C. was added aluminum chloride powder (13.3 g, 99.7 mmol) slowly. The resulting mixture was stirred at 0° C. for 1 h, and then water (100 mL) was added slowly. The lower layer was collected as clear oil of alcohol 5 (25.9 g, 99% yield). $^1$H NMR (400 MHz, Acetone-d6) δ 4.27 (s, 6H), 3.74 (s, 2).

d. Trifluoromethanesulfonate 36

To a stirred solution of alcohol 5 (7.9 g, 10.0 mmol) and pyridine (8.2 mL, 7.9 g, 100.0 mmol) in tetrahydrofuran (250 mL) was added dropwise a solution of trifluoromethanesulfonic anhydride (8.2 mL, 14.1 g, 50.0 mmol) in tetrahydrofuran (20 mL) at 0° C. After stirring at this temperature for 1 h, the reaction was quenched by slow addition of water (27 mL). The mixture was transferred to separatory funnel, and the lower phase was collected as clear oil. Washing the oil with dichloromethane gave the pure trifluoromethanesulfonate 36 as clear oil (8.8 g, 96% yield). Preferably, this compound is handled and stored at temperatures below room temperature. $^1$H NMR (400 MHz, Acetone-d6) δ 4.82 (s, 2H), 4.39 (s, 6H); $^{19}$F NMR (376 MHz, Acetone-d6) δ 71.21 (s, 27F), 75.93 (s, 3F).

e. Compound 37

A suspension of trifluoromethanesulfonate 36 (8.5 g, 9.3 mmol) and cyclen (3.3 g, 18.9 mmol) in a mixture of tetrahydrofuran and dimethylformamide (50 mL/50 mL) was stirred at rt. for 2 h. Then the reaction temperature was slowly raised to 60° C., and the mixture was then stirred at this temperature overnight. After concentration of the reaction mixture to dryness, the residue was dissolved in dichloromethane (50 mL), and the solution was extracted with F362 (50 mL, three times). Evaporation of the combined F362 phase gave the product 37 as clear oil (7.7 g, 88% yield). $^1$H NMR (400 MHz, CD$_3$Cl$_3$) δ 4.19 (s, 6H), 2.72-2.75 (m, 6H), 2.58-2.60 (m, 4H), 2.51-2.54 (m, 8H); $^{19}$F NMR (376 MHz, CD$_3$Cl$_3$) δ –73.31 (s); $^{13}$C NMR (100.7 MHz, CD$_3$Cl$_3$) δ 120.1 (q, J=293.3 Hz), 79.1-80.0 (m), 68.4, 54.4, 53.4, 46.9, 46.0, 45.7, 45.5; MS (CI) m/z 945 (M$^+$+1, 100); HRMS (CI) calcd for C$_{25}$H$_{28}$F$_{27}$N$_4$O$_3$ 945.1730, found 945.1717.

f. Compound 38

Powdered potassium carbonate (8.3 g, 60.2 mmol) and ethyl bromoacetate (4.2 mL, 6.3 g, 37.5 mmol) was added to a stirred solution of amine 37 (7.1 g, 7.5 mmol) in a mixture of tetrahydrofuran and dimethylformamide (35 mL/35 mL) at rt. and the resulting suspension was stirred at 60° C. overnight. After filtration, the solvent was removed under vacuum, and the residue was purified by flash chromatography on neutral aluminum oxide (CH$_2$Cl$_2$/Methanol=10/1) to give the product 38 as clear oil (6.3 g, 92% yield). $^1$H NMR (400 MHz, CD$_3$Cl$_3$) δ 4.03-4.10 (m, 12H), 3.34 (s, 2H), 3.25 (s, 4H), 2.62-2.76 (m, 18H), 1.16-1.21 (m, 9H); $^{19}$F NMR (376 MHz, CD$_3$Cl$_3$) δ–73.42 (s); $^{13}$C NMR (100.7 MHz, CD$_3$Cl$_3$) δ 171.7, 171.4, 120.3 (q, J=293.3 Hz), 79.1-80.0 (m), 68.3, 60.2, 56.0, 54.9, 54.8, 54.0, 52.6, 52.2, 51.9, 46.7, 29.8, 14.3, 14.1; MS (MALDI-TOF) m/z 1023 (M$^+$+1, 100); HRMS (MALDI-TOF) calcd for C$_{37}$H$_{46}$F$_{27}$N$_4$O$_9$ 1023.2834, found 1023.2883.

g. Compound 35

To a solution of lithium hydroxide (1.4 g, 60.0 mmol) in water (10 mL) was added a solution of ester 38 (6.1 g, 6.0 mmol) in methanol (200 mL) at rt. The resulted mixture was stirred at rt. overnight. Then 2N HCl was added to adjust the reaction mixture to pH 1. The solid was collected and washed with water and diethyl ether. Solvent was then removed under vacuum to give the product as white solid (5.4 g, 97% yield). $^1$H NMR (400 MHz, CD$_3$OD) δ 4.20 (s, 6H), 3.59 (s, 2H), 3.41 (s, 3H), 3.22 (br, 4H), 3.06 (br, 4H), 2.98 (s, 8H), 2.80 (br, 3H); $^{19}$F NMR (376 MHz, CD$_3$OD) δ–70.93 (s); $^{13}$C NMR (100.7 MHz, CD$_3$OD) δ 180.1, 177.4, 121.6 (q, J=292.5 Hz), 81.0 (m), 69.9, 58.5, 56.8, 52.2, 51.9, 48.9, 45.9, 45.7, 22.2; MS (MALDI-TOF) m/z 1119 (M$^+$+1, 100); HRMS (CI) calcd for C$_{31}$H$_{34}$F$_{27}$N$_4$O$_9$ 1119.1895, found 945.1717.

h. Alcohol 7'

To a stirred solution of tetraethylene glycol 6 (97.0 g, 500.0 mmol) in tetrahydrofuran (450 mL) at 0° C. was added sodium hydride (60% in paraffin, 20.8 g, 520.0 mmol) slowly, and the resulting mixture was stirred at rt. for 30 min. Then benzyl bromide (51.2 g, 300.0 mmol) was added, and the resulting mixture was stirred at rt. overnight. After quenching the reaction with water (200 mL), the mixture was extracted with ethyl acetate (100 mL, 4 times). The combined organic phase was dried over anhydrous magnesium sulfate. After concentration under vacuum, the residue was purified by flash chromatography on silica gel (n-hexane/ethyl acetate=1/1) to give alcohol 7' as clear oil (76.5 g, 90%). $^1$H NMR (400 MHz, CDCl$_3$) δ 7.28-7.29 (m, 5H), 4.51 (s, 2H), 3.52-3.66 (m, 16H).

L. Methanesulfonate 8'

To a stirred solution of alcohol 7' (69.3 g, 243.7 mmol) and triethylamine (49.2 g, 68.4 mL, 487.0 mmol) in CH$_2$Cl$_2$ (700 mL) at 0° C. was added methanesulfonyl chloride (41.9 g, 28.3 mL, 365.6 mmol). The resulting mixture was stirred at rt. overnight and quenched with water (400 mL). The organic phase was collected, and the aqueous phase was extracted with ethyl acetate. The combined organic phase was washed with 2N HCl (100 mL) and brine (100 mL) and then dried over anhydrous magnesium sulfate. Concentration of the solution under vacuum gave the methanesulfonate 8' as clear oil (86.6 g, 98%). $^1$H NMR (400 MHz, CD$_3$Cl$_3$) δ 7.25-7.32 (m, 5H), 4.54 (s, 2H), 4.32-4.34 (m, 2H), 3.71-3.73 (m, 2H), 3.59-3.66 (m, 12H), 3.03 (s, 3H).

j. Compound 9

A solution of alcohol 5 (5.9 g, 7.5 mmol) in tetrahydrofuran (50 mL) was stirred at 0° C., and potassium hydride (25%, 1.4 g, 8.5 mmol) was added slowly to the solution. After the addition, the mixture was stirred for additional 10 min at 0° C. and methanesulfonate 8' (4.2 g, 7.5 mmol) was then added in one portion. The resulting mixture was stirred at rt. overnight and quenched with water (100 mL). The organic phase was collected, and the aqueous phase was extracted with ethyl acetate. The combined organic phase was washed with 2N HCl (100 mL) and brine (100 mL) and then dried over anhydrous magnesium sulfate. Concentration under vacuum and flash chromatography on silica gel (n-hexane/ethyl acetate=10/1) gave compound 9 as clear oil (6.4 g, 80%). $^1$H NMR (400 MHz, CD$_3$Cl$_3$) δ 7.26-7.33 (m, 5H), 4.56 (s, 2H), 4.07 (s, 6H), 3.54-3.69 (m, 16H), 3.45 (s, 2H); $^{19}$F NMR (376 MHz, CD$_3$Cl$_3$) δ–73.28 (s); $^{13}$C NMR (100.7 MHz, CD$_3$Cl$_3$) δ 138.3, 128.3, 127.7, 127.5, 120.1 (q, J=292.6 Hz), 78.9-79.8 (m), 73.2, 70.7, 70.65, 70.6, 70.56, 70.3, 69.4, 66.3, 65.5, 46.2; MS (MALDI-TOF) m/z 1079 (M$^+$+Na, 100); HRMS (MALDI-TOF) calcd for C$_{32}$H$_{31}$F$_{27}$NaO$_8$ 1079.1458, found 1079.1517.

k. Alcohol 10

A suspension of compound 9 (6.0 g, 5.7 mmol) and palladium hydroxide (10%, 1.2 g) in methanol (80 mL) was stirred under an atmosphere of hydrogen for 2 h. After filtration, the mixture was concentrated under vacuum and purified by flash chromatography on silica gel (n-hexane/ethyl acetate=8/1) to give alcohol 10 as clear oil (5.3 g, 97%). $^1$H NMR (400 MHz, CDCl$_3$) δ 3.99 (s, 6H), 3.53-3.60 (m, 16H), 3.39 (s, 2H).

1. Methanesulfonate 11

To a stirred solution of alcohol 10 (5.1 g, 5.3 mmol) and triethylamine (3.2 g, 31.8 mmol) in CH$_2$Cl$_2$ (80 mL) at 0° C. was added methanesulfonyl chloride (1.9 g, 15.9 mmol). The resulting mixture was stirred at rt. and quenched with water (50 mL). The organic phase was collected, and the aqueous phase was extracted with ethyl acetate. The combined organic solvent was dried over anhydrous magnesium sulfate. After concentration under vacuum, the residue was purified by flash chromatography on silica gel (n-hexane/ethyl acetate=10/1) to give methanesulfonate 11 as clear oil (5.5 g, 99%). $^1$H NMR (400 MHz, CD$_3$Cl$_3$) δ 4.35 (m, 2H), 4.04 (s, 6H), 3.73-3.76 (m, 2H), 3.53-3.67 (m, 12H), 3.43 (s, 2H), 3.04 (s, 3H).

m. Compound 12

A suspension of methanesulfonate 11 (5.3 g, 5.1 mmol) and cyclen (1.8 g, 10.2 mmol) in a mixture of dimethylformamide and tetrahydrofuran (50 mL) was stirred at 60° C. overnight. After concentrating the reaction mixture to dryness, the residue was purified by solid phase extraction on fluorous silica gel to give the product 12 as clear oil (5.2 g, 93% yield). $^1$H NMR (400 MHz, CD$_3$OD) δ 4.14 (s, 6H), 3.57-3.69 (m, 14H), 3.49 (s, 2H), 2.95-3.04 (m, 7H), 2.85-2.89 (m, 5H), 2.76-2.82 (m, 2H), 2.69 (s, 4H); $^{19}$F NMR (376 MHz, CD$_3$OD) δ−71.14 (s); $^{13}$C NMR (100.7 MHz, CD$_3$OD) δ 121.6 (q, J=292.5 Hz), 80.5-81.4 (m), 78.3, 72.0, 71.9, 71.73, 71.7, 71.67, 71.6, 71.56, 71.5, 71.4, 71.41, 71.4, 71.2, 69.6, 67.5, 67.2, 50.9, 46.4, 44.4; MS (MALDI-TOF) m/z 1121 (M$^+$+1, 100); HRMS (MALDI-TOF) calcd for C$_{33}$H$_{44}$F$_{27}$N$_7$O$_4$ 1021.2779, found 1021.2790.

n. Tri-Ethyl Ester 50

To a stirred solution of compound 12 (5.1 g, 4.6 mmol) in tetrahydrofuran (25 mL) and dimethylformamide (25 mL) was added powdered anhydrous potassium carbonate (6.3 g, 46.0 mmol) and ethyl bromoacetate (2.6 mL, 3.8 g, 23.0 mmol). The resulting mixture was stirred overnight at 60° C. After filtration, the solvent was removed under vacuum, and the residue was purified by flash chromatography on neutral aluminum oxide (CH$_2$Cl$_2$/Methanol=10/1) to give the product 50 as clear oil (5.2 g, 82% yield). $^1$H NMR (400 MHz, CD$_3$OD) δ 4.16-4.29 (m, 8H), 4.14 (s, 6H), 3.56-3.67 (m, 16H), 3.48 (s, 4H), 2.70-3.45 (m, 4H) 2.41-2.76 (m, 14H), 1.27-1.30 (m, 9H); $^{19}$F NMR (376 MHz, CD$_3$OD) δ−71.12 (s); $^{13}$C NMR (100.7 MHz, CD$_3$OD) δ 175.3, 175.1, 121.6 (q, J=292.6 Hz), 80.7-81.5 (m), 71.9, 71.5, 71.4, 71.3, 71.2, 70.8, 68.5, 67.4, 67.1, 62.3, 62.26, 56.4, 56.1, 53.6, 51.9, 51.1, 48.4, 47.4, 14.5, 14.3; MS (MALDI-TOF) m/z 1379 (M+1, 100); HRMS (MALDI-TOF) calcd for C$_{45}$H$_{62}$F$_{27}$N$_4$O$_{13}$ 1379.3882, found 1379.3902.

o. Compound 1

Lithium hydroxide (0.9 g, 37.0 mmol) was added to a solution of compound 9 (5.1 g, 3.7 mmol) in methanol (100 mL) and water (10 mL). The resulting mixture was stirred at rt. for 8 h. Then 1N HCl was added to adjust the solution to pH 1. After removal of solvent under vacuum, the residue was purified by flash column chromatography on neutral aluminum oxide to give compound 1 as white solid (4.7 g, 990%). $^1$H NMR (400 MHz, Acetone-d6) δ 4.20 (s, 6H), 3.53-3.59 (m, 16H), 2.2-3.2 (m, 24H); $^{19}$F NMR (376 MHz, CD$_3$OD) δ−71.15 (s); $^{13}$C NMR (100.7 MHz, CD$_3$OD) δ 180.9, 179.6, 175.3, 175.1, 121.5 (q, J=292.6 Hz), 80.5-81.4 (m), 71.9, 71.6, 71.5, 71.4, 71.3, 69.9, 68.8, 67.5, 67.1, 60.6, 59.2, 53.9, 52.4, 51.9, 47.4; MS (MALDI-TOF) m/z 1295 (M$^+$+1, 100); HRMS (MALDI-TOF) calcd for C$_{39}$H$_{50}$F$_{27}$N$_4$O$_{13}$ 1295.2943, found 1295.2953.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound comprising the structure:

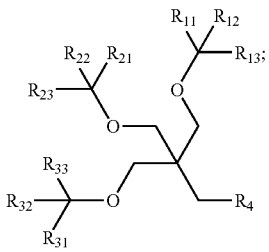

wherein $R_{11}$, $R_{12}$, $R_{13}$, $R_{21}$, $R_{22}$, $R_{23}$, $R_{31}$, $R_{32}$, and $R_{33}$ are CF$_3$; and wherein $R_4$ is H, OH, OBn, OC(CF$_3$)$_3$, alkyl, or alkoxy.

2. The compound of claim 1, wherein the compound is a surfactant.

3. The compound of claim 1, comprising a structure selected from:

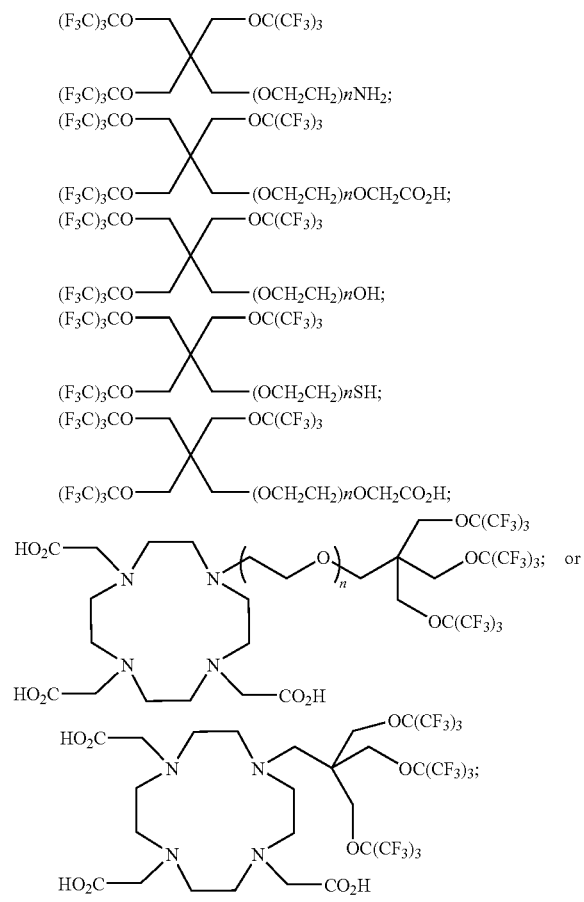

wherein n is from 2 to 10.

4. The compound of claim 1, wherein the compound is an oil.

5. The compound of claim 1, comprising a structure selected from:

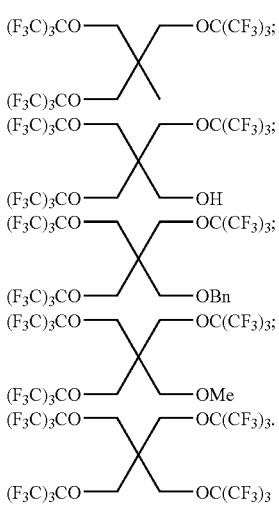

6. The compound of claim 1, wherein the compound exhibits maximum symmetric branching.

7. A process for the preparation of a compound comprising the structure:

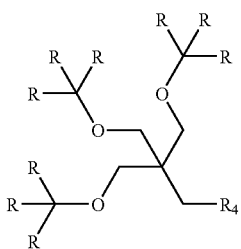

wherein R is $CF_3$ and wherein $R_4$ is H, OH, OBn, alkyl, or alkoxy;

the process comprising the steps of:
provide a triol,
reacting the triol with or nonafluoro-tert-butanol to provide a triperfluoro-tert-butyl ether.

8. The process of claim 7, wherein the compound comprises the structure:

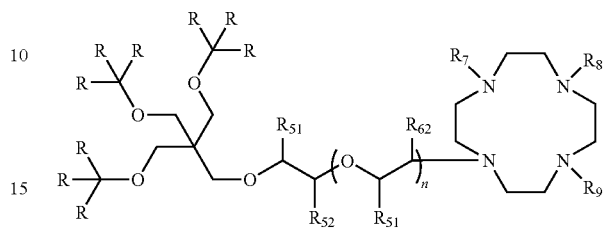

wherein n is 0 or a positive integer;

wherein $R_{51}$, $R_{52}$, $R_{61}$, and $R_{62}$ are, independently, H or alkyl; and wherein $R_7$, $R_8$, and $R_9$ are, independently, H, $CH_2CO_2H$, or alkyl.

9. The process of claim 8, wherein n is an integer from 4 to 12.

10. A delivery method comprising the steps of:
a. complexing a payload with one or more compounds of claim 6; and
b. administering the complex to a mammal in an effective amount.

11. The method of claim 10, comprising the steps of:
a. complexing a metal ion with a compound of claim 6; and
b. administering the complex to a subject in an amount effective for detection by $^1$H MRI.

12. The method of claim 10, comprising the steps of:
a. complexing a radionuclide with a compound of claim 6; and
b. administering the complex to a mammal in an amount effective for radiotherapy.

* * * * *